United States Patent
Larsen

(10) Patent No.: US 8,165,900 B2
(45) Date of Patent: Apr. 24, 2012

(54) PATIENT CHECK-IN/SCHEDULING KIOSK

(75) Inventor: Steven J. Larsen, Cross Plains, WI (US)

(73) Assignee: Epic Systems Corporation, Verona, WI (US)

( * ) Notice: Subject to any disclaimer, the term of this patent is extended or adjusted under 35 U.S.C. 154(b) by 1050 days.

(21) Appl. No.: 11/786,555

(22) Filed: Apr. 12, 2007

(65) Prior Publication Data

US 2007/0226010 A1     Sep. 27, 2007

Related U.S. Application Data

(63) Continuation-in-part of application No. 10/914,471, filed on Aug. 9, 2004, now abandoned.

(51) Int. Cl.
*G06Q 50/00* (2012.01)

(52) U.S. Cl. .................... 705/3; 705/2

(58) Field of Classification Search .............. 705/2, 3
See application file for complete search history.

(56) References Cited

U.S. PATENT DOCUMENTS

| | | | |
|---|---|---|---|
| 5,726,688 A | | 3/1998 | Siefert et al. |
| 6,047,259 A | * | 4/2000 | Campbell et al. ........... 705/3 |
| 6,094,640 A | | 7/2000 | Goheen |
| 6,121,968 A | | 9/2000 | Arcuri et al. |
| 6,232,972 B1 | | 5/2001 | Arcuri et al. |
| 6,571,215 B1 | * | 5/2003 | Mahapatro ............... 705/8 |
| 6,640,212 B1 | | 10/2003 | Rosse |
| 6,847,387 B2 | | 1/2005 | Roth |
| 6,981,242 B2 | | 12/2005 | Lehmeier et al. |
| 2002/0116235 A1 | | 8/2002 | Grimm et al. |
| 2003/0033079 A1 | | 2/2003 | Endicott |
| 2004/0138924 A1 | | 7/2004 | Pristine |
| 2004/0186744 A1 | * | 9/2004 | Lux .............................. 705/2 |
| 2005/0010485 A1 | | 1/2005 | Sarvestani et al. |
| 2005/0044508 A1 | | 2/2005 | Stockton |
| 2005/0125265 A1 | | 6/2005 | Bramnick et al. |
| 2005/0131856 A1 | | 6/2005 | O'Dea |
| 2005/0144642 A1 | | 6/2005 | Ratterman |
| 2005/0234741 A1 | | 10/2005 | Rana et al. |

(Continued)

FOREIGN PATENT DOCUMENTS

GB         2 228 123         8/1990

(Continued)

OTHER PUBLICATIONS

Touch Vision; Check in; www.touchvision.com webpage.
Galvanon; Case Study—MediKiosk; 2002-2005 Galvanon, Inc.
Webpage, Welcome to Innovation Health Centers; www.otechgroupllc.com.

(Continued)

*Primary Examiner* — Gerald J. O'Connor
*Assistant Examiner* — Neha Patel
(74) *Attorney, Agent, or Firm* — Quarles & Brady, LLP

(57) ABSTRACT

A method and system for facilitating activity scheduling for a patient including the steps of providing an interface device for checking a patient in at the facility, receiving identifying information for the patient, identifying currently scheduled appointments for the patient where the currently scheduled appointments are associated with currently scheduled appointment activities, identifying at least one additional unscheduled activity for the patient in addition to the currently scheduled appointment activities, identifying at least one suggested appointment schedule including at least one open time slot during which the patient may complete the additional unscheduled activity and the currently scheduled appointment activities and presenting the at least one suggested appointment schedule to the patient.

37 Claims, 31 Drawing Sheets

U.S. PATENT DOCUMENTS

| | | |
|---|---|---|
| 2005/0261942 A1 | 11/2005 | Wheeler |
| 2006/0000903 A1 | 1/2006 | Barry et al. |
| 2006/0111941 A1* | 5/2006 | Blom ............................... 705/2 |
| 2006/0206818 A1 | 9/2006 | Utter et al. |
| 2006/0261942 A1 | 11/2006 | Frank |
| 2006/0277071 A1 | 12/2006 | Shufeldt |
| 2007/0050197 A1 | 3/2007 | Efron et al. |

FOREIGN PATENT DOCUMENTS

| | | |
|---|---|---|
| WO | WO 97/17680 | 5/1997 |
| WO | WO 98/40826 | 9/1998 |
| WO | WO 2005/027011 A2 * | 9/2004 |
| WO | WO 2005/010636 A2 | 3/2005 |

OTHER PUBLICATIONS

St. Claire Interactive International; St. Clair Interactive Communications, Inc. Kiosk Administrator brochure, Toronto Ontario Canada.

NEC Solutions America; PersonalPass—Automated Patient ID & Admissions Facility Mapping; www.necsam.com/healthcare; 2005.

Paers, Ltd; Patient Access Electronic Record System; 2004 Paers, Ltd.

* cited by examiner

PATIENT CHECK-IN/SCHEDULING KIOSK

CROSS-REFERENCE TO RELATED APPLICATIONS

This application is a continuation-in-part of U.S. patent application Ser. No. 10/914,471 that was filed on Aug. 9, 2004 now abandoned and titled "Electronic Appointment Scheduling For Medical Resources".

STATEMENT REGARDING FEDERALLY SPONSORED RESEARCH OR DEVELOPMENT

Not applicable.

BACKGROUND OF THE INVENTION

The present invention relates to electronic medical record (EMR) systems and in particular to an EMR system allowing access to and entry of data by a patient to request and schedule appointments and medical resources for the patient.

Scheduling of medical providers, equipment, laboratory services, and other resources for patient appointments is a significant challenge in efficiently controlling medical resources and costs. Typically, scheduling is controlled by employees in a clinic or other medical facility, who communicate with the patients by phone and arrange the schedules manually. While, in some cases, these employees can arrange all of the resources required for a visit, frequently patients are required to schedule multiple procedures in a series of tests through a series of phone calls to different employees handing scheduling for related, but separate, facilities. Such arrangements can be time consuming and inefficient, both for the patients and the medical facilities.

Enlisting patients as active participants in their own healthcare can increase patient satisfaction and the quality of the healthcare experience while decreasing the cost of providing that care. One area in which patient satisfaction can be dramatically improved, therefore, is in providing greater control and easier access for the patient to request and schedule appointments for medical care. Providing such control to the patient also affords benefits to the medical facilities, as when scheduling is done by the patient, there is a reduced need for scheduling personnel.

As it is desirable to allow patients access to scheduling of their procedures in order to improve efficiency, a number of medical communities have used the Internet to allow patients to request, or in limited cases directly schedule appointments. These systems, however, have not proved to be particularly efficient for a number of reasons. First, known scheduling systems typically provide scheduling capabilities only in predetermined increments of time. These systems, therefore, cannot tailor the amount of time necessary for an appointment to the reason for the appointment, and therefore are not efficient in scheduling the time of medical personnel and resources.

Second, when patients schedule their own appointments, it is difficult for medical personnel to obtain necessary information from and provide necessary information to the patients prior to the visit. Therefore, for example, patients can arrive for appointments, and spend up to an hour filling out forms prior to meeting with a doctor. Additionally, as the medical practitioner does not know the reason for the visit prior to the arrival of the patient, the medical practitioner cannot prepare for the visit by providing instructions to the patient prior to the visit. This problem is particularly acute when evaluation of a medical problem requires multiple steps, such as, for example, laboratory work prior to meeting with a medical practitioner. Inadequate information, therefore, often result in return visits, which could have been easily avoided had sufficient information been available to both the patient and the physician.

After appointments are scheduled and a short time before the time slot reserved for an appointment, a patient travels to the facility at which the appointment is scheduled to take place, checks in for the appointment with a receptionist, completes necessary forms, typically waits in a waiting room to be called for the appointment, is moved into a room to participate in the appointment and, after the appointment is completed, checks out with a receptionist and leaves the facility at which the appointment occurred. Here, to expedite the check-in process, patient check-in kiosks are known that receive unique patient identifying information from a patient during a check in process and, when the identifying information is recognized by the kiosk, the kiosk allows the patient to check in for appointments. An exemplary check in kiosk is the MEDIKIOSK™ that by Galvanon.

In many cases it is optimal for a patient that is to participate in several different activities (e.g., tests, examinations, procedures, etc.) at a facility to schedule appointments substantially consecutively (i.e., cluster appointments) so that the patient can attend several appointments during a single visit to the facility instead of requiring multiple facility visits to complete the appointments. Thus, where a patient has to participate in first through fourth different activities at a facility, it may be desirable to schedule the first, second, third and fourth activities for consecutive time slots at 8:00 a.m., 8:30 a.m., 9:00 a.m. and 9:30 a.m., respectively. Scheduling software is known that allows patients or a facility scheduling employee to view existing appointments and to select open time slots for additional appointments that need to be scheduled for the patient where the selected time slots are temporally proximate currently scheduled appointments.

While appointment clustering is often optimal, sometimes appointments cannot be clustered because, when the appointments are scheduled, either (1) consecutive open time slots for resources required to complete activities are not available, (2) the patient associated with the appointments has previous time commitments that will not allow clustering or (3) one of the tests is dependent on the results of an earlier test. Thus, in many cases, despite efforts to cluster, consecutive appointments may be spaced apart by intermediate periods of an hour or more or appointments may have to be made on separate days despite the fact that the appointments will take place at the same facility.

One other scheduling issue that impedes optimal appointment clustering is that resource availability, patient schedules and unfulfilled orders often change in a fluid fashion so that the constraints on clustering a specific subset of appointments change over time. Thus, what a patient may think today is optimal appointment scheduling for a subset of appointments to take place two week from now may be far less than optimal next week or on the day that the appointments are to occur. For instance, when a first patient uses a kiosk to schedule first through third appointments two weeks prior to the day on which the appointments are to occur, schedules of resources required to complete the first through third appointment activities may be such that a first one hour intermediate period is required between the first and second appointments and a second one hour intermediate period is required between the second and third appointments. Nevertheless, on the day that the first through third appointments are to take place, it may be that a second patient cancels her appointment that was to occur during the first one hour intermediate period so that, optimally, the first patient's third appointment could be moved to the first one hour intermediate period.

As another instance, when a first patient uses an online kiosk to schedule first through third appointments approximately two weeks prior to the time when the patient would like the appointments to occur, the patient's own time commitments may not allow the patient to schedule the three appointments on the same day. Here assume that the patient's own time commitments require that the patient schedule the first through third appointments on first, second and third different days. In this example, it may be that the patient's time commitments change two days prior to the first appointment so that the patient could complete all of the first through third appointments on the first day and thereby avoid trips to the facility on the following two consecutive days.

As still one other instance, in many cases patient's are unaware of or have forgotten activities in addition to activities for which appointments have already been scheduled, that should be, could be, must be, or have been ordered to be performed at a facility prior to attending an appointment at the facility. Exemplary activities that a patient may be unaware of or may have forgotten include existing or standing physician orders for tests, procedures, examinations, consultations, etc., routine best practices procedures (e.g., a yearly physical for anyone over 50 years old, a yearly colonoscopy for men over 50 years old, etc.), prerequisite activities required before specific types of appointments, etc.

One solution to the problems associated with fluid patient and resource schedules and changing activities associated with patients has been to provide receptionists with access to scheduling software to allow receptionists to optimize scheduling whenever patient's check in for appointments. Here, known receptionist check in software provides notices to receptionists when a patient that is checking in has unfulfilled orders (i.e., physician orders for patients that have been requested but have not been scheduled). When the receptionist recognizes that a patient has unfulfilled orders, the receptionist has the ability to access separate standard appointment scheduling software and search for time slots to add appointments for the patient's unfulfilled orders. When one or more time slots for one or more unfulfilled orders is identified, if the patient agrees, the receptionist can add the appointment to the patient's schedule.

While providing scheduling software to receptionists works well in theory, in practice, this solution has not proven very successful for several reasons. First, at many times medical facility receptionists are inundated with patients checking in for appointments and simply cannot take additional time with each patient during check in to attempt to optimize patient appointment clustering. This is particularly true in cases where receptionists are required to use standard scheduling software to schedule new appointments as standard scheduling software tends to be rather complex and requires several steps and associated time to identify and select possible time slots for activities.

Second, many receptionists are not well trained in how to use scheduling software and therefore are uncomfortable tinkering with currently scheduled appointments. This is particularly true in cases where appropriateness of a time slot for an appointment may hinge on many factors in addition to whether or not the time slot is open for a required resource (e.g., rules governing which procedures can follow other procedures, required pre-appointment patient preparation, etc.).

Third, even when a receptionist is trained in using scheduling software and there is no backlog of patients checking in for appointments, in many cases the receptionist opts not to attempt to optimize patient schedules because there is no direct benefit to the receptionist by performing the additional activities (i.e., the benefit of an altered appointment is directly to the patient and the facility that increases utilization rates of resources, not the receptionist).

BRIEF SUMMARY OF THE INVENTION

The present invention provides a system for allowing patients or proxies for those patients to electronically scheduling medical resources. The system includes both a patient interface terminal or interface device, such as an internet terminal or a kiosk, and a computer system receiving time frame information and a reason for a medical appointment scheduling information from the patient interface terminal. Based on the information received, the computer system identifies a requested medical service, identifies resources required for the service, and presents schedule options at the interface terminal based on the identified medical services and resources. Because the reason for the visit is known, the computer system can schedule a time frame based on the reason for the appointment, thereby increasing efficiency. The resources scheduled can include a medical practitioner, and can also be other staff, a geographic office location, medical equipment, laboratory time, a room, or other resource necessary for a selected healthcare service. After schedule options are provided to the patient, the computer system can accept an input from the patient interface terminal to select an appointment from the schedule options, and submit the appointment data to scheduling software for the healthcare provider to directly schedule an appointment. As described below, when scheduling an appointment, the system automatically provides targeted questionnaires and necessary information for the appointment to assure that both the patient and the healthcare provider have necessary information before the appointment. These steps increase efficiency in the healthcare system, also as described more fully below.

In another aspect of the invention, the scheduling system can receive a range of schedule times or a range of geographic locations acceptable for the appointment, and can present schedule options for resources available within the range of schedule times or geographic locations. The scheduling system can also communicate with a database providing data indicating appointment lengths for different types of healthcare service appointments, and present a schedule of options which accommodate an appointment of the required length. The schedule options presented can also be filtered to indicate only healthcare providers and resources that can be coordinated in both time and geography to provide the healthcare service.

In still another aspect of the invention, the scheduling system can provide a reminder or alert notification to the patient interface terminal. The alerts can be provided at either predetermined intervals or at a time selected by the patient through the patient interface terminal. The scheduling system can also receive from the patient interface terminal a notice of appointment cancellation and submits cancellation data to a schedule for the resource.

In still another aspect of the invention, the scheduling system can include a central database holding schedules for healthcare providers and resources, and can accesses the central database to identify healthcare providers for the service and identify resources required for the service to present schedule options according to common schedule openings of healthcare providers and resources. The common schedule openings can also be provided for healthcare providers and resources within a predetermined geographic range.

In yet another aspect of the invention, the schedule system of the present invention can accommodate the scheduling of healthcare services requiring multiple sequential steps. The computer system can identify healthcare providers and resources for each step of the service, and provide different combinations of the multiple providers and resources. Thus, for example, in a multi-step process, the first step can require a laboratory test and the computer system communicates with a database providing data indicating laboratory test processing delay, and the computer system can determine the appropriate steps to accommodate the required delay. The scheduling system can also communicate with a database or a web service (*i.e., Yahoo Traffic, etc.), a satellite link, or any other technology that provides travel time delay information between the geographic locations and present schedule options which accommodate the travel time delay or present information on travel time estimates or delays. The computer system can also store the series of steps together in a log or other data structure such that, if a cancellation request is received, all steps for the procedure are cancelled.

In yet another aspect of the invention, a system for scheduling patient appointments is provided which includes a patient interface terminal, and a computer system scheduler communicatively coupled to the patient interface terminal and to a medical record database which includes medical data for specific patients. The computer system is adapted to receive data from the patient interface terminal to identify a patient making a request, and to filter medical services available to the patient based on the patient's identity. By identifying the patient, it is possible to filter healthcare services, information, and data based on the age, gender, patient medical and health history or other patient characteristics, to provide improved and more appropriate/targeted healthcare service. Thus, by integrating the check in software with a patient's electronic medical record, the present invention presents functionality that is far more useful than functions that can be provided via known check in kiosks.

In yet another aspect of the invention, the computer system can be further adapted to provide information to the patient based on a reason for the medical appointment, and receive data from the patient based on the reason for the medical appointment. In particular, the computer system can provide detailed questionnaires at the patient terminal which are tailored to obtain data for a particular medical appointment and/or medical resource. To increase efficiency, the computer system can also populate the questionnaire with available data from a medical records database and/or filter the questions provided to the patient based on known data about the patient.

These particular objects and advantages may apply to only some embodiments falling within the claims and thus do not define the scope of the invention.

In addition, according to at least some embodiments of the present invention, when a patient accesses a kiosk or interface device to check in for an appointment, in addition to allowing the patient to check in for currently scheduled appointments, the check-in kiosk identifies one or more additional activities that the patient may schedule temporally proximate the currently scheduled appointments and provides the option to schedule those activities. Here, the additional activities may include existing or unfulfilled orders, routine best practices activities (e.g., a yearly physical for all patients 50 years or older, etc.), prerequisites for one or more of the appointments for which the patient is attempting to check in, etc. Hereinafter, unless indicated otherwise, the phrase "additional unscheduled activities" will be used to refer generally to all unscheduled activities for a patient that can be identified by an inventive system and includes but is not to be limited to unfulfilled orders, prerequisites for currently scheduled appointments, routine best practices activities, activities that can automatically be identified via examination of a patient's electronic medical record, etc.

In at least some cases it is contemplated that, in addition to identifying additional unscheduled activities that may be scheduled, the system may also identify resources required to complete the activities, access resource schedules to identify open time slots for the resources that are temporally proximate to currently scheduled appointments, where two or more resources are required at the same time for an activity, identify times slots when all of the needed resources are available at the same time and then suggest a new suggested appointment schedule that includes at least one time slot for at least one of the additional activities.

In some embodiments it is contemplated that the system will examine all scheduling possibilities that may make sense for a patient and present seemingly optimal possibilities first followed by possibilities that seem less optimal when the seemingly more optimal possibilities are rejected or not selected by a patient. Here, "optimal" possibilities may include, for instance, time slots that are within one hour of currently scheduled appointments or that are between two currently scheduled appointments where anticipated travel times can be accommodated while less optimal possibilities may include time slots that are within a one to two hour range of currently scheduled appointments and still less optimal time slots may occur on subsequent days within one hour of currently scheduled appointments that are to occur on the subsequent days.

Thus, in some cases the system may even determine how currently scheduled appointment time slots can be altered to best optimize use of a patient's time by effective clustering. For instance, in some cases the system may simply suggest that one or more currently scheduled appointments be shifted to eliminate intermediate times between consecutive appointments. In other cases the system may suggest that a currently scheduled appointment be shifted to a new time slot (e.g., one hour later than the original time slot for the appointment) to allow an additional unscheduled activity to be scheduled. In still other cases the system may suggest that one or more additional unscheduled activities be added to a patient's schedule either before currently scheduled appointments (i.e., in a case where a patient arrives early to check in for a first currently scheduled appointment), in between two currently scheduled appointments or after a last scheduled appointment.

In at least some embodiments, by providing scheduling tools to patients upon check in, the additional work associated with optimizing a patient's schedule is placed directly with the party (i.e., the patient) who benefits most from optimized appointment clustering. In this regard most patients would find it advantageous to reduce the amount of time at, and minimize the number of trips to, a facility to complete all required activities. For this reason alone it is expected that optimized scheduling will increase appreciably by providing check in kiosks that allow patients to perform the optimization.

In addition, it has been recognized that, while a conventional receptionist is often inundated with patients checking in and therefore cannot take additional time with each patient to attempt to optimize the patient's appointment schedule, a typical patient has nothing to do at a medical facility other than attend scheduled appointments and, in fact, often arrives several minutes (e.g., 15-30 minutes or more) prior to the time slot reserved for a first appointment during which the patient may have nothing to do. Here, it is believed that providing schedule optimizing tools to a patient at a time when the patient often has nothing better to do will result in a higher level of scheduling optimization.

Furthermore, in some embodiments, when a patient arrives late for a currently scheduled appointment, the check in kiosk may be programmed to, after identifying the patient, indicate that the patient is too late for the scheduled appointment, identify other options for the appointment, present the other options to the patient and allow the patient to reschedule the appointment without requiring aid from a receptionist, a staff member or other facility employee. Thus, for instance, where a patient arrives ten minutes after an appointment was to be completed and therefore missed the appointment, the check in kiosk may identify an open appointment time slot 45 minutes later and may present that open slot as an option for rescheduling. Where the open slot is accepted by the patient, the kiosk would add the patient to the schedule. In addition, here, because the patient would have a 45 minute waiting period, the kiosk/system may be programmed to attempt to identify other activities for the patient to fill in a portion of the 45 time slot.

Moreover, in at least some embodiments, scheduling options are only offered to patients when seemingly optimal options or options that are better than a current appointment schedule exist. Thus, for instance, when a patient that is associated with three additional unscheduled activities logs on to a check in kiosk to check in for first and second currently scheduled appointments at 8:30 a.m. and 10:30 a.m., an inventive system may identify the three additional unscheduled activities, identify resources required to perform the unscheduled activities and determine if there are any open time slots for the required resources that are temporally proximate the current 8:30 and 10:30 appointments or if the current appointments could be shifted to accommodate one or more of the additional unscheduled activities. Here, if no open slots are identified and none of the currently scheduled appointments can be shifted to accommodate at least one of the additional unscheduled activities, the system simply allows the patient to check in for the currently scheduled appointments without indicating that the patient has additional unscheduled activities. In the alternative, where an open time slot is identified for one or more of the additional unscheduled activities or current appointments can be shifted to accommodate one or more additional unscheduled activities, the system provides the option to schedule the additional unscheduled activity(s). Thus, in at least some embodiments, patients are only notified of additional unscheduled activities when scheduling options are available.

Furthermore, in at least some embodiments, the scheduling portion of the check in interface only provides a reduced set of scheduling options which enables configuration of an extremely simple and intuitive interface device. To this end, in the above example where a patient is associated with three additional unscheduled activities and is checking in for 8:30 a.m. and 10:30 a.m. appointments, it is likely that the patient will only want to schedule one or more of the additional unscheduled activities for the same day as the currently scheduled appointments if the additional unscheduled activities can be scheduled temporally proximate the currently scheduled appointments (e.g., within one hour before the 8:30 appointment, within one hour after the 10:30 appointment or between the first and second appointments). Thus, at check in, in at least some embodiments, the time range during which scheduling options may be offered to a patient is automatically selected by the system and is extremely limited. By limiting scheduling times to a small period, the interface can be made extremely simple and easy to use.

In at least some embodiments the check in kiosk may also be used as a check out kiosk that allows a patient to attend to various post appointment activities such as, for instance, obtaining medication or care instructions, receiving referrals to other physicians, obtaining a list of additional unscheduled activities, scheduling additional unscheduled activities, etc. Here, in at least some cases where a physician adds information to a patient's electronic medical record during an appointment, an inventive system may be programmed to glean information from the patient's record that can be used to identify one or more additional unscheduled activities to suggest to the patient.

At check out, instead of providing a simplified scheduling interface, a more complete interface may be provided that allows the patient to see a large number of scheduling options. In some cases the check out scheduling interface may attempt to cluster additional unscheduled activities with currently scheduled appointments and, at least as an initial pass, may present a seemingly optimal and simplified scheduling option, only providing the more detailed scheduling interface when the simplified option is rejected by a patient.

It is also contemplated that, in at least some embodiments, the simplified scheduling interface may be added to a check-in interface used by a receptionist or staff member to reduce the amount of work and time required to optimize patient appointment schedules thereby increasing the likelihood that receptionists will attempt to optimize patient schedules. For instance, in some embodiments, instead of simply indicating that unfulfilled orders exist for a patient upon check-in and requiring a receptionist to access separate scheduling software to attempt to add those unfulfilled orders to a patients scheduled appointments, an inventive system will, if possible, automatically identify a suggested appointments schedule including at least one time slot for at least one of the unfulfilled orders and present the option to optimize to the receptionist. Thereafter, if the patient consents, the suggested appointment schedule can be quickly accepted and patient appointments updated accordingly.

Thus, at least some inventive embodiments include a method for allowing a patient at a medical facility using a public kiosk to schedule activities, the method comprising the steps of providing the kiosk in a location for use by patients, via the kiosk, receiving identifying information from the patient, identifying currently scheduled appointments for the patient where the currently scheduled appointments are associated with currently scheduled appointment activities and initially scheduled appointment time slots, identifying at least one additional unscheduled activity for the patient in addition to the currently scheduled appointment activities for the patient, identifying at least one suggested appointment schedule including at least one open time slot during which the patient may complete the additional unscheduled activity and the currently scheduled appointment activities and, via the kiosk, presenting the at least one suggested appointment schedule to the patient.

At least some cases further include the step of receiving input via the kiosk to accept the suggested appointment schedule and automatically adding the additional unscheduled activity to the appointment schedule to update the currently scheduled appointments. In some cases the step of identifying at least one additional unscheduled activity for the patient includes identifying multiple additional unscheduled activities for the patient in addition to the currently scheduled appointment activities for the patient and wherein the step of identifying at least one suggested appointment schedule includes identifying a schedule that includes open time slots during which the patient may complete each of the additional unscheduled activities and the currently scheduled appointment activities. In some cases the step of receiving identifying information occurs at a first time, the method further including the step of allowing the patient to check-in for any currently scheduled appointments that are temporally proximate the first time. In some cases temporally proximate appointments include appointments that occur within three hours of the first time. In some cases the method is for use after a first appointment has been completed and prior to the patient exiting the facility wherein the at least one additional unscheduled activity includes an unfulfilled order generated during the first appointment. IN some embodiments the steps of receiving input via the kiosk to accept the suggested appointment schedule and automatically adding the additional unscheduled activity to the appointment schedule to update the currently scheduled appointments includes presenting a single icon via a display screen that, when selected, causes the additional unscheduled activity to be added to the appointment schedule and receiving input via the single icon.

Other embodiments include a method for allowing a patient at a medical facility using a public kiosk to simultaneously schedule and check-in for an activity to be performed at the facility, the method comprising the steps of providing the kiosk in a public location for use by patients, providing an unfulfilled order database that includes unfulfilled orders wherein an unfulfilled order is an unscheduled activity requested by a clinician, via the kiosk, receiving identifying information from the patient, identifying at least a first unfulfilled order for the patient in the unfulfilled order database, via the kiosk, presenting the first unfulfilled order to the patient, via the kiosk, receiving input indicating that the patient intends to check in for the unfulfilled order and, upon receiving the input indicating that the patient intends to check-in for the unfulfilled order, storing an indication that the patient is checked in and placing the unfulfilled order in a schedule queue to be performed.

Still other embodiments include a method for automating patient checkout after an appointment, the method comprising the steps of, during an appointment, receiving at least one activity entry and storing the activity entry in a first EMR wherein an activity entry includes data usable to determine that at least one post-appointment follow-up activity associated with the activity entry should be performed, after receiving at least one activity entry: examining the EMR for any activity entries; and, when an activity entry is identified, identifying post-appointment follow-up activities associated with the identified activity entry, providing the kiosk in a public location for use by patients, via the kiosk, receiving identifying information from the patient, identifying post-appointment follow-up activities associated with the patient and, via the kiosk, presenting at least a subset of the identified post-appointment follow-up activities.

Yet other embodiments include a method for facilitating activity scheduling for a patient at a medical facility, the method comprising the steps of providing an interface device for checking a patient in at the facility for at least one currently scheduled appointment, via the interface device, receiving identifying information for the patient, identifying currently scheduled appointments for the patient where the currently scheduled appointments are associated with currently scheduled appointment activities and initially scheduled appointment time slots, identifying at least one additional unscheduled activity for the patient in addition to the currently scheduled appointment activities for the patient, identifying at least one suggested appointment schedule including at least one open time slot during which the patient may complete the additional unscheduled activity and the currently scheduled appointment activities and, via the interface device, presenting the at least one suggested appointment schedule to the patient.

Other embodiments include a system for facilitating activity scheduling for a patient at a medical facility, the system comprising an interface device for checking a patient in at the facility for at least one currently scheduled appointment, a database that stores currently scheduled appointments for the patient, a processor linked to the interface device and the database, the processor programmed to, when the patient logs onto the interface device: identifying currently scheduled appointments for the patient where the currently scheduled appointments are associated with currently scheduled appointment activities and initially scheduled appointment time slots, identify at least one additional unscheduled activity for the patient in addition to the currently scheduled appointment activities for the patient, identify at least one suggested appointment schedule including at least one open time slot during which the patient may complete the additional unscheduled activity and the currently scheduled appointment activities and, via the interface device, present the at least one suggested appointment schedule to the patient.

Some systems further include a database that stores additional unscheduled activities for patients wherein the processor is programmed to identify at least one additional unscheduled activity for the patient by accessing the database that stores additional unscheduled activities and identifying at least one unscheduled activity for the patient in the database that stores additional unscheduled activities. In the alternative, the processor may be programmed to identify at least one additional unscheduled activity for the patient by identifying circumstances associated with the patient and applying a set of rules to circumstances associated with the patient to identify the at least one additional unscheduled activity.

Other embodiments include a method for facilitating activity scheduling for a patient at a medical facility wherein the patient has at least one currently scheduled appointment on a first day, the method comprising the steps of providing an interface device for checking the patient in at the facility for the at least one currently scheduled appointment, during patient check in on the first day, identifying all currently scheduled appointments for the patient that are to occur on the first day where the currently scheduled appointments are scheduled for initial time slots, identifying at least one additional unscheduled activity for the patient in addition to the currently scheduled appointments for the patient that are to occur on the first day, identifying at least one suggested appointment schedule including the currently scheduled appointments for the patient that are to occur on the first day and at least one open time slot that is temporally proximate at least one of the initial time slots during which the patient may complete the additional unscheduled activity and via the interface device, presenting the at least one suggested appointment schedule to the patient.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE SEVERAL VIEWS OF THE DRAWINGS

FIG. 16 is a kiosk screen shot that presents a main kiosk menu for a patient to select from;

FIG. 23 is a sub-process that may be substituted for a portion of the process shown in FIG. 12 for identifying opportunistic activities that can be scheduled and facilitating scheduling of those activities prior to check in;

DETAILED DESCRIPTION OF THE INVENTION

Figure 1:
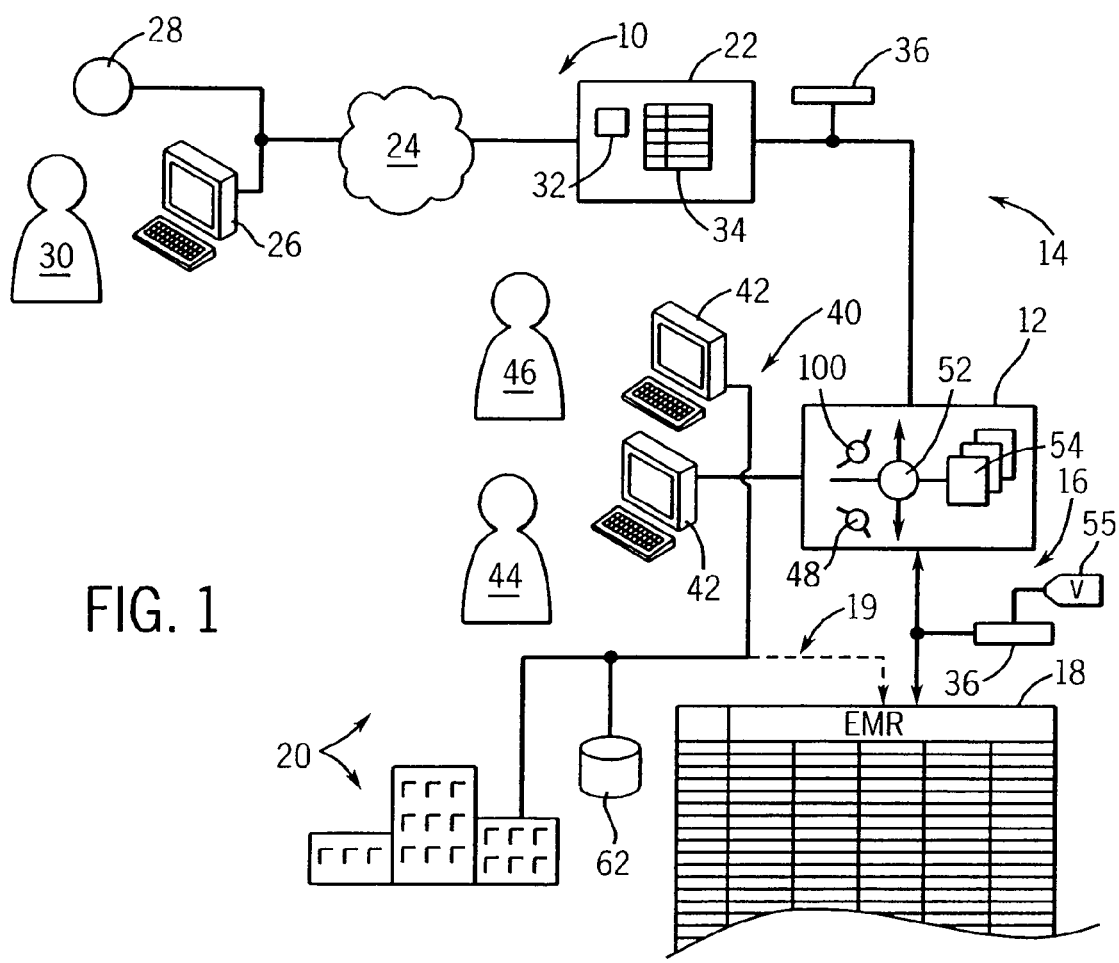
FIG. 1 is a simplified block diagram of a computerized interface for an EMR providing an Internet communication channel.

Referring now to FIG. 1, a patient scheduling system 10 per the present invention may include an interface module 12 standing between a patient communication channel 14 and an EMR communication channel 16, the latter communicating with an electronic medical record (EMR) database 18. Generally the interface module 12 is a program that may be physically located on an independent computer or run on a computer shared with another function such as the EMR database 18.

Generally, the EMR database 18 includes a complete medical history of many patients collected from a variety of healthcare sources 20 including physicians and other healthcare professionals such as members of the staff at hospitals, clinics, and laboratories communicating on standard EMR network 19. As will be understood to those of ordinary skill in the art, the EMR database 18 includes biographical information describing the patient, including the patient's age, gender, height and weight, and medical history information including the patient's medical conditions, previous medical procedures, medications, and laboratory test results. The EMR database 18 may be centrally accessed by many different healthcare sources 20 and thus serves as a path of intercommunication among many individuals working together to deliver healthcare.

The EMR database 18 is depicted as a single logical flat file for simplicity but may be configured in any of a variety of well known database formats including relational database structure, object database structures and the like. The data of the EMR database 18, like all medical records, is protected under federal law to ensure that sensitive data of this record is not released in a way that would violate a patient's privacy rights. EMR databases may be obtained from a variety of commercial sources including Epic Systems Corporation, the assignee of the present invention, who sells an EMR database under the trade name of "Chronicles" used with the "EpicCare" electronic medical record software.

The patient communication channel 14 may join the interface module 12 to a web server 22 providing a secure socket layer connection to the Internet 24. The Internet 24 may in turn connect a number of patient terminals 26 (only one shown for clarity) implementing a browser and/or a kiosk 28, provided, for example, at a doctor's office or elsewhere, either or both of which are used by a patient 30.

The web server 22 includes a number of active web pages 32, some of which will be described below, allowing the patient and/or monitoring system 28 to transmit and receive data securely to and from the web server 22. Incorporated into these web pages 32, for example as a CGI script, is a program for authentication of the patient's access to the web pages 32. The authentication control program makes use of a log-in identifier/password validation table 34 both shown as logically held on the web server 22 but in the preferred embodiment stored and executed remotely. The login identifier/password validation table 34 holds one or more patient specific tokens (for example, log-in identifiers and passwords but possibly including instead or in addition biometric data and the like) that ensure access to possibly sensitive medical data is not freely available to unknown parties. The patient 30 may also allow access to his or her medical records by a proxy or patient's representative also stored as links in the log-in password/password validation table 34 which gives each proxy a unique token. Generally, the term "patient" as used herein should be considered to include the patient and/or the patient's proxies. One important proxy, of a parent for children, may be initiated as a reminder based on knowledge about childbirth from the EMR.

The patient 30 must enter the text passwords and PIN password upon every new communication session. The text password and PIN password are not stored in cookie form on the patient terminal 26 or kiosk 28 such as might make anyone with access to the patient terminal 26 or kiosk 28 able to view or enter data on behalf of the patient 30. The table 34 may also include provisions allowing several different text passwords and PIN passwords to be associated with the same patient so that proxy access may be had by a patient's representative.

Data received by the web server 22 from the patient 30 is marked with a patient identification number and forwarded along the patient communication channel 14 as a patient identified message 36 to the interface module 12. Similar messages 36 may be received by the web server 22 along the patient communication channel 14 from the interface module and forwarded to the patient 30. Generally the messages 36 will be formatted to act as queries or responses to queries of or from the EMR database 18.

Referring still to FIG. 1, the interface module 12 may also connect to a provider communication channel 40 possibly using all or a portion of standard EMR network 19 allowing communication with healthcare sources 20 via terminals 42 associated, for example, with a primary care physician 44, a system administrator 46, laboratory services, and other service and resource providers. The resources may have access to the EMR database 18 directly per normal conventions or through the interface module 12 as will be described using a viewer/editor 48.

Access through the interface module 12 by the physician 44 also provides limited access to the patient 30. In this respect, some patient data in messages 36 sent by the patient 30 can be routed to a physician 44 and messages from the physician 44 may be routed to the patient 30 in the form of secure communications. Such email communications may also be initiated by the patient 30 as will be described further below.

Figure 2:
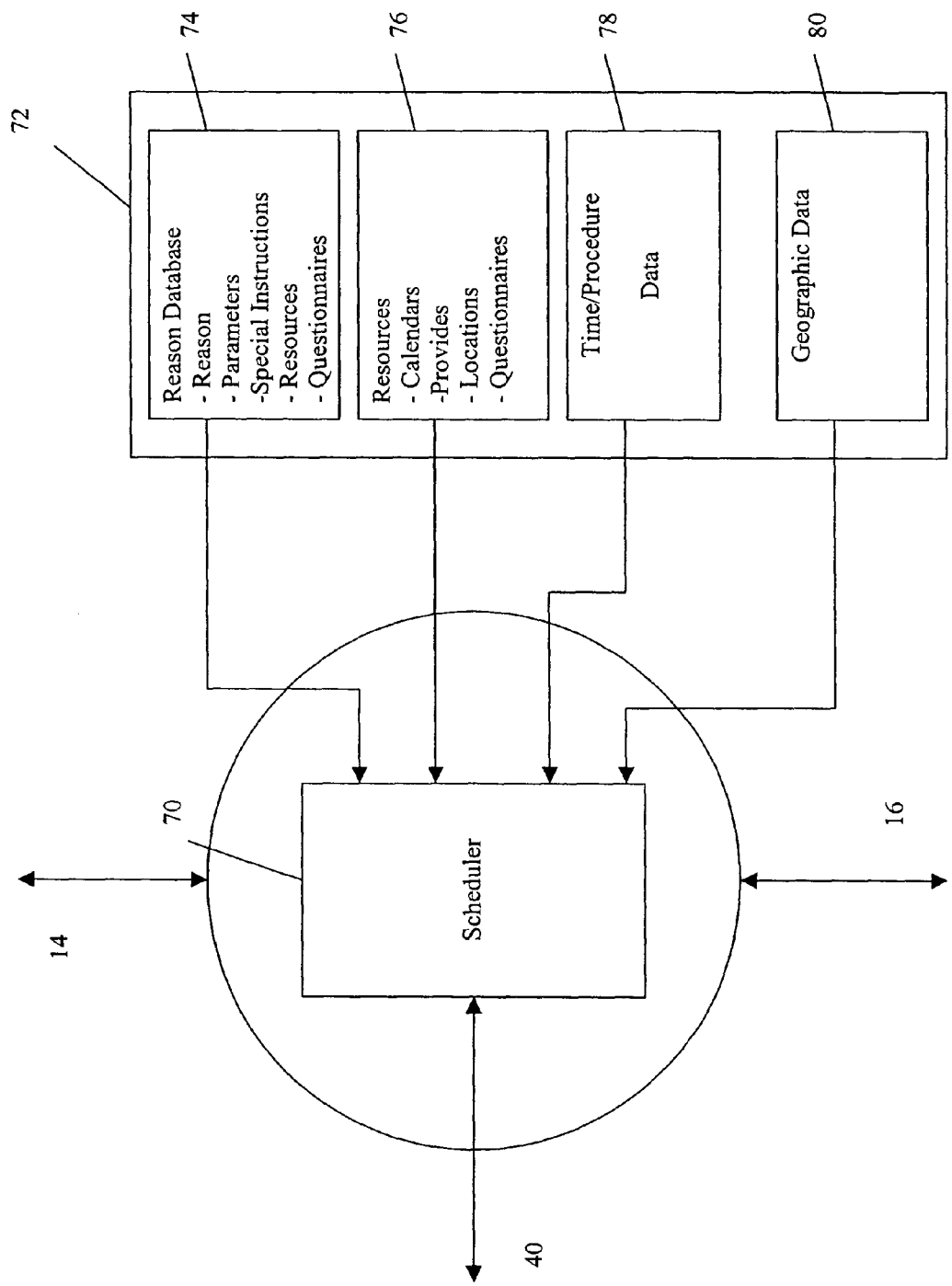
FIG. 2 is a detailed block diagram of the interface of FIG. 1 showing a scheduler and associated scheduling databases.

Referring now to FIGS. 1 and 2, the interface module 12 includes a scheduler 70 which includes a set of rules for scheduling appointments based on scheduling data found in a schedule database 72, data from the EMR 18 and data input at the server 22 by the patient 30 at a patient terminal which can be as described above at terminal 26 or kiosk 28. The scheduling database 72 can include a procedure or reason database 74, one or more resource database 76, time/procedure data 78 for correlating time periods to selected reasons or procedures, and geographic data 80, providing a location of a given resource and data correlating expected time to travel between one resource and others. The procedure or reason database 74 includes a series of possible reasons for an appointment along with parameters for determining whether a patient is eligible for the selected procedure, a list of resources required for the requested procedure and special instructions associated with the requested procedure. Such instructions can include information required by the patient such as, for example, the need for fasting prior to the procedure.

The resource database 76 can include medical resources which can be, for example, individual practitioners, clinics, medical equipment such as X-ray, CT, or MRI machines, laboratory resources or other practitioners' equipment or processes that need to be used in a medical procedure. Group meetings, such as educational meetings scheduled for a group of patients, can also be a resource. Detailed sets of questions (referred to hereafter as questionnaires) for acquiring information required from the patient, can be included with both the reason database 74 and the resource database 76. The questionnaires can be provided to the patient at the patient terminal 30, and the scheduler 70 therefore obtains required data from the patient based on the medical reason for the visit, the specific requirements of the provider or a clinic, and based on the requirements for a specific resource. Furthermore, patient information can be pulled from the EMR database 18 to populate portions of the questionnaire prior to providing the questionnaire to the patient, thereby minimizing the amount of input information required from the patient and increasing the efficiency of the scheduling system. Data from the EMR database 18 can also be used to filter the questions provided to the patient based on known data about the patient.

Although a number of separate databases with specific information are shown and described, it will be apparent that there are a number of ways to arrange and coordinate the data required for the scheduling process, any of which could be used as described herein. Furthermore, although the scheduling database 72 is shown in conjunction with the interface module 12, it will be apparent that the database can be provided at the server 22, as part of the EMR 18, in a separate memory component accessible to parts of the system, or elsewhere.

Figure 3:
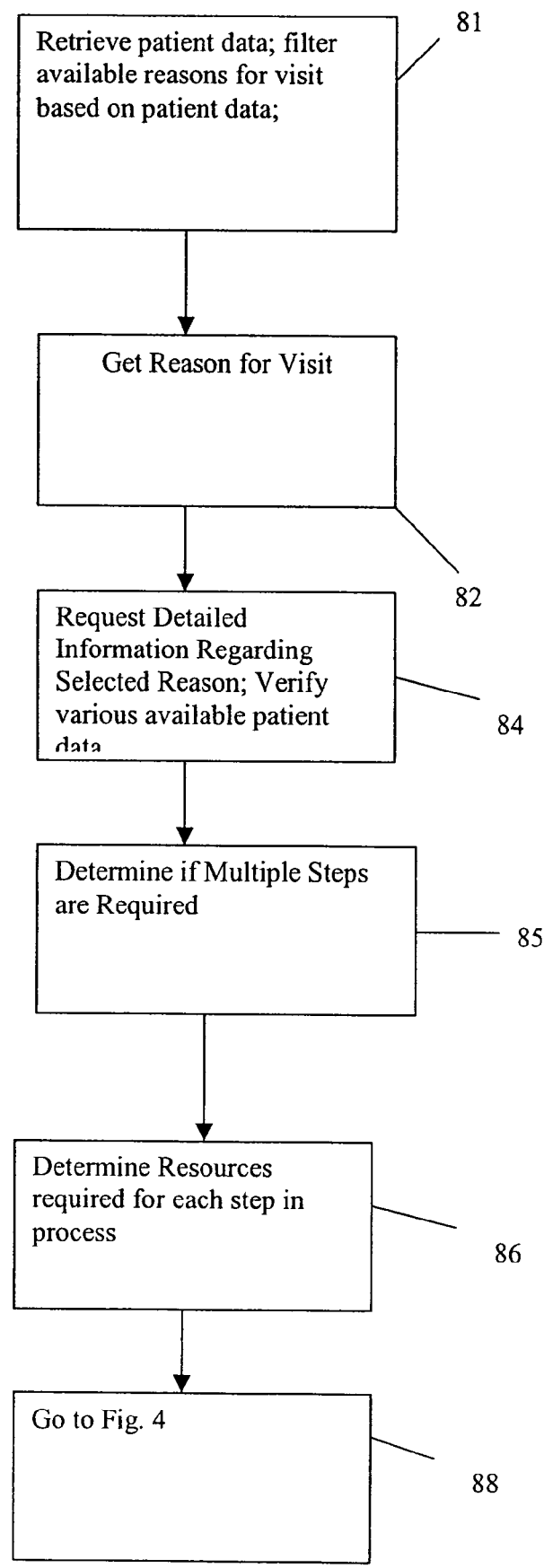
FIG. 3 is a flow chart showing the steps of data flow for retrieving a reason for an appointment from a patient.
Figure 4:
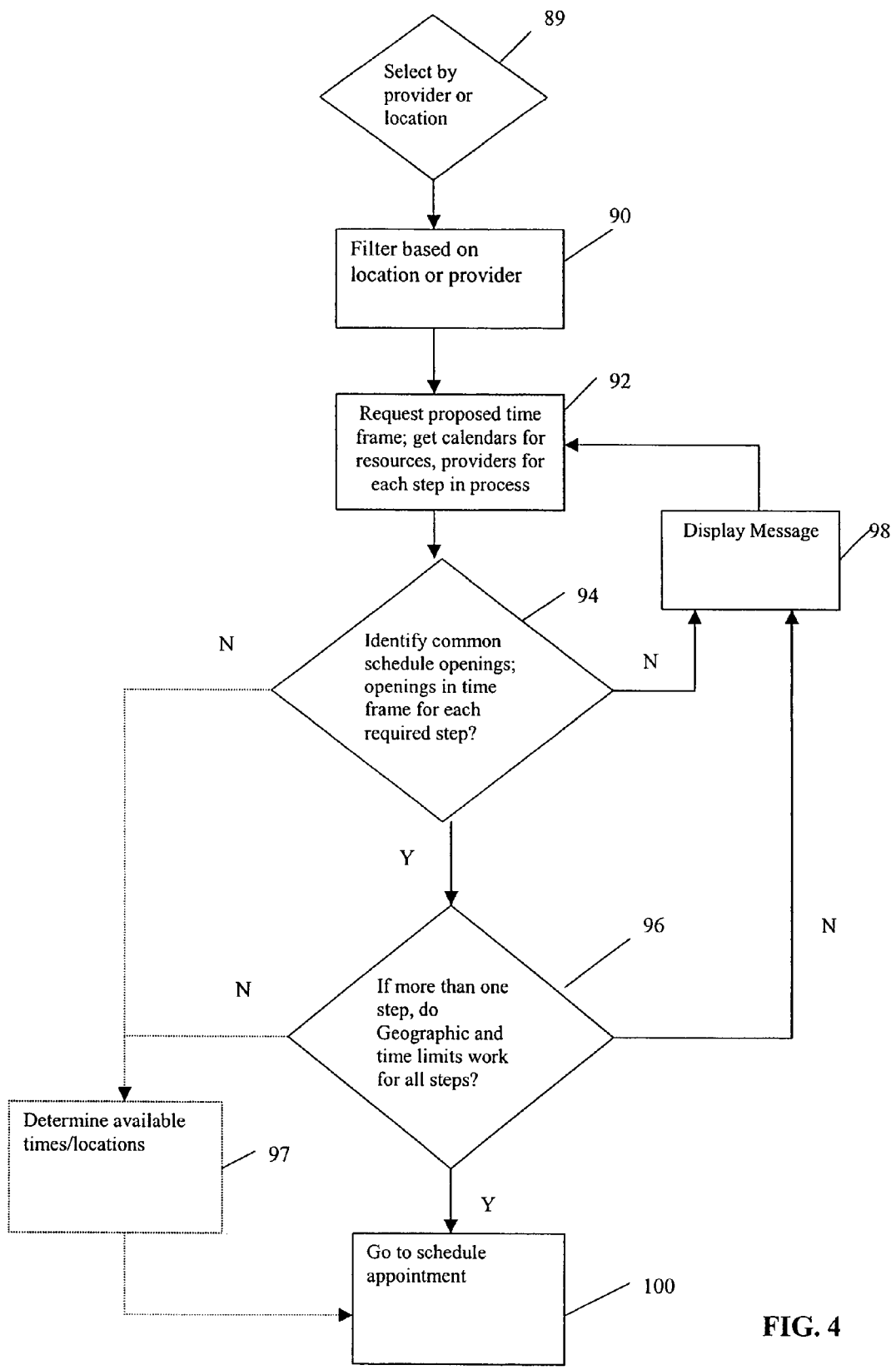
FIG. 4 is a flow chart showing the steps for determining one or more schedule option.
Figure 5:
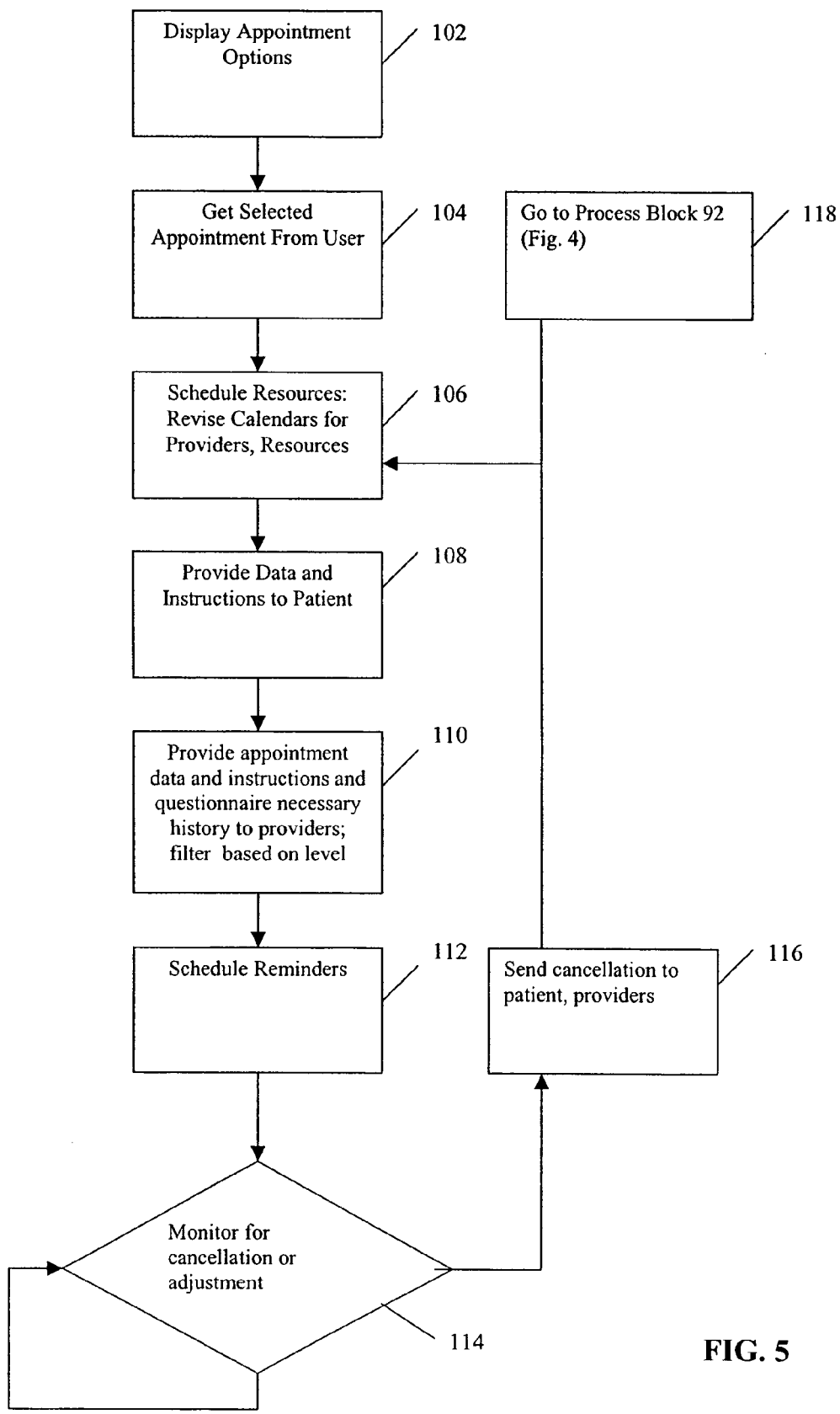
FIG. 5 is a flow chart showing the steps for scheduling an appointment and providing reminders.

Referring now to FIGS. 3-5, the operation of the scheduler 70 (FIG. 2) is shown. Referring first to FIG. 3, based on the patient identification, the scheduler 70 in process block 81 retrieves data from the EMR 18 (FIG. 1) regarding, for example, the age, sex, and medical condition of the patient, and filters the possible reasons for an appointment in reason database 74 based on these patient parameters to eliminate error and/or unnecessary selections. The scheduler 70 then queries the patient for a reason for an appointment, preferably by providing a menu of possible reasons on a page provided to the patient 30 from the web server 22. The user then selects a reason for the visit, as shown in process block 82. Although the process has been described as filtering possible reasons and presenting a menu, it will be apparent that the reason could also be entered as text or voice data. Furthermore, although shown and described as starting the process with entering a reason, the order and type of questioning could be varied such that, for example, the initial query is to select a provider, department, specialty, or facility. Any or all of these selections can be used to start the scheduling process. Although the invention is descried with reference to a particular order, the invention is not intended to be limited to any particular order.

After the initial data, such as a reason, has been received, the scheduler 70, in process block 84, requests detailed information associated with the request. The data request can be in the form of a questionnaire which can be, as described above, provided to the patient at the terminal 26 or kiosk 28, or, alternatively, retrieved from stored preferences selected by the patient. This information can include, for example, medical history, patient preferences such as language and gender of the caregiver, time and place of appointment, and other information required or desirable to process the request for an appointment. Based on the more detailed information retrieved in block 84, the scheduler 70 determines if multiple steps are required. For example, a procedure can be a visit to a medical practitioner, or consist of a multi-step process including laboratory testing and analysis followed by an appointment with a medical practitioner to review the results. Once the steps are determined, in process block 86 the scheduler 70 determines the resources required and, in process block 88, continues to FIG. 4 for scheduling and resource allocation.

Referring now to FIG. 4, in process block 89, the user is given the option of selecting either a location for the procedure or a medical provider, and in process block 90 resources are filtered by the scheduler 70 based on whether the patient would prefer a specific practitioner or a specific location. In process block 92, the scheduler system 70 also requests a proposed time frame for scheduling the procedure from the patient 30, and then accesses calendars or schedules in resource database 76 for the required resources for each step in the process. In process block 94, the scheduler 70 identifies common schedule openings between the resources required within the time frame specified by the patient. If the resource required cannot be scheduled within the time frame selected, a patient message is displayed in process block 98 and the patient is again queried regarding a proposed time frame, or, alternatively, in process block 97, the scheduler 70 generates a list of alternatives. These alternatives can include, for example, appointments at the same time but with different providers, appointments at the same time but at a different location, appointments with the same provider at a different time on an adjacent date, etc. After this list is generated, the scheduler proceeds to scheduling an appointment in process block 100.

If common schedule openings are found, in process block 96, and more than one step is required for the procedure, the time required for each step and the geographic distance between the related resources in the various steps are retrieved from the database 72, and the scheduler 70 determines whether the series of steps are compatible such that a patient could, within the required time frames, and within the cited geographical distances, complete all the steps of the procedure. For example, therefore, if laboratory tests are required before meeting with a medical practitioner, the scheduler 70 retrieves data to determine the amount of time that is required to process the laboratory data and transmit it to the medical practitioner, and how long it will take the patient to travel from the laboratory to the office of the medical practitioner. If the time and geographical requirements can be met, scheduling options are available. Once options are determined by the scheduler 70, the process proceeds to allow a patient to select a scheduling appointment from at least one and preferably a series of possible appointments as shown in FIG. 5. If not, the patient is returned to process block 92 and queried for another time frame.

Referring now to FIG. 5, in process block 102, one or more schedule opening have been determined and options for scheduling an appointment are displayed to the patient. While a number of possible schedule options can be displayed, the patient is prevented from viewing the entire schedule of any given practitioner or other resource. At no time, therefore, is the entire schedule displayed to the patient. In process block 104, the patient selects one of the scheduling options presented, and in process block 106, the scheduler 70 allocates the selected resources by revising the associated calendars in database 76 for each of the providers and/or resources that are required. If the procedure includes multiple steps, the scheduler 70 stores a linkage or log of the separate steps which can be used both for distributing information to the various resources in the log, and also for changing or canceling appointments as described below.

In process block 108, the finalized scheduling data is provided to the patient and the patient is provided with any special instructions required for the procedure. This notification can be provided directly to the kiosk 28 or computer 26, to a secure messaging address provided by the patient, or in the alternative through a voice automated voice-mail system or using various other user-selectable communication methods. The appointment data, instructions provided to the patient, the questionnaire data, and any necessary history required from the EMR 18 are also provided to the service providers and/or resource managers preferably through electronic communications such as secure messaging. The data provided to medical personnel can be filtered depending on the level of the service provider, and/or on a need-to-know basis. Furthermore, any additional patient questionnaires required from either the practitioner, a medical facility, or required for the use of a given resource can also be transmitted to the patient for completion, and the completed questionnaires transmitted to the necessary parties. As described above, patient information can be pulled from the EMR database 18 to populate portions of the questionnaire prior to providing the questionnaire to the patient.

Once both the resources and the patient are notified, the scheduler 70, in process block 112, schedules reminders to be sent to the patient and/or service providers. The reminders can be spaced either at a predetermined preset time or at a time frame selected by the patient and/or service providers. Again, these reminders can be e-mailed, provided through an automated voice-mail system, or provided through other user-specified communication channels such as secure messaging. After the reminders are scheduled, the scheduler 70 continues to monitor for cancellation either by the patient or one of the service provides or resources, or for an appointment change or adjustment provided by the service provider or a resource manager, as shown in process block 114. If a cancellation or adjustment request is received, a cancellation or adjustment notice is forwarded to the patient and to the associated providers in process block 116. In the case of an adjustment, the patient 30 can be given the option to accept the adjustment or start the scheduling process over. If a cancellation occurs or an adjustment is accepted, the calendars in database 76 for the service providers and associated resources are revised to reflect the fact that the time frames for use of the resources has changed. As necessary, a request can be forwarded to the patient 30 to enter a new time frame request. When an adjustment or a cancellation is made to a multi-step procedure, the scheduler 70 retrieves the log or linkage information for the steps, and cancels or adjusts all of the steps in the procedure as required.

The present invention therefore provides a number of important improvements in medical resource scheduling. As the scheduler 70 is connected to a database of patient information, the plausibility of a requested medical service can be verified for a specific patient, thereby limiting scheduling errors which can result in resources being tied up unnecessarily. Furthermore, the present invention simplifies and improves the efficiency of patient scheduling by limiting the number of personnel who need to be involved in the scheduling process, and by automating both the distribution of patient instructions and the collection of patient data required for a selected medical procedure, resource, or facility. Moreover, because the system is tied directly to patient data, detailed information about the patient can be easily and efficiently provided to medical service providers and managers with minimal keying of data by either the patient or the medical provider. Additionally, the scheduler 70 can tailor the length of an appointment to the requested medical procedure, thereby increasing the efficiency of medical practices. For medical procedures having multiple steps, the scheduler 70 can verify both time and geographic constraints, and further, can assure that all resources are notified in the event of a cancellation. The scheduler 70 can further filter the schedule options provided to a patient to prevent the patient from viewing the entire schedule of a service provider.

Although a specific data flow is described above, it will be apparent that variations in the order of data flow and retrieval can be made without departing from the invention. Furthermore, although specific hardware configurations are described schematically, it will be apparent that the invention can be used in conjunction with any number of different hardware and architecture configurations.

It is specifically, therefore, intended that the present invention not be limited to the embodiments and illustrations contained herein, but include modified forms of those embodiments including portions of the embodiments and combinations of elements of different embodiments as come within the scope of the following claims.

The systems above generally teach a scheduling system that can be used at any time and location to schedule appointments at a medical facility. In addition, the above system contemplates placement of patient scheduling kiosks (see 26 in FIG. 1) within a medical facility to, as the label implies, facilitate patient scheduling of appointments. It has been recognized that kiosks like kiosk 26 in FIG. 1 can, in addition to being used to facilitate scheduling, be used by patients at a medical facility to self check-in for appointments thereby alleviating or substantially reducing the need for receptionists or staff members throughout a facility.

In addition, it has been recognized that one particularly advantageous time at which to allow a patient to schedule appointments is when the patient is currently located at a medical facility at which activities associated with the appointments may occur and, more specifically, when the patient is at a facility to attend currently scheduled appointments. Thus, for instance, assume that four orders already exist (i.e., there are four unfulfilled orders where an unfulfilled order is an activity that has already been prescribed for a patient by a physician but has yet to be scheduled) for a first patient and that each of the four orders is related to activities that will eventually be performed at a first facility and that the first patient arrives at the first facility for two currently scheduled appointments, a first appointment at 8:30 AM and the second appointment at 10:00 AM where it is anticipated that the first appointment will only take 15 minutes so that there is a 1 hour and 45 minute gap between the two appointments. In addition, assume that the first patient arrives 35 minutes early at 7:55 AM for the first appointment (i.e., the 8:30 AM appointment). Here, the first patient has 35 minutes before the 8:30 AM appointment will likely have 1 hour and 45 minutes between the first and second appointments and may have additional time available after the second appointment is completed.

In the above case, it would be extremely valuable to the first patient if, upon checking in at 7:55 AM for the first appointment via a kiosk 26, the kiosk provides a reminder of the four existing and currently unscheduled orders and notice of the open time periods in the patient's appointment schedule so that the first patient can contemplate how the open times could be used effectively to complete some of the unfulfilled orders. It would also be valuable if, in addition to indicating unfulfilled orders and open time slots in the first patient's schedule, the kiosk also provides the option to the first patient to schedule appointments for the unfulfilled orders during any of the open times. Moreover, it would be advantageous if the kiosk and associated system components were programmed to, upon patient check-in, identify resources required to perform activities associated with existing unscheduled orders, examine schedules of the required resources and provide scheduling options to the patient that do not conflict with the patient's currently scheduled appointments.

Hereafter a check-in/scheduling system is described with reference to FIGS. 6-40 where the system includes various components that are similar to the components described above. In at least some cases where components are similar, similar labels are used in the figures. For instance, in FIG. 1, a patient kiosk is labeled 26 and in FIG. 6 patient kiosks are each labeled with number 26 followed by a small case letter (e.g., 26*a*, 26*b*, 26*c*, etc.), in FIG. 1 a database is labeled 72 and in FIG. 6 a database is labeled 72*a*, etc. Where components are similar to the components described above, in the interest of simplifying this explanation, the components described hereafter are not again described in detail.

Figure 6:
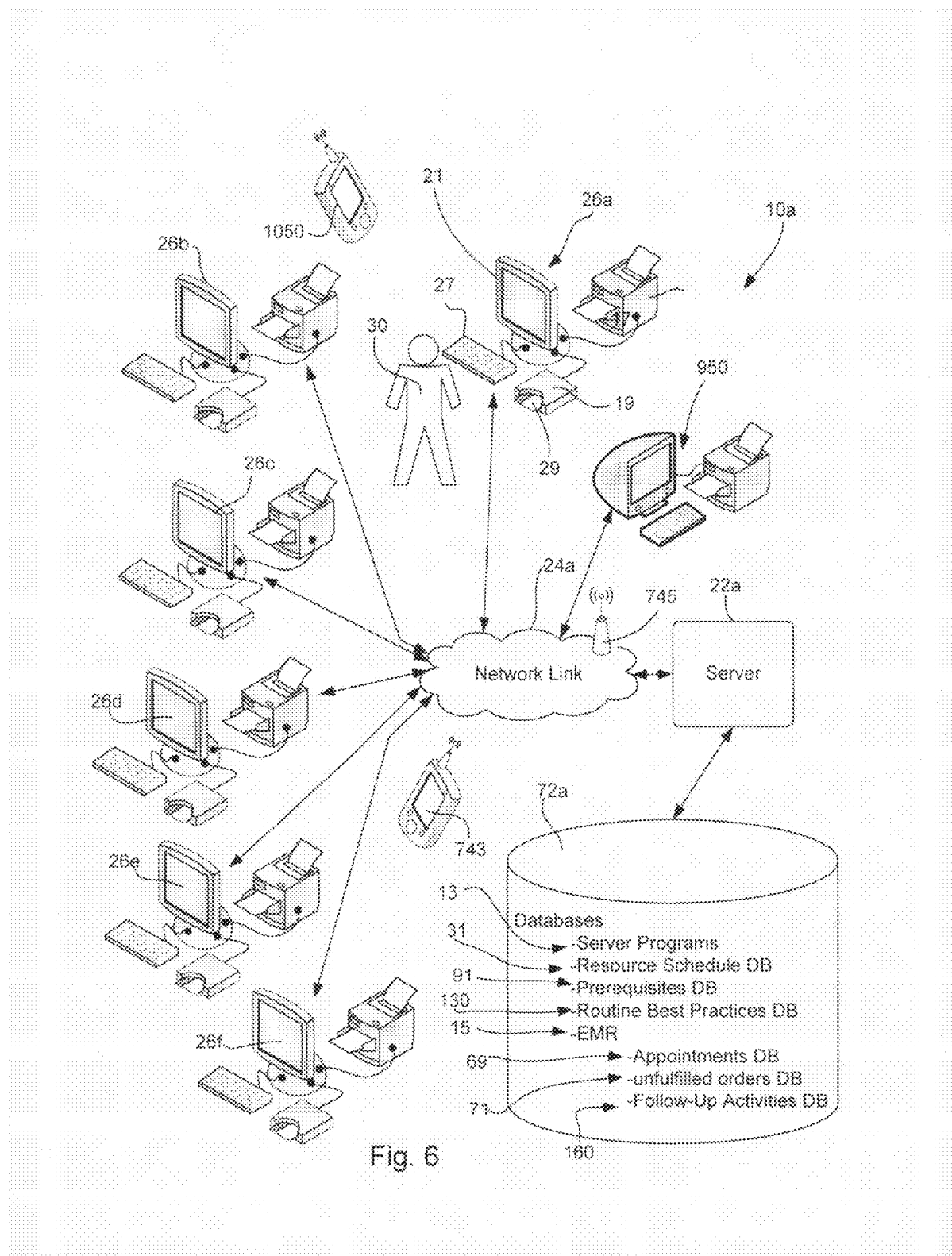
FIG. 6 is a schematic diagram illustrating an exemplary check in/scheduling system according to at least some aspects of the present invention.

Prior to describing the check-in/scheduling system shown in FIG. 6, it is helpful for consistency purposes to define some terms and phrases. To this end, the term "activity" will be used generally to refer to occurrences related to patients at a medical facility such as examinations, tests, procedures, consultations, etc. The phrase "currently scheduled appointments"

will be used hereinafter to refer to appointments for a patient that have already been scheduled for specific time slots. Here, typically one or more activities will be associated with each appointment and are to occur during the appointment. The phrase "unfulfilled order" will be used to refer to activities already ordered by a physician that have not been completed and that have yet to be scheduled. The phrase "suggested appointment schedule" will be used to refer to an appointment schedule that includes at least one tentative time slot for at least one unfulfilled order where the appointments have not been scheduled and are merely suggested to a patient. The phrase "additional unscheduled activities" will be used to refer generally to all unscheduled activities for a patient that can be identified by an inventive system and includes but is not to be limited to unfulfilled orders, prerequisites for currently scheduled appointments, routine best practices activities, activities that can be automatically identified via examination of a patient's EMR, etc. The term "patient" will be used in a broad sense to refer to a person or a proxy for a person where the person is to participate in some activity for a medical facility. Thus, for instance, Mr. Bruce Johnson who is to participate in a full physical exam may be a patient due to his participation in the examination or, Mr. Johnson may be considered a patient for the purposes of checking in and scheduling where his daughter Sophia is to participate in some facility activity.

Referring now to FIG. 6, an exemplary patient check-in/scheduling system 10a is shown and includes a server 22a, a database 72a, a network 24a (e.g., a local area network, a wide area network, the Internet, etc.), and a plurality of patient kiosks 26a, 26b, 26c, 26d, 26e and 26f. Server 22a runs software programs that perform various methods/processes that are contemplated by the present invention and to provide browser type screen shots to the kiosks 26a, 26b, etc., and to receive input from the kiosks. Each of kiosks 26a, 26b, etc., may take any of several different forms including work stations, personal computers, laptops, thin-client type devices, etc. Where the kiosks are more than thin clients, in at least some embodiments each kiosk may perform all or at least a subset of the steps required to perform the inventive processes. When the kiosks are thin client type devices, each kiosk operates primarily as a human-server interface device for input/output between a patient and server 22a where server 22a performs most or all of the inventive process steps. Hereinafter, unless indicated otherwise and in the interest of simplifying this explanation, it will be assumed that each kiosk 26a, 26b, etc., is a thin client type device.

Each of the kiosks 26, 265b, etc., is similarly constructed and operates in a similar fashion and therefore, in the interest of simplifying this explanation, only kiosk 26a will be described here in any detail. Kiosk 26a includes a flat panel display 21, an input device 27, a card reader 19 and a printer 17. Input device 27 is shown as a keyboard but may include other input devices such as a mouse device, a track ball type device, etc., and, is generally provided for, as the label implies, entering information into system 10a for use by server 22a. In the present case it will be assumed that the input device(s) 27 includes a keyboard for entering text type information and a mouse type device (not illustrated) for moving a mouse controlled cursor (see 351 in FIG. 13) around on the screen of display 21.

Card reader 19 includes a slot for receiving identification cards from patients for identification purposes. In this regard, card 29 may be credit card, a driver's license, a dedicated insurance card, a healthcare card, etc., from which, when slipped into the reader 19, information can be read to uniquely identify a patient using the card. To this end, prior to using one of the kiosks to check in for an appointment it is contemplated that patient identities will be associated with patient unique cards in database 72a.

Database or memory storage device 72a is linked to server 22a and stores programs 13 performed by server 22a and various databases that may be used by the server software to perform inventive methods. To this end, exemplary databases included in database 72a include a resource schedule database 31, a prerequisites database 91 and a best practices database 130. In addition, database 72a includes an electronic medical records database 15 that, as the label implies, stores electronic medical records (EMRs) for facility patients While EMRs often are extremely detailed, for the purposes of this disclosure portions of the EMR are particularly important. To this end, as shown in FIG. 6, EMR database 15 includes additional databases including an appointments database 69, an unfulfilled order database 71 and a follow-up activities database 160. Here, while each of databases 69, 71 and 160 are referred to as separate databases in the interest of simplifying this explanation, is should be appreciated that, in at least some cases, each database 69, 71 and 160 may in fact include data interspersed among separate patient EMRs. Thus, for instance, appointments for a first patient Mr. Bruce Johnson may be stored as part of Bruce Johnson's EMR while appointments for a second patient Ms. Mary Claire Johnson may be stored as part of Mary Claire's EMR.

Hereafter, simplified examples of each of the databases shown in FIG. 6 are described as including table formats (e.g., rows and columns). Nevertheless, it should be appreciated that each database may take any of several different forms and that the form is not important. Rather, the substance of the databases is important to the inventive methods and systems.

Figure 7:
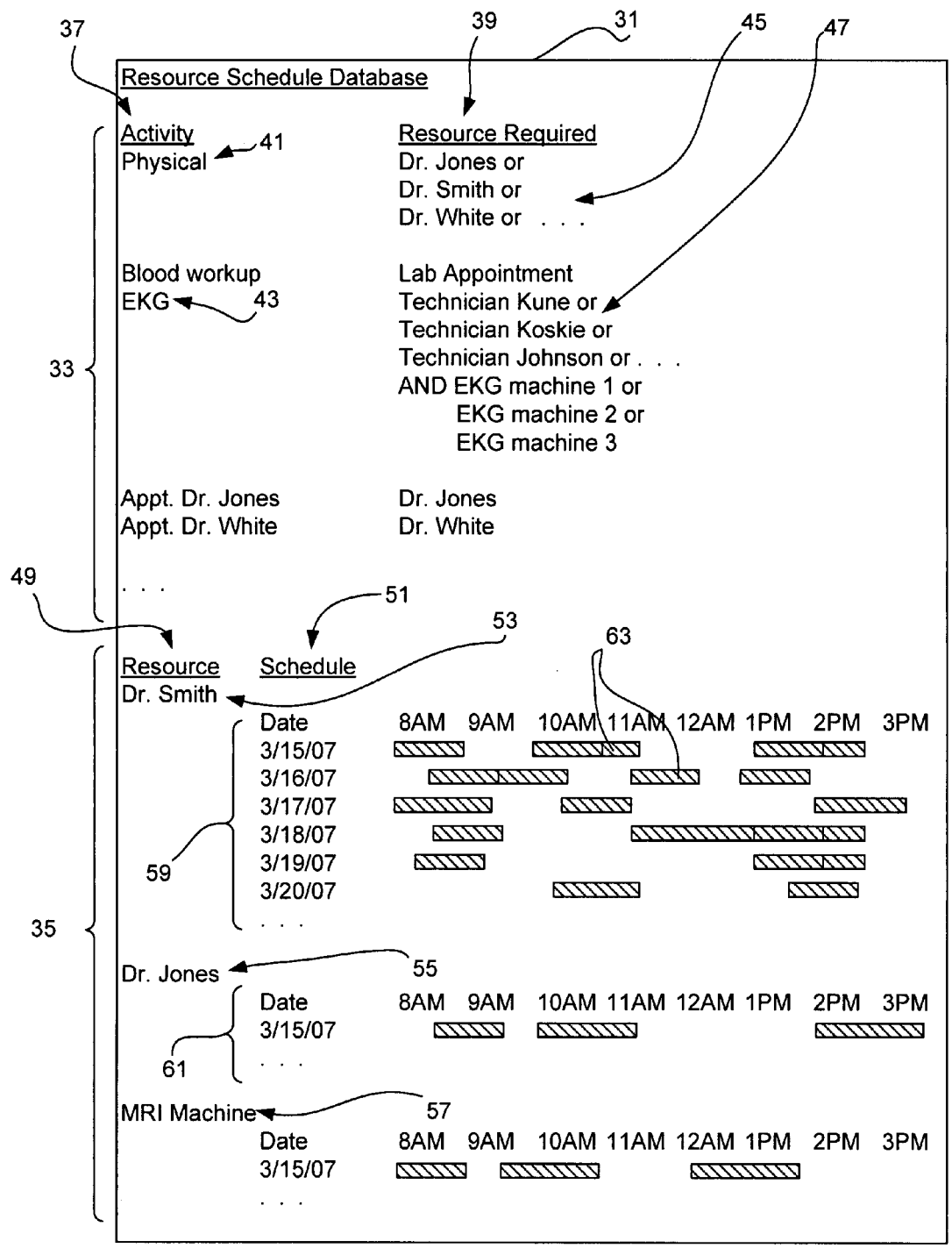
FIG. 7 is a schematic diagram illustrating one example of the resource schedule database of FIG. 6.

Referring to FIGS. 6 and 7, exemplary and simplified resource schedule database 31 includes an activity/required resource database 33 and a resource/schedule database 34. Activity/required resource database 33 correlates activities that may be performed at a facility and resources required to perform those activities. To this end, database 33 includes an activity column 37 and a required resource column 39. As the label implies, activity column 37 lists various activities that may be preformed at a medical facility. In FIG. 7, the exemplary activity list includes, among other activities, a physical 41, an EKG 43, etc.

Although a small number of activities are shown in FIG. 7, it should be appreciated that a typical activity list at a typical medical facility may include thousands of different activities. In addition, it should be appreciated that some activities may be complex, meaning that the activity has multiple characteristics. For example, a complex activity may include a physical that has been ordered by a specific physician (e.g., Dr. Jones) where the activity has two characteristics, the first being the nature of the activity (e.g., a physical) and the second being the ordering physician (e.g., Dr. Jones). In this example, the ordering physician may be important where different physicians require different tests to complete a physical where the different tests require different resources.

Referring still to FIG. 7, the required resource column 39 includes a subset of resources required or alternatively required resources for each one of the activities listed in activity column 37. Thus, for instance, in the case of the physical activity 41 in column 37, required resource column 39 indicates that any of several different doctors including Jones, Smith and White, is required to perform the physical (see 45 in FIG. 7). Similarly, for the EKG activity in column 37, required resource column 39 indicates that any of several different technician (see 47) can perform the EKG. In addition, required resource column 39 indicates that one of three different EKG machines is required to perform the EKG activity in column 37. In other cases, although not illustrated, it is contemplated that three or more resources may be required to perform or facilitate any one of the activities in column 37 and, in those cases, column 38 would indicate each of the required resources.

Referring yet again to FIG. 7, the resource/schedule database 35 includes a resource column 49 that lists each of the resources used at a facility. Exemplary resources listed in column 49 include Dr. Smith 53, Dr. Jones 55 and an MRI machine 57. Here, while only three resources are listed in column 49, it should be appreciated that at a typical medical facility there may be several thousand different resources listed in column 49. In addition to including resource column 49, resource/schedule database 35 includes a separate schedule in a schedule section 51 for each of the resources listed in column 49. To this end, a portion of an exemplary schedule 59 for Dr. Smith 53 is shown in FIG. 7. The portion of Dr. Smith's schedule that is shown corresponds to the dates Mar. 15, 2007 through Mar. 20, 2007 and shows Dr. Smith's schedule from 8:00 a.m. through 3:00 p.m. during each of the days. Bars 63 in the schedule 59 represent currently scheduled time slots and spaces between adjacent bars represent open time slots in Dr. Smith's schedule. While only a portion of Dr. Smith's schedule is shown, it should be appreciated that other parts of the schedule would indicate Dr. Smith's availability during the remainder of each business day and for other days during the calendar year. A small portion 61 of Dr. Jones' schedule is also illustrated as is a small portion (not labeled) of the MRI machine schedule.

Figure 8A:
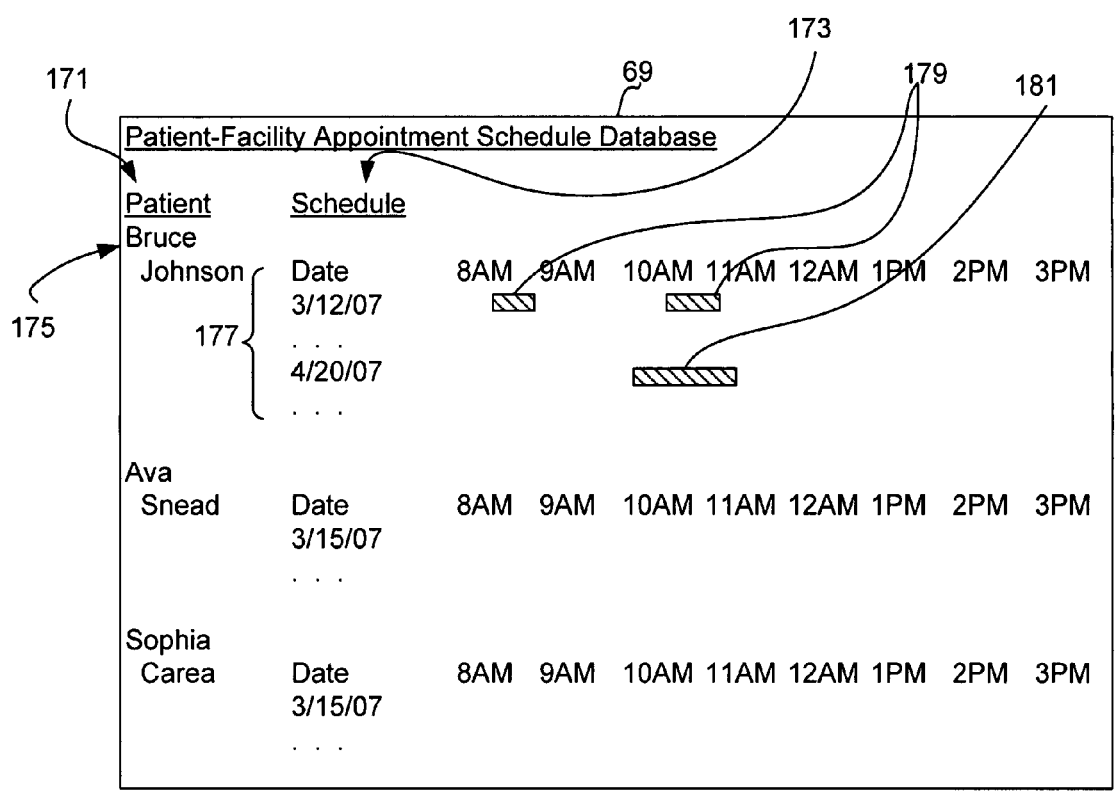
FIG. 8A is a schematic diagram illustrating one example of the appointments database of FIG. 6.

Referring now to FIG. 8A, an exemplary patient appointments database 69 is illustrated which includes a patient column 171 and a schedule section 173. Patient column 171 lists all facility patients including exemplary patients Bruce Johnson 175, Ava Snead (not labeled) and Sophia Carea (not labeled). Schedule section 173, like the resource schedule section 51 shown in FIG. 7, includes separate currently scheduled appointments schedule for each patient in column 171. An exemplary schedule for Bruce Johnson is labeled 177 and includes bars 179 and 181 that indicate time slots associated with currently scheduled appointments. Although not shown, database 69 would also store detailed information related to each schedule appointment including resources required, appointment location, information required by the patient prior to the appointment, special pre-appointment patient instruction (e.g., for some lab work and procedures patients need to fast for 12 hours prior to occurrence of the activities, etc.), etc.

Figure 8B:
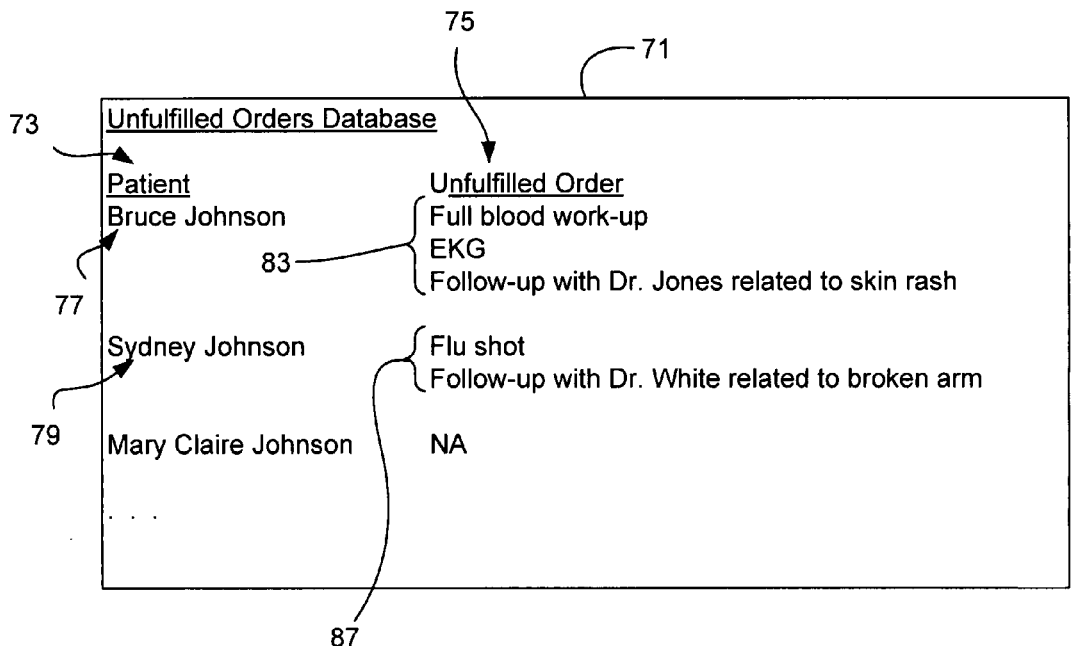
FIG. 8B is a schematic diagram illustrating one example of the unfulfilled orders database of FIG. 6.

Referring now to FIG. 8B, exemplary unfulfilled orders database 71 is shown and includes a patient column 73 and an unfulfilled order column 75. Patient column 73 lists each client of a medical facility. Exemplary clients in column 73, include Bruce Johnson 77 and Sidney Johnson 79. Unfulfilled order column 75 lists unfulfilled orders for each one of the clients in column 73. For example, for Bruce Johnson 77 in column 73, column 75 lists three unfulfilled orders 83 including a full blood work-up, an EKG and a follow-up with Dr. Jones related to a skin rash. Similarly, for Sidney Johnson 79, unfulfilled order column 75 lists two unfulfilled orders 87 including a flu shot and a follow-up with Dr. White related to a broken arm.

Referring once again to FIG. 6, the follow-up activities database 160, prerequisites database 91 and best practices database 130 will be described in greater detail below with reference to FIGS. 11, 9 and 10, respectively.

Figure 12:
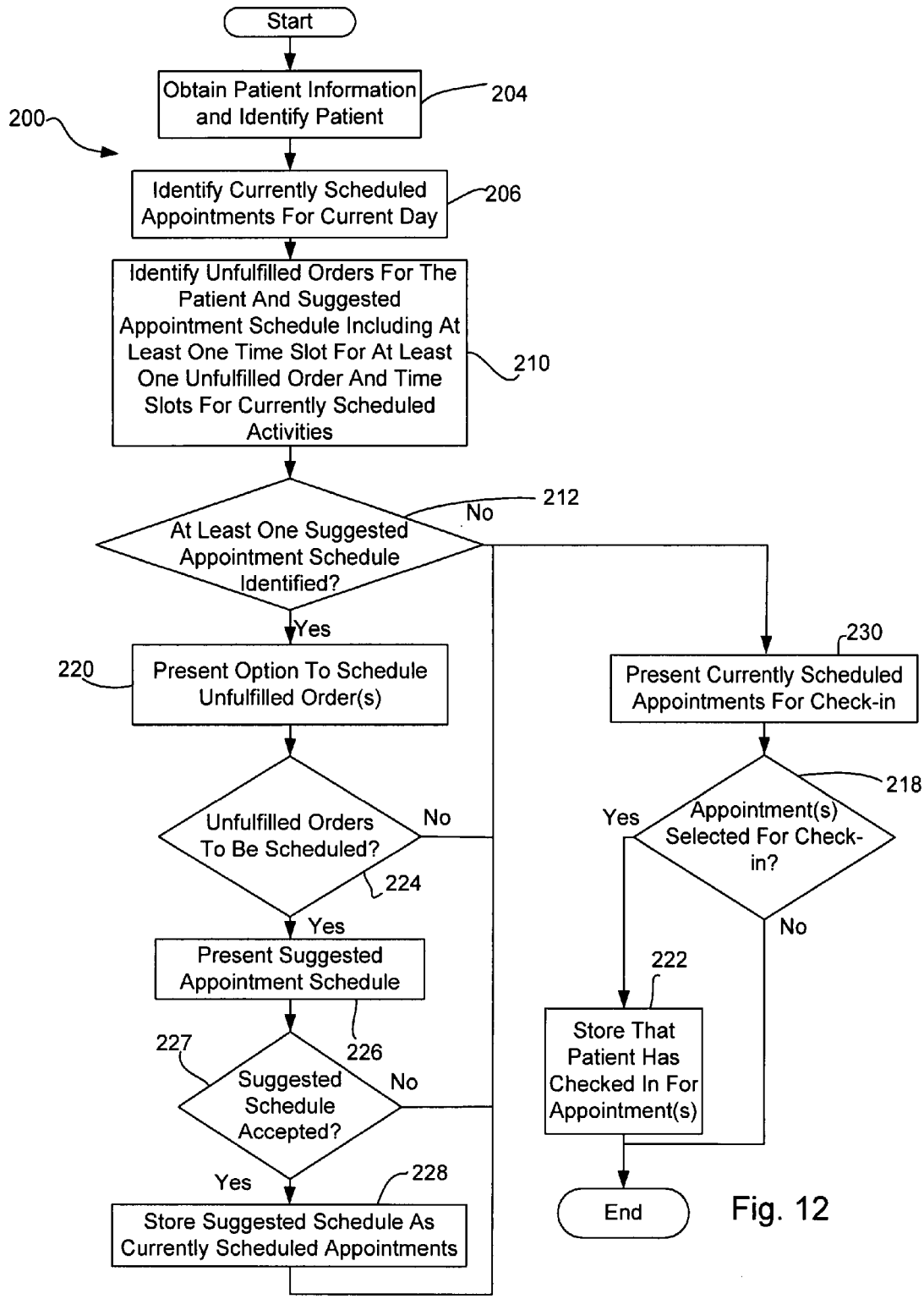
FIG. 12 is a flow chart illustrating a method consistent with at least some aspects of the present invention and may be performed by the system shown in FIG. 6.

Referring now to FIG. 12, an exemplary method 200 that is consistent with at least some aspects of the present invention is illustrated for, referring also to FIG. 6, when a patient checks in using one of the check-in kiosks, identifying existing unscheduled orders for the patient, identifying time slots during which the unfulfilled orders may be completed and that do not conflict with currently scheduled appointments and enabling the patient to schedule the unfulfilled orders for the suggested time slots.

Hereafter, in the interest of simplifying this explanation a practical example of how method 200 progresses is provided. Referring also to FIG. 6, hereinafter, it will be assumed that system 10a is located at St. Mary's medical facility where kiosks 26a, 26b, etc., are positioned at various locations throughout the facility. It will also be assumed that a patient, Mr. Bruce Johnson, walks up to check-in kiosk 26a to use that kiosk to check-in for two currently scheduled appointments including a first appointment at 8:30 a.m. for a follow-up visit related to a hernia operation with Dr. White and a second appointment at 10:30 a.m. related to an exam regarding chest pain with Dr. Smith. In addition, consistent with the unfulfilled orders database 71 shown in FIG. 8B, it will be assumed that Bruce Johnson has three unfulfilled orders including a full blood work-up, an EKG and a follow-up with Dr. Jones related to a skin rash.

Figure 13:
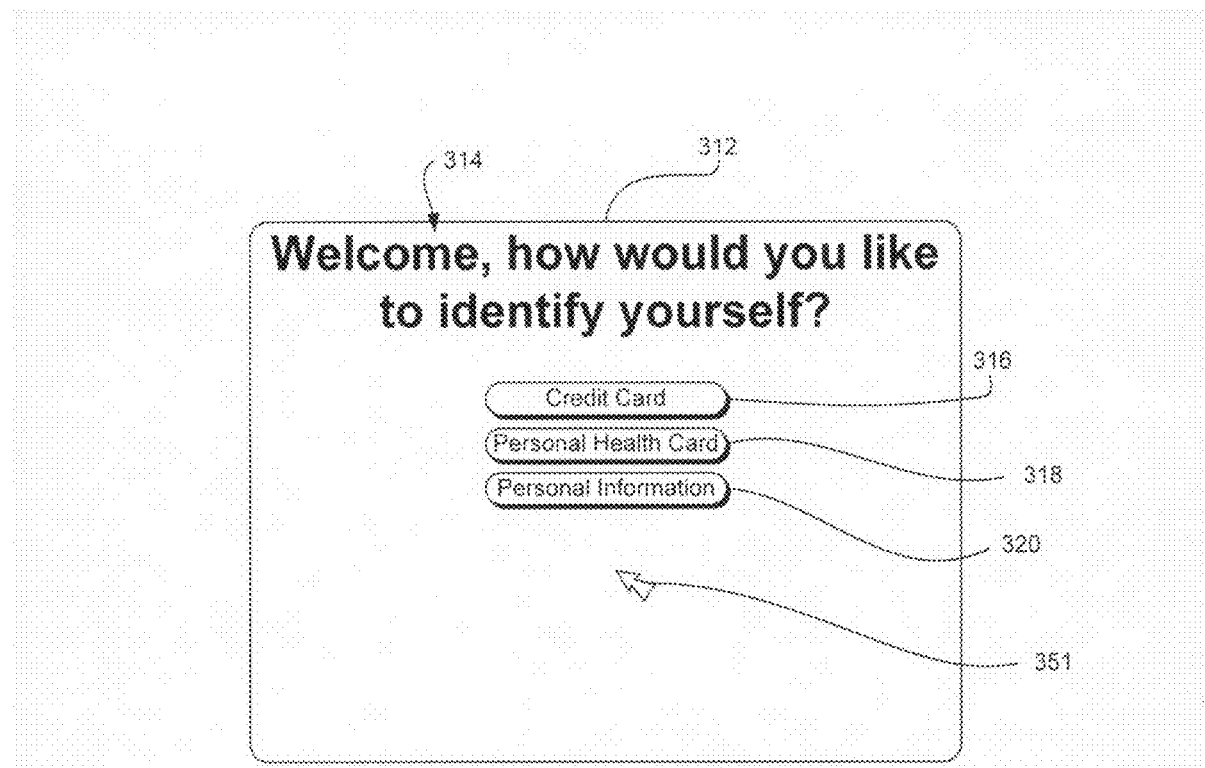
FIG. 13 is a screen shot that may be presented via one of the kiosks in FIG. 6 to welcome a patient and to direct the patient to take steps to identify himself.
Figure 14:
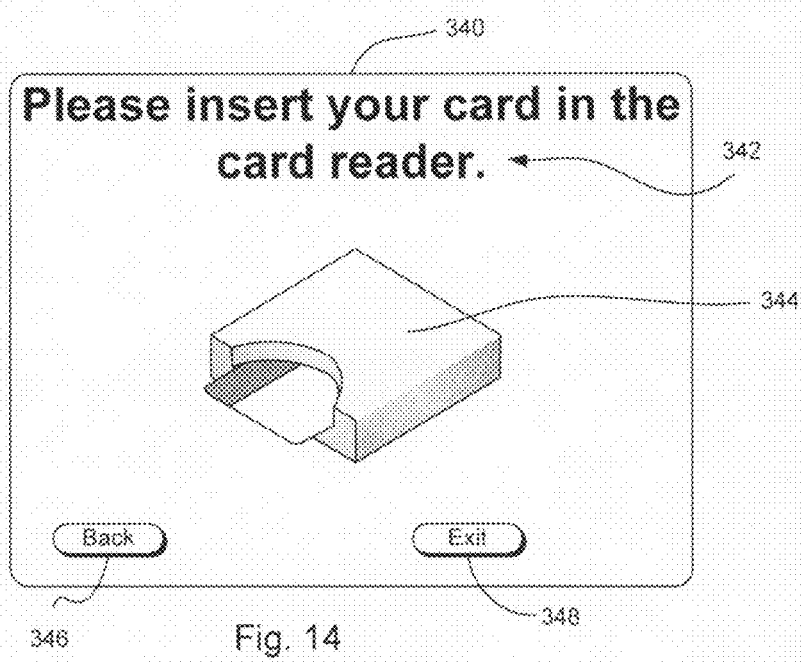
FIG. 14 is a screen shot that may be presented via one of the kiosks in FIG. 6 to guide a patient to insert a card into one of the card readers of FIG. 6.

Referring still to FIGS. 6 and 12 and also to FIG. 13, at block 204, when Mr. Johnson walks up to kiosk 26a to check-in for his two appointments, Mr. Johnson is greeted with a greeting screen shot 312 which includes instruction 314 near the top of the screen shot and three mouse selectable icons 316, 318 and 320 which can be selected by moving mouse controlled cursor 351 to a location over any one of the icons and clicking to select the icon via one of the mouse control buttons in a manner well known in the art. The instructions 314 instruct the patient to indicate, via the mouse selectable icons, how the patient would like to identify himself. The selectable icons include a CREDIT CARD icon 316, a PERSONAL HEALTH CARD icon 318 and PERSONAL INFORMATION icon 320. Where PERSONAL INFORMATION icon 320 is selected, the user may enter a user name and password in a manner like that described above to uniquely identify the patient before receiving any information about the patient's currently scheduled appointments or unfulfilled orders.

Where either of the card icons 316 or 318 is selected, Referring to FIG. 14, kiosk 26a provides a screen shot 340 with instructions 342 indicating that the patient should insert his card into the card reader 19. An image 344 of the card reader 19 may be provided to help the user visually identify the card reader. In addition to instructions 342 and image 344, screen shot 340 includes a BACK icon 346 and an EXIT icon 348. BACK icon 346 allows the patient to skip back to screen 312 shown in FIG. 13 to change the way the patient will identify himself. EXIT icon 348 generally allows the patient to exit the check-in procedure. BACK and EXIT icons are provided on all of the screen shots after screen shot 340 and operate in a similar fashion to allow a patient to back up through the screen shots or exit the check-in procedure.

Figure 15:
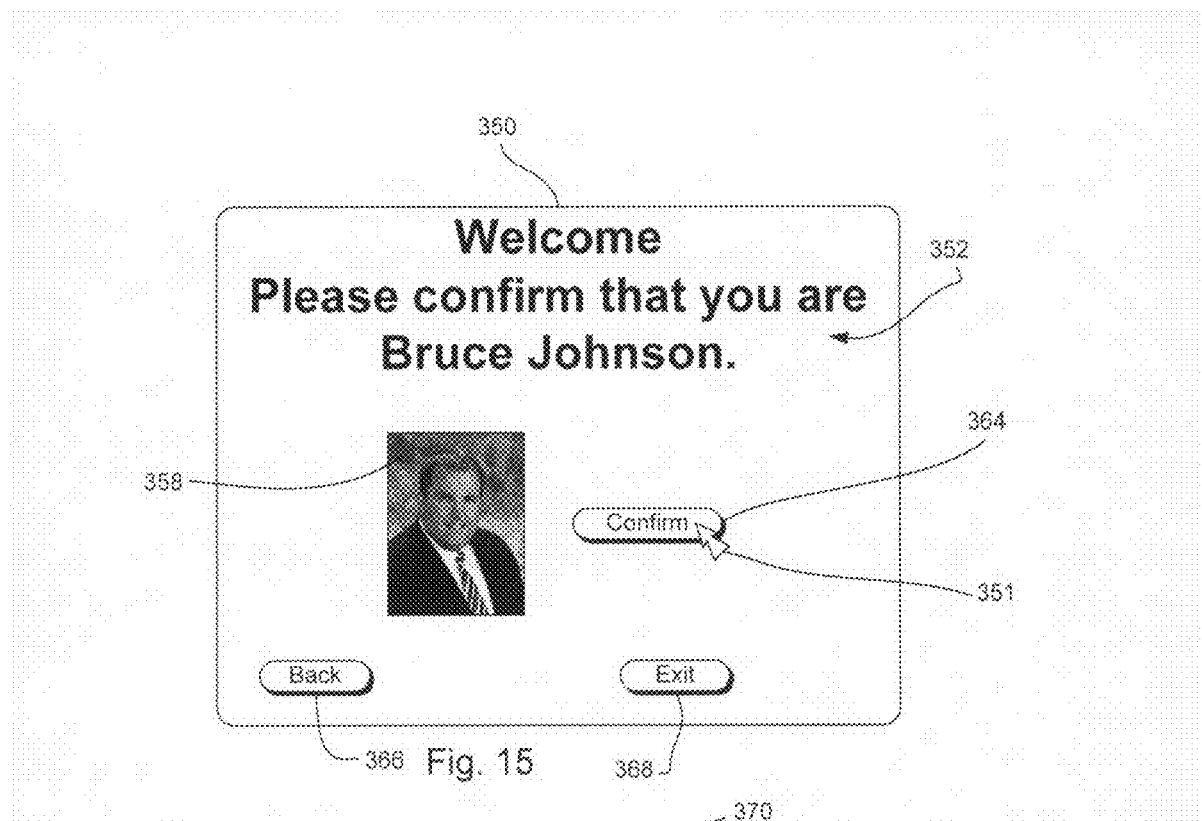
FIG. 15 is an exemplary kiosk screen shot inviting a patient to confirm that the system of FIG. 6 has identified the correct patient.

Referring still to FIGS. 6 and 12 and now also to FIG. 15, after the patient inserts his card into reader 19, at block 204 server 22a obtains patient identifying information from the card. Here, in FIG. 15, the server 22a queries the patient to make sure that the patient is in fact Bruce Johnson. To this end, a picture 358 of the patient stored in a facility database (e.g., in the patient's EMR) may be provided along with a mouse selectable CONFIRM icon 364 to confirm that the server 22a identified the correct patient via the patient's card. Once icon 346 is selected, kiosk 26a provides screen shot 370 that includes instructions 372 along with five separate mouse selectable icons that enable the patient to do various things via kiosk 26*a*. The exemplary icons include a CHECK-IN FOR APPOINTMENTS icon 374, a CHECK-IN FOR UNFULFILLED ORDERS (e.g., lab work) icon 376, an UP DATE PERSONAL INFORMATION icon 378, a FIND A FACILITY LOCATION icon 380 and a CHECK OUT AFTER APPOINTMENT icon 382. When icon 374 is selected, server 22*a* facilitates a check-in procedure. When icon 376 is selected, server 22*a* checks whether or not there are any unfulfilled orders for the patient and may list those orders along and provides tools for scheduling appointments for those orders. When icon 378 is selected, server 22*a* may step through a procedure that allow the patient to update his personal information stored by server 22*a*. When icon 380 is selected, server 22*a* may step through a way finder process to help the patient identify the location of some resource (e.g., a doctor's office, a clinic, an examination room, etc.) within the facility. When icon 382, is selected, kiosk 26*a* helps the patient step through a check out procedure.

Here, it will be assumed that Mr. Johnson has selected CHECK-IN FOR APPOINTMENTS icon 374. Once icon 374 is selected, server control passes to block 206 in FIG. 12. At block 206, referring again to FIG. 8A, server 22*a* accesses appointments database 69 and identifies currently scheduled appointments for the patient for the current day. At block 210, referring also to FIG. 8B, server 22*a* accesses unfulfilled orders database 75 and locates the unfulfilled orders for the patient. In the present example, three unfulfilled orders 83 are associated with Bruce Johnson 77 and therefore, at block 210, server 22*a* identifies each of the three unfulfilled orders. In addition, at block 210, server 22*a* attempts to identify a suggested appointment schedule that includes at least one time slot for one of the unfulfilled orders for Mr. Johnson and time slots for each of the currently scheduled activities or appointments.

At block 212, where server 22*a* is unable to identify a suggested appointment schedule including the currently scheduled appointments and at least one of the unfulfilled orders, control passes to block 230 where server 22*a* presents the currently scheduled appointments for Bruce Johnson so that the patient can check-in. In this regard, referring to FIG. 17, an exemplary screen shot that may be presented to the patient when server 22*a* is unable to identify a suggested appointment schedule is shown. Screen shot 390 includes each of the currently scheduled appointments for Bruce Johnson for the day including the follow up visit related to the hernia operation with Dr. White 392 and an examination regarding chest pain with Dr. Smith 394. In addition to listing the appointments, screen shot 390 includes separate CHECK-IN icons 396 and 398 for each of Bruce Johnson's appointments 392 and 394, respectively, that can be independently selected for checking in for the associated appointment. Moreover, screen shot 390 includes a CHECK-IN BOTH APPOINTMENTS NOW icon 400 that can be selected to check-in both the 8:30 a.m. and 10:30 a.m. appointments.

Figure 16:
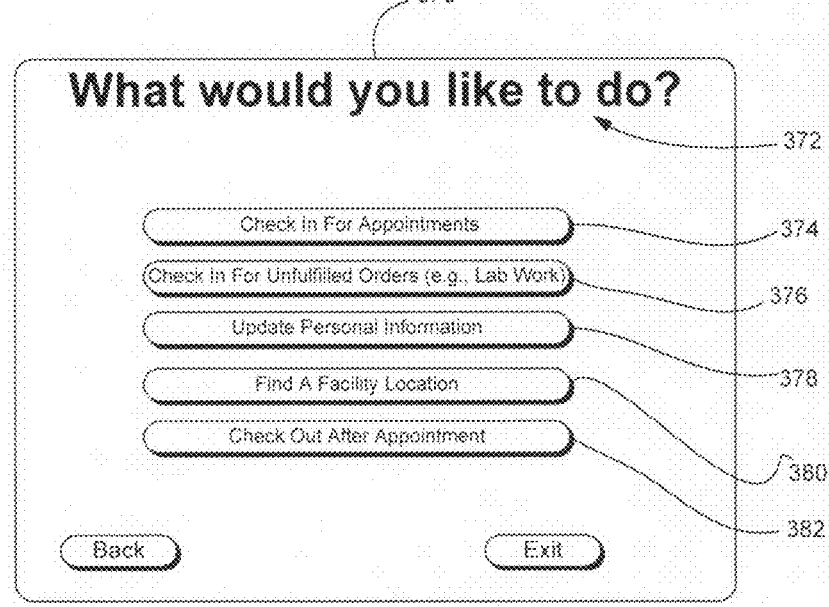
Figure 17:
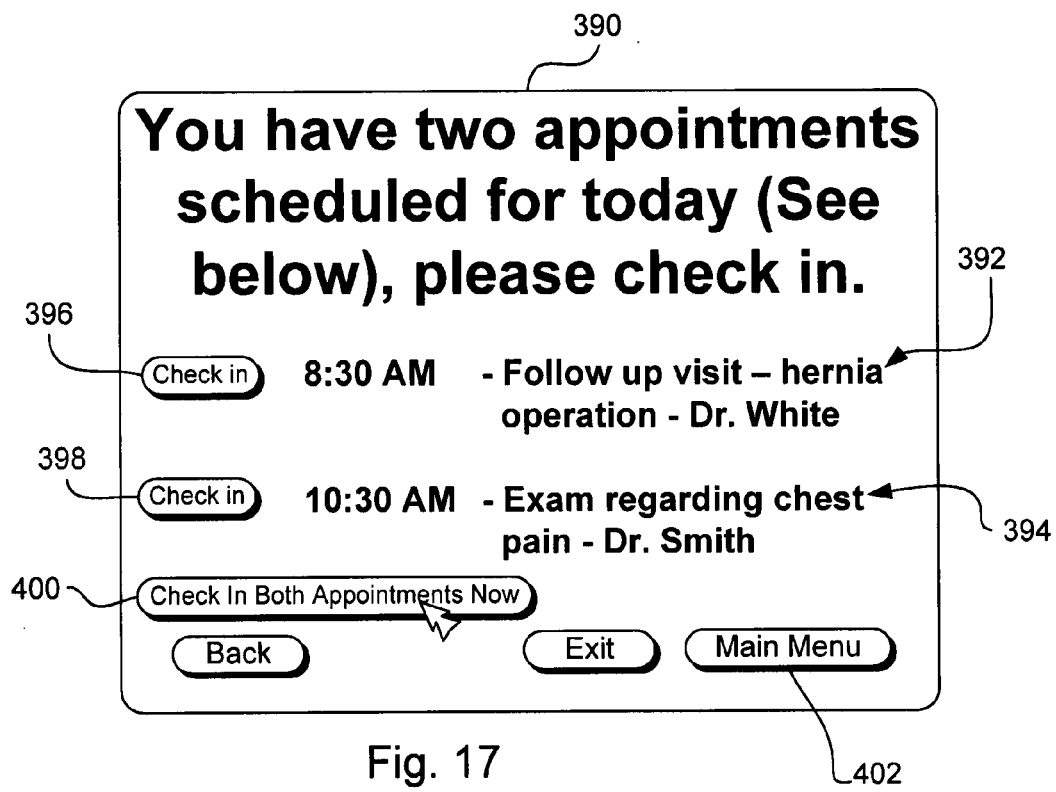
FIG. 17 is a kiosk screen shot which displays currently schedules appointments for a patient to allow the patient to check in for the appointments.
Figure 18:
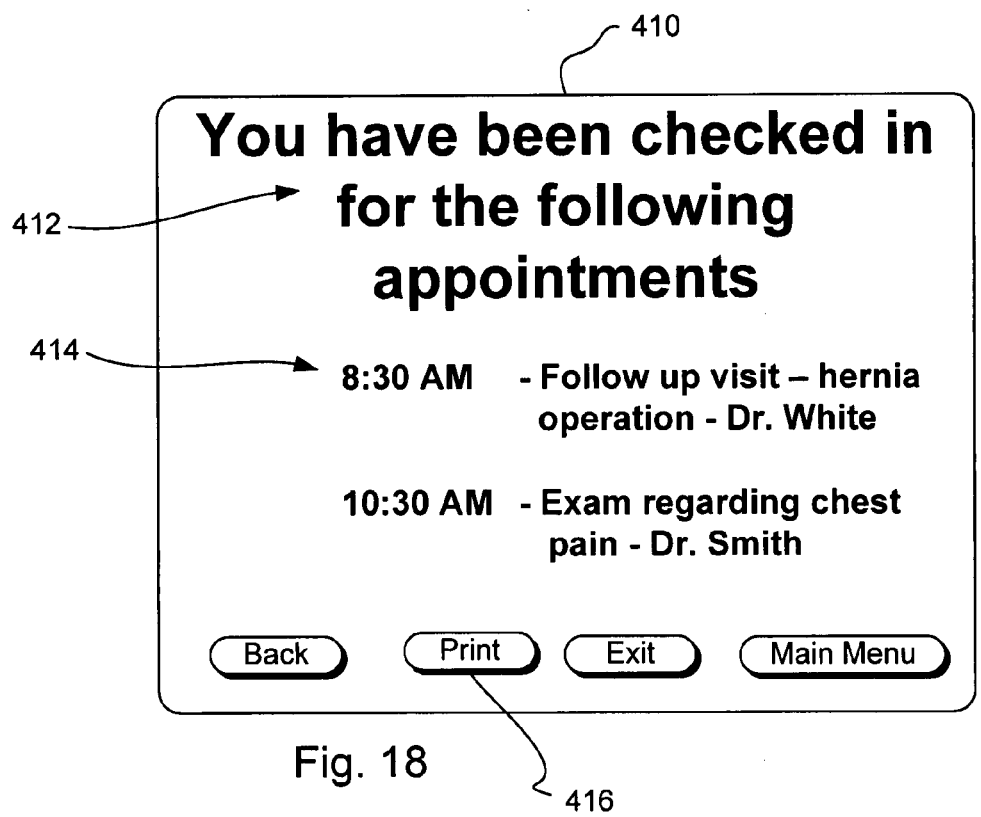
FIG. 18 is a kiosk screen shot that confirms that a patient has checked in for appointments.
Figure 19:
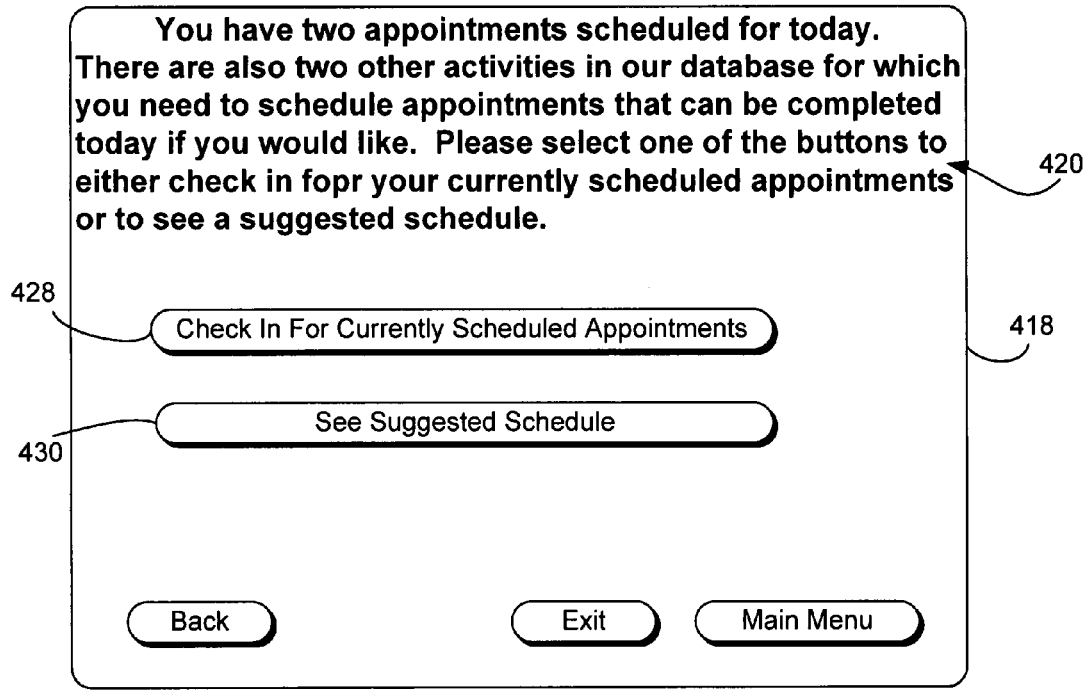
FIG. 19 is a kiosk screen shot that allows a patient to either check in for scheduled appointments or see a suggest appointment schedule that includes currently scheduled appointments as well as at least one unfulfilled order time slot.

In FIG. 17, a MAIN MENU icon 402 is also provided that, when selected, takes the patient back to the screen shot shown in FIG. 16 where the patient can select any of several different icons to facilitate different activities. Many of the screen shots described hereafter include a MAIN MENU icon 402 and, in each case, when the MAIN MENU icon is selected, the patient is taken back to the screen shot shown in FIG. 16.

Referring still to FIGS. 6, 12 and 17, at block 218, when the patient selects icon 400 to check-in both appointments or selects one of the CHECK-IN icons 396 or 398, control passes to block 222 where server 22*a* stores an indication that the patient has checked in for both appointments and may provide notice to a receptionist, nurse, physician, etc. that the patient is present and waiting. In addition, to confirm that check-in has been completed, server 22*a* generates screen shot 410 shown in FIG. 18 which includes confirming language 412 indicating that the patient has been checked in along with specific information 414 regarding the checked in appointment. Screen shot 410 includes a PRINT icon 416 that, when selected, causes a confirmation sheet to be printed out via printer 17 (see again FIG. 6) confirming that check-in has been completed and providing the patient's schedule for the day. Referring once again to block 218 in FIG. 12, if the patient opts not to check-in for the appointments the process ends.

Referring still to FIGS. 6 and 12, and specifically to decision block 212, when server 22*a* identifies at least one suggest appointment schedule including at least one time slot for an unfulfilled order and time slots for the currently scheduled activities, control passes to block 220 where server 22*a* presents the currently scheduled appointments and the option to schedule unfulfilled orders. In this regard, see FIG. 19 which illustrates an exemplary screen shot 418 including instructions 420, a CHECK-IN FOR CURRENTLY SCHEDULED APPOINTMENTS icon 428 and a SEE SUGGESTED SCHEDULE icon 430.

Referring also to FIG. 8B, while the unfulfilled orders database 71 is shown to include three unfulfilled orders 83 for Mr. Johnson 77, in the present example it will be assumed that only two of the three unfulfilled orders for Mr. Johnson can be scheduled along with Mr. Johnson's currently scheduled hernia follow up appointment and chest pain examination appointment. More specifically, here it is assumed that Mr. Johnson's unfulfilled order for a follow up appointment with Dr. Jones related to a skin rash cannot be scheduled with the currently scheduled appointments either because available time slots for the follow up appointment do not exist or the time slots that are available would conflict with the currently scheduled appointments for the patient. Thus, because two unfulfilled orders that may be scheduled with the currently scheduled appointments are stored in the unfulfilled orders database 71, instructions 420 indicate that there are two activities in the database that need to be scheduled that may be completed during the current day and requests that the patient select one of icons 428 or 430 to either check-in for currently scheduled appointments or to see a suggested schedule including the two unfulfilled orders that can be scheduled for the current day, respectively.

When icon 428 is selected to indicate that the patient would like to check-in for the currently scheduled appointments, control passes to block 230 where appointment check-in is facilitated as described above. When icon 430 is selected to see the suggested schedule including unfulfilled orders and currently scheduled appointments, control passes from block 224 to block 226 where the suggested appointment schedule is presented.

Figure 20:
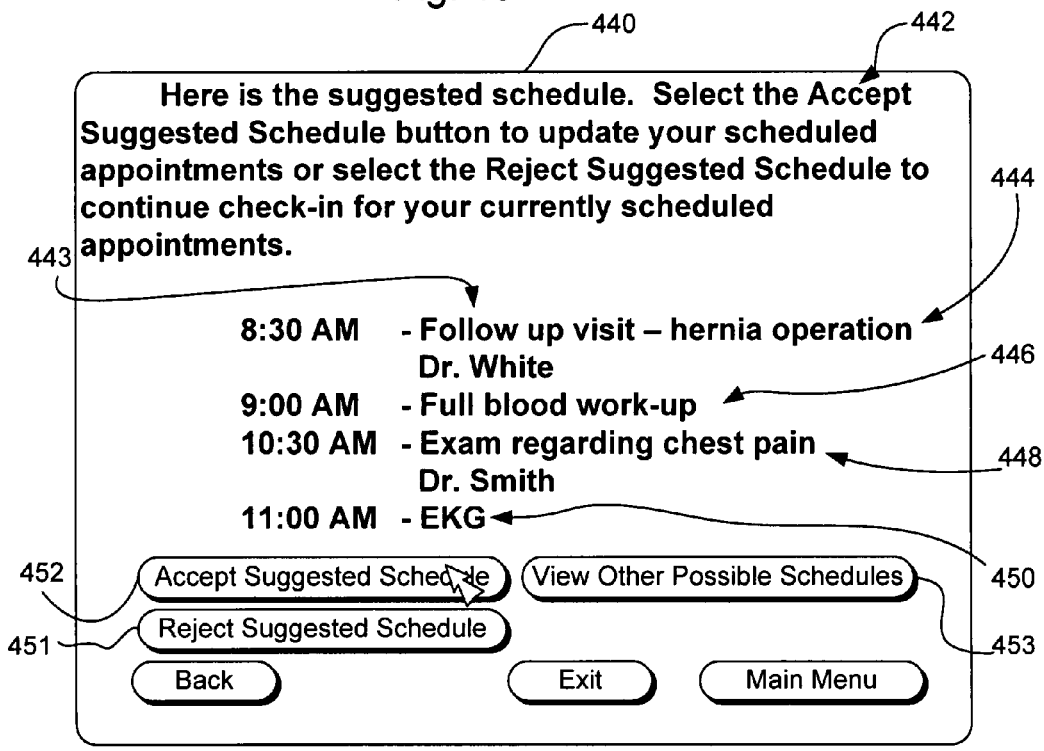
FIG. 20 is a kiosk screen shot that presents a suggested appointment schedule to a patient.

Referring now to FIG. 20, an exemplary screen shot 440 for presenting the suggested schedule is illustrated that includes instructions 442, a list 443 of current appointments and unfulfilled orders that can be scheduled, an ACCEPT SUGGESTED SCHEDULE icon 452, a REJECT SUGGESTED SCHEDULE icon 451 and a VIEW OTHER POSSIBLE SCHEDULES icon 453. List 443 includes the currently scheduled appointments at 8:30 a.m. and 10:30 a.m. for the hernia follow up visit with Dr. White and the chest pain exam with Dr. Smith 444 and 448, respectively, as well as the unscheduled unfulfilled orders 446 and 450 related to the full blood work up and EKG which are tentatively slotted for 9 and 11 a.m. time slots as shown. The instructions 442 instruct the patient to accept one of the icons 452, 451 or 453. Where the VIEW OTHER POSSIBLE SCHEDULES icon 453 is selected, as the label suggests, the server 22*a* (see again FIG. 6) presents a second suggested schedule. Here, where there is no second suggested schedule, icon 453 would not be presented. Thus, server 22*a*, in at least some embodiments, is programmed to identify if scheduling options exist and, only where options exist, to present those options to patients.

Referring still to FIGS. 12 and 20, where REJECT SUGGESTED SCHEDULE icon 451 is selected, control passes from block 227 back up to block 230 where a screen shot akin to screen shot 390 in FIG. 17 is provided to allow the patient to check-in for the currently scheduled appointments.

Figure 21:
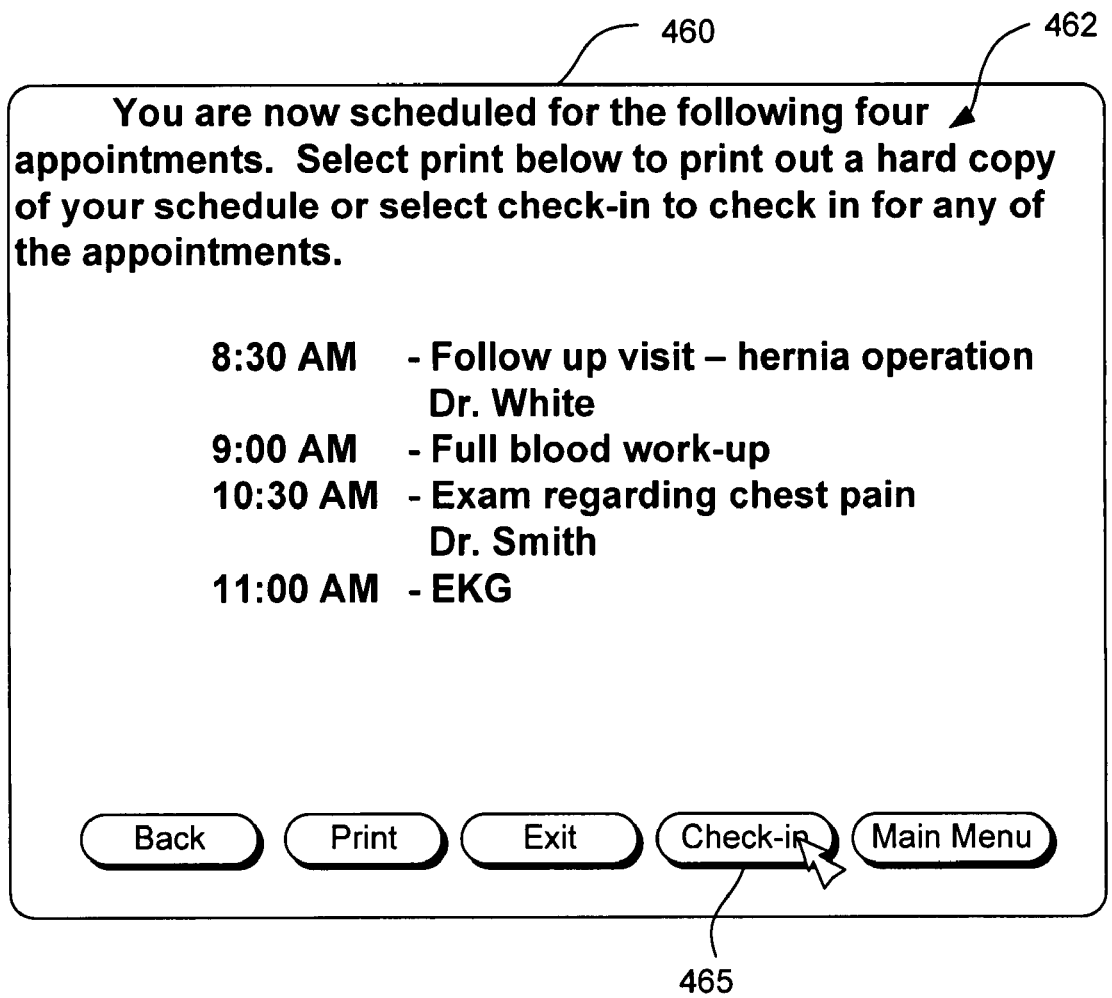
FIG. 21 is a kiosk screen shot that confirms that a patient has updated the patient schedule in a manner consistent with the schedule suggested via the screen show shown in FIG. 20.

Referring to FIGS. 6, 12 and 20, where the patient selects ACCEPT SUGGESTED SCHEDULE icon 452, control passes from block 227 to block 228 where server 22*a* stores the suggested schedule as the currently scheduled appointments. In addition, as seen in FIG. 21, when icon 451 is selected, server 22*a* provides a confirmation screen shot 460 including confirmation language 462 and information that specifies the accepted suggested schedule. Screen shot 460 also includes a CHECK-IN icon 465 that can be selected to check-in any of the appointments listed via screen shot 460. Here, it is contemplated that, if a patient selects CHECK-IN icon 465, a screen shot similar to the FIG. 17 screen shot 390 would be provided to facilitate check-in, albeit where the screen shot lists all four appointments shown in FIG. 21 instead of the original two shown in FIG. 17.

The example above includes a server 22*a* that attempts to schedule unfulfilled orders around currently scheduled appointments. In at least some embodiments it is contemplated that where unfulfilled orders cannot be scheduled around currently scheduled appointments, server 22*a* may be programmed to determine if currently scheduled appointments can be modified to accommodate one or more existing appointments and if so, may present a suggested schedule including currently scheduled appointments that have been shifted to different time slots and at least one unfulfilled order.

Figure 22:
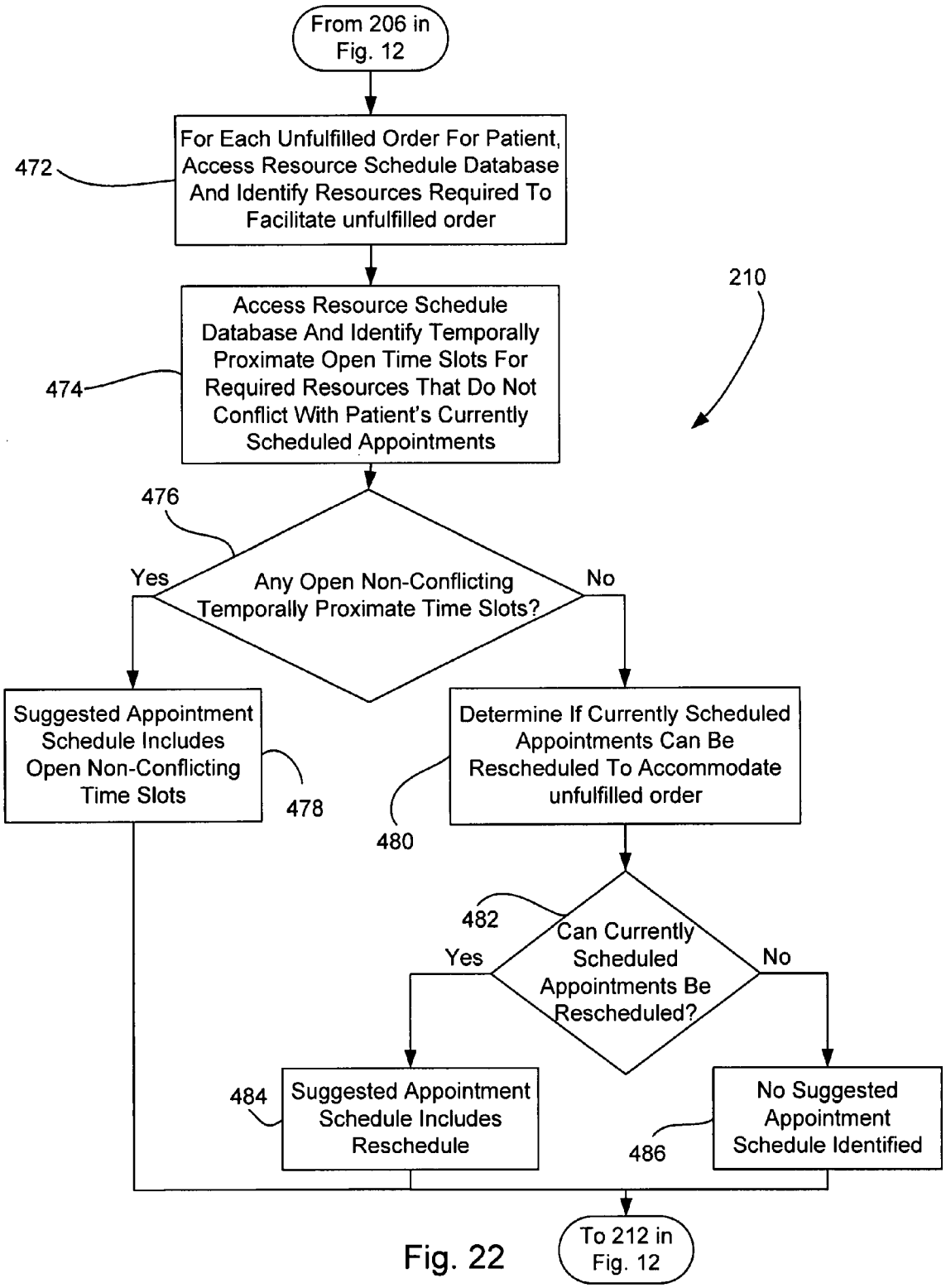
FIG. 22 is a sub-process that may comprise one of the process blocks shown in FIG. 12.

Referring to FIG. 12 and also to FIG. 22, an exemplary sub-process 210 for identifying a suggest appointment schedule that may comprise block 210 in FIG. 12 is shown in FIG. 22. Referring also to FIGS. 6 and 7, after server 22*a* identifies currently scheduled appointments for the current day, control may pass to block 472 where server 22*a*, for each unfulfilled order for a patient in database 71 (see again FIG. 8B), accesses the resource schedule database 31 to identify resources required to facilitate the unfulfilled orders for the patient. To this end, server 22*a* identifies each unfulfilled order corresponding to a patient in the activity column 37 of database 33 and associated required resources in column 39 for the activity in column 37. Thus, for instance, in the present example where unfulfilled orders for Mr. Johnson in database 71 include an EKG, server 22*a* identifies the resources 47 corresponding to the EKG activity 43 in database 33 at block 472.

Continuing, at block 474, server 22*a* identifies temporally proximate open time slots for the identified required resources that do not conflict with the patient's currently scheduled appointments by accessing the resource/schedule database 35, identifying each resource required in column 49 and then checking the schedule corresponding to the resource to determine whether or not the resource is available. Here, the phrase "temporally proximate" may be defined differently depending on circumstances. For example, temporally proximate may mean within one hour of the beginning or end time of a previous or next consecutive currently scheduled appointment or may include any time slot between two other time slots that occur on the current day. At decision block 476, where at least one open nonconflicting temporally proximate time slot exists, control passes to block 478 where server 22*a* generates a suggested appointment schedule that includes the open nonconflicting time slots after which control passes back to block 212 in FIG. 6.

Referring still to FIGS. 6 and 22, at block 476, when no nonconflicting temporally proximate time slots have been identified, control passes to block 480 where, in at least some embodiments, server 22*a* determines whether or not the currently scheduled appointments can be rescheduled to accommodate at least one unfulfilled order. For example, in the present case it may be that the only time that a EKG can be performed on the current day for Bruce Johnson is at 8:30 a.m. which would be in direct conflict with Bruce Johnson's currently scheduled follow up visit with Dr. White. However, it may be that Dr. White has a time slot open for 11 a.m. on the current day in which case, by shifting the current hernia operation follow up appointment to 11 a.m., the 8:30 a.m. time slot could be opened up for the EKG. Where currently scheduled appointments can be reshuffled to accommodate unfulfilled orders, control passes to block 484 where server 22*a* generates a suggested appointment schedule that includes the rescheduled appointment(s) as well as the unfulfilled order(s) that can be accommodated. After block 484 control passes back to block 212 in FIG. 6.

Referring still to FIG. 22, at block 482, if currently scheduled appointments cannot be rescheduled to accommodate at least one unfulfilled order, control passes to block 486 where server 22*a* stores an indicator that no suggested appointment schedule was identified after which control passes to block 212 in FIG. 6.

The check-in/scheduling example above assumes that the only constraint on scheduling unfulfilled orders and shifting currently scheduled appointments is whether or not time slots are open and resources are available. In at least some embodiments it is contemplated that other scheduling constraints may be considered by server 22*a*. For instance, for certain tests and procedures it may be required that a patient fast for 12 hours prior to the test or procedure. In this case, if an unfulfilled order is associated with a test or procedure that requires 12 hours of fasting, the unfulfilled orders database 71 in FIG. 8B may include information specifying the 12 hours fast limitation which can be used by server 22*a* when determining whether or not to present the unfulfilled order as part of a suggest appointment schedule. Similarly, the appointment database 69 (see FIG. 8A) may include additional constraints that need to be considered either prior to shifting a currently scheduled appointment or that limit unfulfilled order from being scheduled temporally proximate the appointments.

In addition, in at least some embodiments, server 22*a* may be programmed to consider information in addition to unfulfilled orders, currently scheduled appointments and resource availability when attempting to identify a suggested appointment schedule. For instance, where server 22*a* is programmed to know anticipated travel times between the locations of different facility resources, server 22*a* may be programmed to take travel times into consideration when attempting to identify suggested schedules. Similarly, where patients typically need some time to recover from a specific type of procedure or test, server 22*a* may be programmed to account for an anticipated recovery period.

In addition to or instead of identifying unfulfilled orders and potentially suggesting scheduling of those orders when a patient checks in to a medical facility, the system 10*a* shown in FIG. 6 may identify opportunistic scheduling activities or routine best practices activities for patients upon check-in and suggest scheduling of those opportunistic activities. Here, an "opportunistic activity" is any medical activity that it would be advisable the patient participate in. Here, opportunistic activities may not include unfulfilled orders by physicians and instead simply include activities, often elective, that may make sense given a patient circumstances. For example, it may be that it is standard medical best practice for all male patients over 50 years of age to have a yearly colonoscopy. Similarly, it may be that for all patients over 50 years of age, regardless of gender, it is standard medical practice for the patients to have a full physical. Here, while the colonoscopy or physical may not be ordered by a physician, patients may nevertheless want to participate in those activities on a yearly basis as part of an overall health regimen.

Figure 10:
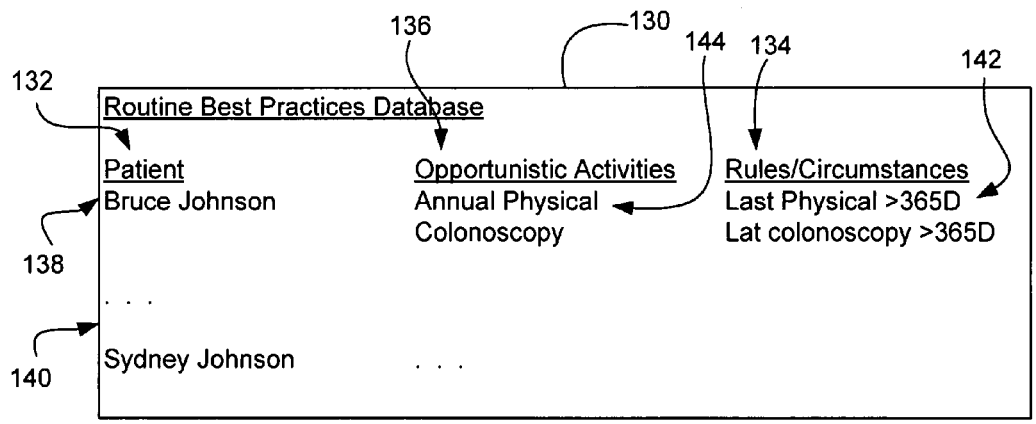
FIG. 10 is a schematic diagram illustrating one example of the routine best practices database of FIG. 6.

Referring once again to FIG. 6 and also now to FIG. 10, best practices database 130 codifies various opportunistic scheduling activities and, to that end, includes a patient column 132, a rules/circumstances column 134 and an opportunistic activities column 136. Patient column 132 lists facility clients and, to that end, exemplary clients Bruce Johnson 138 and Sidney Johnson 140 are listed in column 132. In column 136, opportunistic activities associated with each one of the patients in column 132 are listed. Exemplary opportunistic activities for Mr. Johnson include an annual physical and a colonoscopy collectively identified by numeral 144.

Rules/circumstances column 134 includes a separate rule or a plurality of rules for each one of the opportunistic activities in column 136 which indicates when the opportunistic activity should be suggested to an associated patient. For example, exemplary rules 142 corresponding to the annual physical and colonoscopy activities in column 136 require greater than 365 days since the last physical or colonoscopy for the patient. For each patient the opportunistic activities may be generated by server 22a automatically as a function of the rules in column 134 or in some cases, a subset or all of the opportunistic activities may be specified manually by a facility employee.

Figure 23:
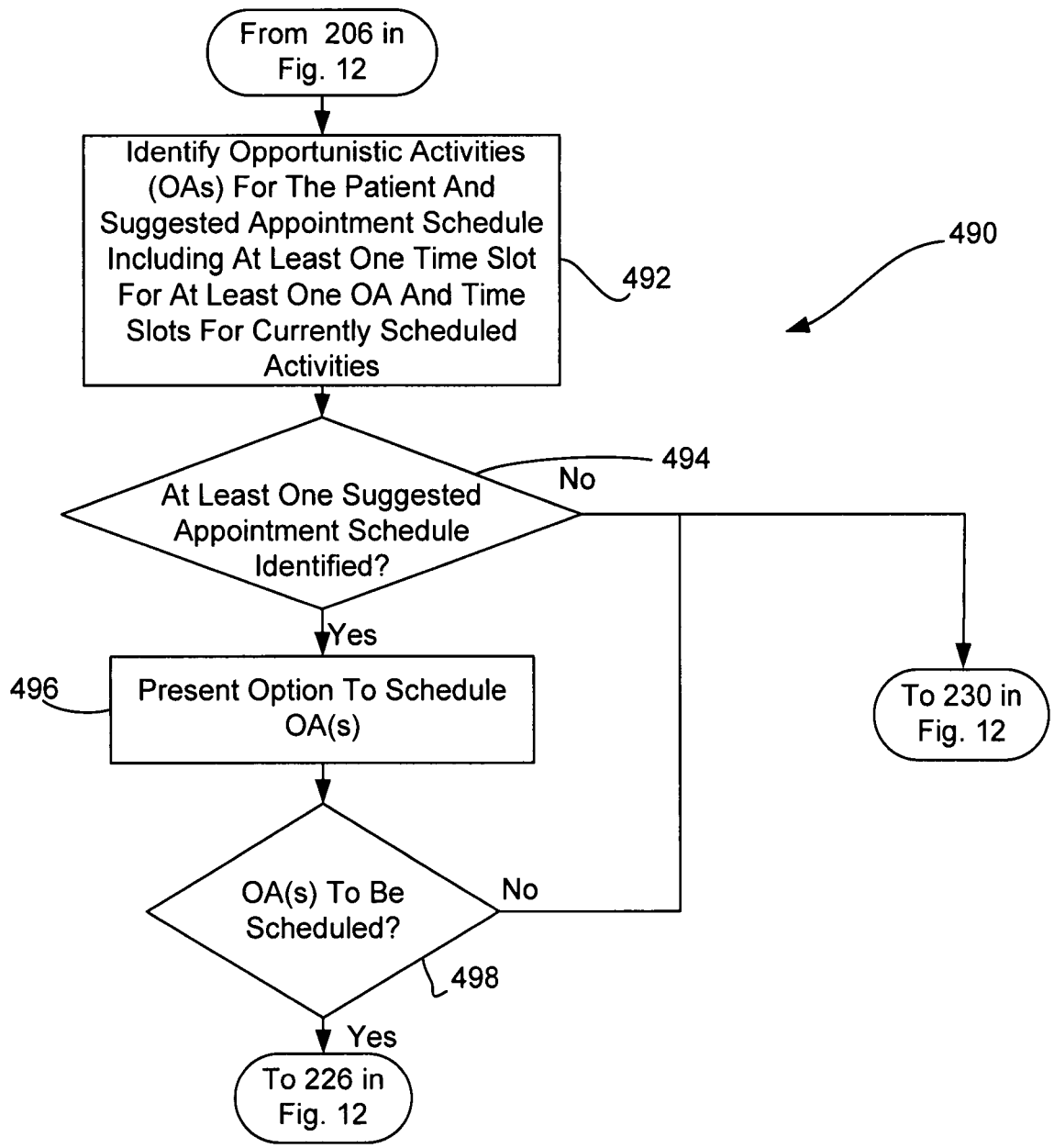

Referring now to FIG. 23, an exemplary sub-process 490 that may be substituted for blocks or steps 210, 212, 220 and 224 in FIG. 12 is illustrated for suggesting and facilitating scheduling of opportunistic activities. Referring also to FIGS. 6 and 10, after server 22a identifies currently scheduled appointments for a patient at block 206, control may pass to block 492. At block 492, server 22a accesses the best practices database 130 and identifies opportunistic activities for the patient where rules/circumstances associated with the activities have been met (i.e., current patient circumstances match the circumstances associated with the rule). In addition, at block 492, server 22a may access the resource schedule database 31 (see again FIG. 7) to identify resources required for the opportunistic activities for the patient and time slots during which those resources are available to perform the activities. Here, as above, when at least one time slot is available for completing an opportunistic activity where the time slot either fits into the patient's currently scheduled appointments or can be accommodated by shifting scheduled appointments, server 22a identifies a suggested appointment schedule. At block 494, when server 22a is unable to identify a suggested appointment schedule, control passed back to block 230 in FIG. 12 where normal appointment check-in occurs as described above. When server 22a identifies at least one suggested appointment schedule at block 494, control passes to block 496 where the option to schedule opportunistic activities is presented.

Figure 24:
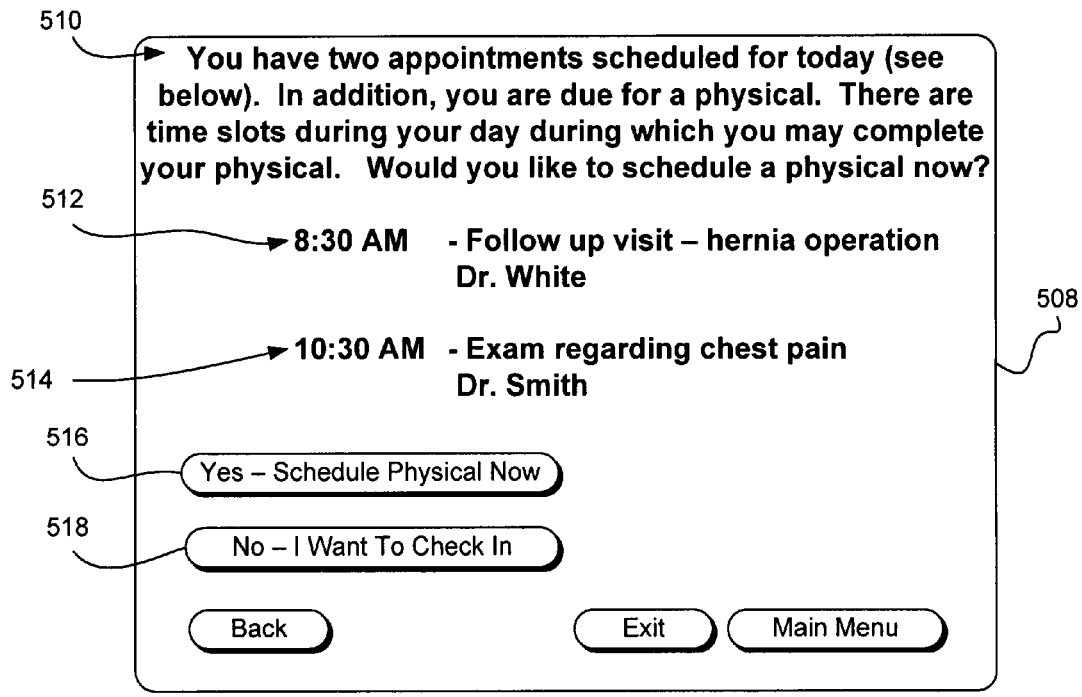
FIG. 24 is a kiosk screen shot that allows a patient to either check in for currently scheduled appointments or schedule a routine physical.

Referring now to FIG. 24, an exemplary screen shot 508 that may be presented via kiosk 26a to indicate that an opportunistic scheduling activity exists is shown. Screen shot 508 includes instructions 510, a list of currently scheduled appointments including appointment 512 and 514, a YES—SCHEDULE PHYSICAL NOW icon 516 and a NO—I WANT TO CHECK-IN icon 518. Here, instructions 510 indicate that the server 22a has identified at least one time slot that does not conflict with the patient's currently scheduled appointments during which a physical that is due can be completed. In the present example, referring also to FIG. 10, it is assumed that despite the fact that Bruce Johnson (i.e., the patient in the present example) is also due for a colonoscopy, server 22a was unable to identify an open and nonconflicting time slot during the patients day to accommodate that procedure and therefore the suggested appointment schedule reflected in screenshot 508 does not suggest scheduling the colonoscopy for the current day.

Figure 25:
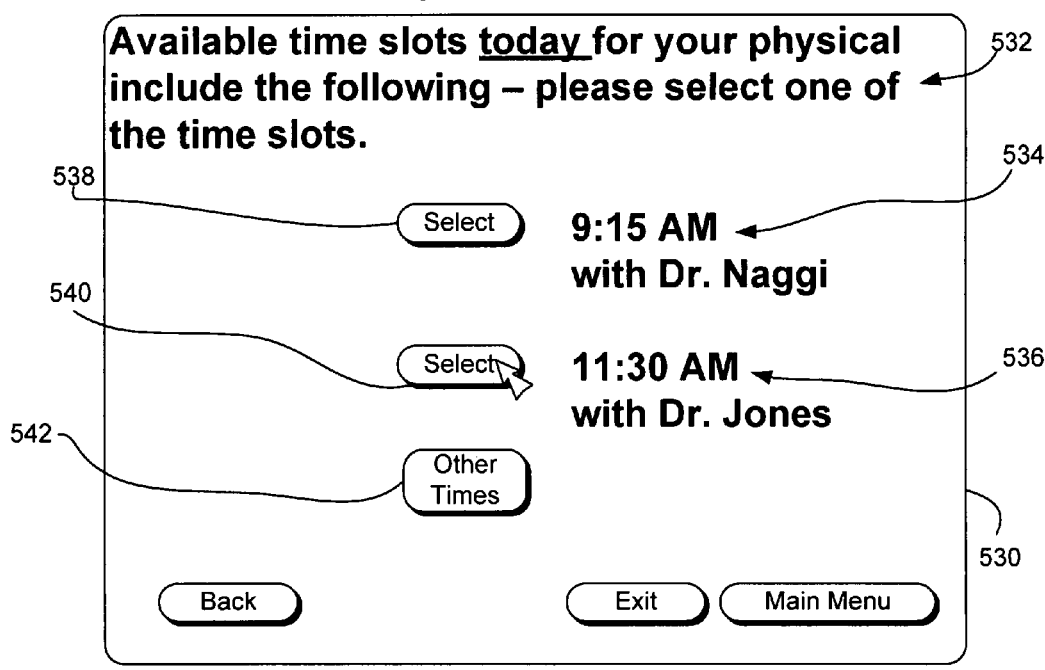
FIG. 25 is a kiosk screen shot that presents possible appointment times for a physical.

Referring still to FIGS. 6, 23 and 24, when a patient selects icon 518 at block 498 to reject scheduling the physical, control passes back to block to 230 in FIG. 12 where the check-in process continues. When the patient selects icon 516 at block 498, control passes to block 226 in FIG. 12 where the suggested appointment schedule is presented by server 22a. Referring to FIG. 25, an exemplary screen shot 530 which represents a second way to present a suggested appointment schedule is shown. Here, instead of listing currently scheduled appointments as well as opportunistic activities that may be scheduled, multiple times for scheduling one opportunistic activity are shown. In this case, screenshot 530 includes instructions 532, two separate times 9:15 a.m. and 11:30 a.m. for appointments for physicals with Dr. Naggi and Dr. Jones shown at 534 and 536, respectively, SELECT icons 538 and 540 corresponding to possible appointments 534 and 536, respectively, and OTHER TIMES icon 542. Here, where a patient selects one of icons 538 or 540, the appointment 534 or 536 associated therewith is indicated to server 22a. Where neither of the suggested appointments 534 and 536 is optimal for a patient, patient may select OTHER TIMES icon 542 to identify other time slots during which the physical may be completed.

Here, it will be assumed that the patient selects the 11:30 a.m. appointment with Dr. Jones 536 which causes server 22a to add that appointment to the currently scheduled appointment list in database 69. After an appointment is added to the currently scheduled list, control passes back up to block 320 in FIG. 12 where the currently scheduled appointments, including the appointment associated with the opportunistic activity, are presented for check-in.

In addition to or instead of identifying unfulfilled orders and opportunistic activities to be suggested to patients upon check-in for possible scheduling, in at least some embodiments it is contemplated that there may be prerequisite requirements that have to be met prior to allowing a patient to check-in for particular types of appointments. For example, it may be standard medical practice for a EKG to be performed prior to an appointment with a physician regarding chest pain. Here, when a patient checks in, sever 22a (see again FIG. 6) may be programmed to identify prerequisites for currently scheduled appointments and to require that those prerequisites be performed prior to check-in being completed or at least that the prerequisites be scheduled for times prior to appointments to be checked in.

Figure 9:
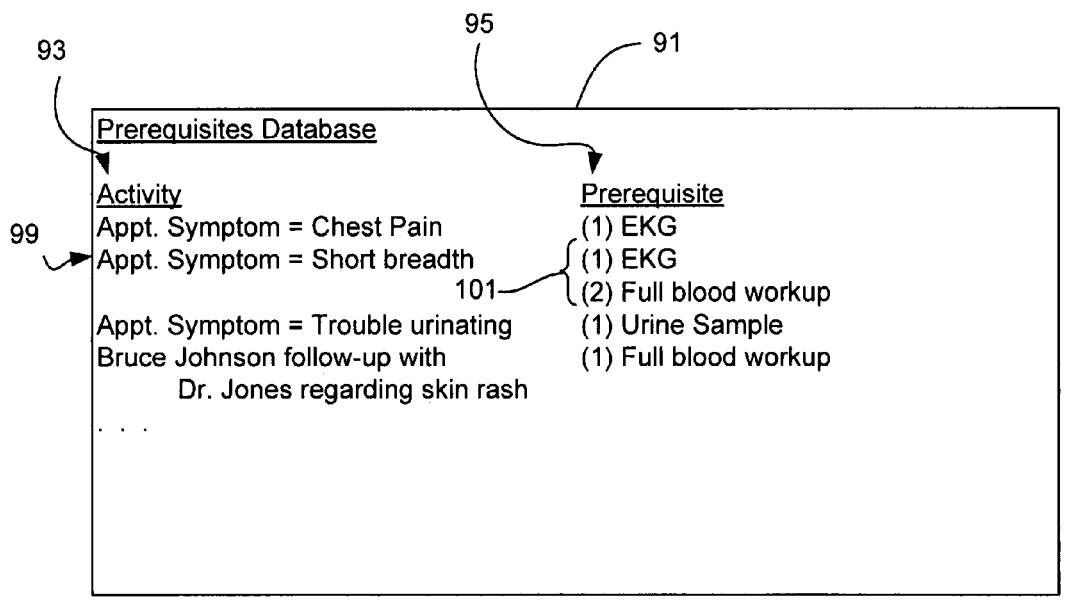
FIG. 9 is a schematic diagram illustrating one example of the prerequisites database of FIG. 6.

Referring again to FIG. 6 and also now to FIG. 9, an exemplary prerequisites database 91 is shown in FIG. 9 that includes an activity column 93 and a prerequisite column 95. Activity column 93 lists various activities that may be facilitated at a facility while prerequisite column 95 lists a subset of prerequisite for each of the activities in column 93 where the subset of prerequisites include other activities that need to be performed or at least scheduled to occur prior to check-in for one of the activities in column 93. Thus, one of the activities in column 93 is an appointment for chest pain and a prerequisite in column 95 corresponding to the appointment for chest pain is that an EKG be performed. Similarly, an appointment for shortness of breath 99 in column 93 corresponds to two prerequisites 101 in column 95 including an EKG and a full blood work up. While database 91 is simplified for the purposes of explaining this invention, it should be appreciated that database 91 would be extremely complex and include many hundreds if not thousands of different activities that occur at a facility and associated prerequisites.

Figure 26:
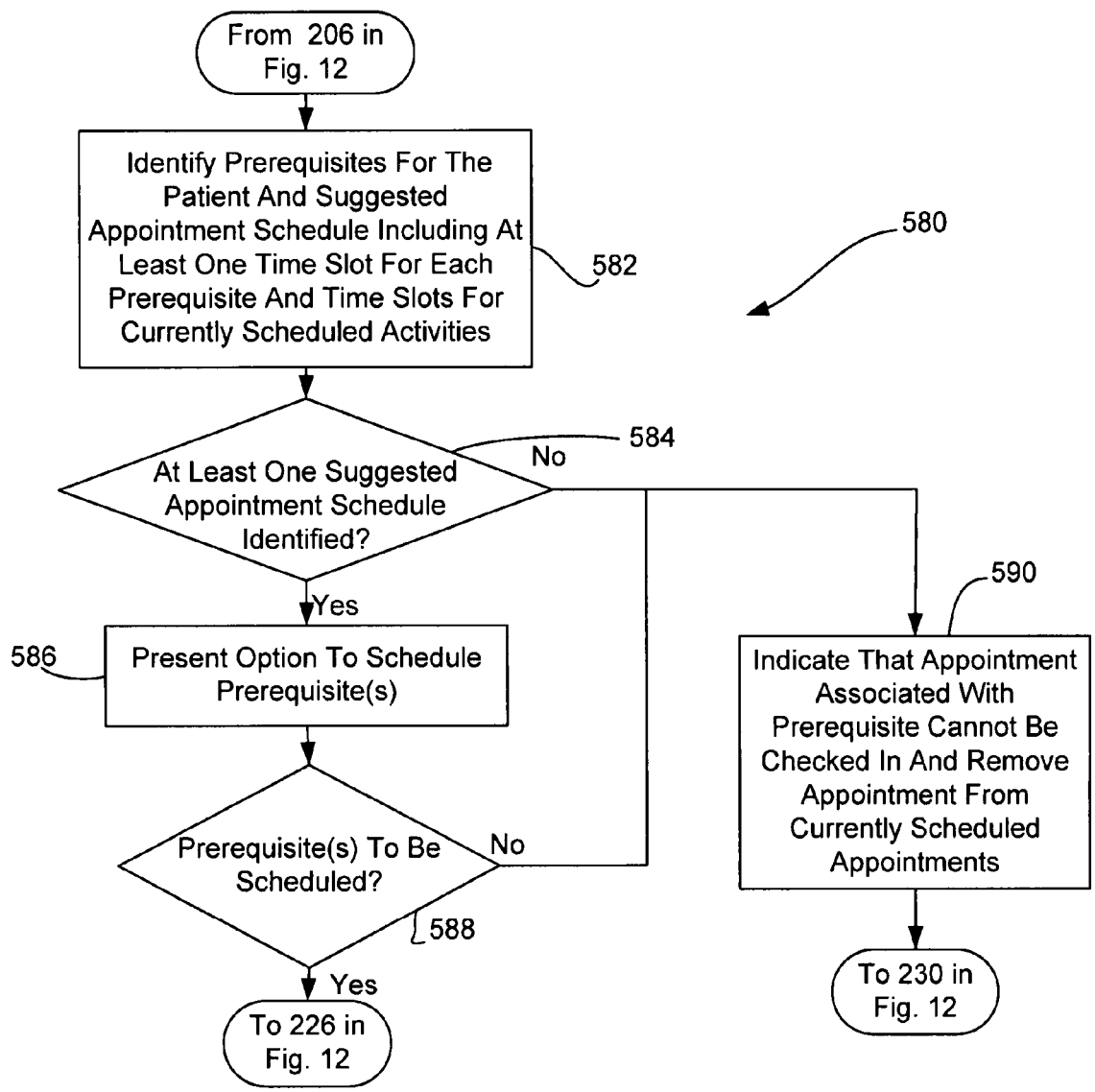
FIG. 26 is a flow chart that may be substituted for a portion of the flow chart shown in FIG. 12 for identifying prerequisites to currently scheduled appointments when a patient checks in and to facilitate scheduling of those prerequisites.

Referring to FIG. 26, an exemplary sub-process 580 that may be substituted for blocks 210, 212, 220 and 224 is illustrated wherein the sub-process is provided for identifying prerequisites for appointments, indicating prerequisites to a patient upon check-in and requiring the patient to schedule prerequisites prior to check-in. Referring also to FIGS. 6, 9 and 12, after currently scheduled appointments have been identified by server 22a at block 206, control may pass to block 582 in FIG. 26. At block 582, server 22a accesses prerequisites database 91 and identifies prerequisites in column 95 for each of the activities (e.g., appointments) in column 93. In addition, at block 582, server 22a may access resource schedule database 31, identify resources required to facilitate the prerequisite activities, identify open time slots for each of the required resources and compare the open time slots to the patient's appointments to identify a suggested appointment schedule including at least one time slot for each prerequisite where the identified time slots do not conflict with the currently scheduled appointment time slots or where the appointments can be shifted to other time slots to accommodate the prerequisites.

At block 584, when server 22a is unable to identify at least one suggested appointment schedule, control passes to block 590 where kiosk 26a is used to indicate that the appointment associated with the prerequisite that could not be scheduled cannot be checked. Server 22a removes appointments from the currently scheduled appointments when appointment prerequisites cannot be met. Although not illustrated, at this point, it may be that server 22a refers patients to a facility receptionist for further processing when prerequisites cannot be met. In the alternative, server 22a may be programmed to identify time slots on subsequent days for the canceled appointment and preceding prerequisite appointments and may allow the patient to schedule those appointments via kiosk 26a.

After block 590, control passes back to block 230 in FIG. 12 where check-in for appointments that have not been canceled continues.

Referring still to FIGS. 6 and 26, at block 584, when server 22a identifies at least one suggested appointment schedule, control passes to block 586 where the option to schedule prerequisites is presented via kiosk 26a.

Figure 27:
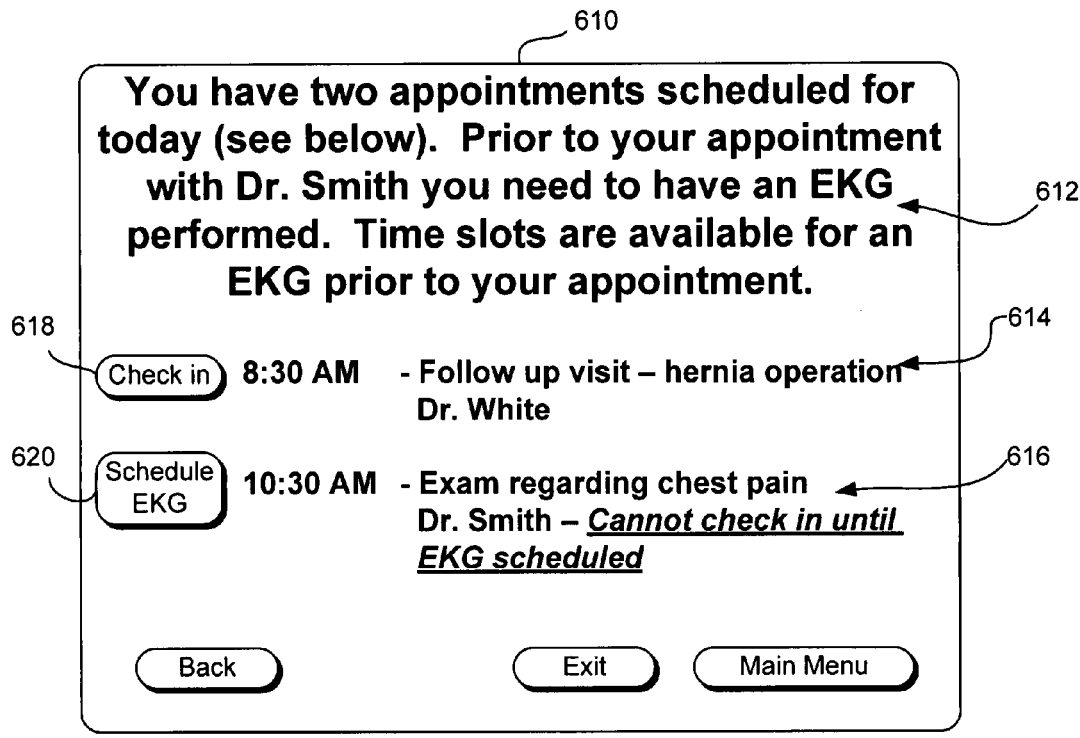
FIG. 27 is a kiosk screen shot which indicates that a patient must schedule a prerequisite activity prior to checking in for a currently scheduled appointment.

Referring now to FIG. 27, an exemplary screen shot 610 for presenting an option to schedule prerequisites is shown. Screen shot 610 includes instructions 612, information 614 that identifies a follow up visit for hernia operation with Dr. White where no prerequisite was required, information identifying an exam related to chest pain with Dr. Smith, a CHECK-IN icon 618 associated with the first appointment information 614 and a SCHEDULE EKG icon 620 associated with the second appointment information 616. Here, the instructions 612 indicate that prior to the appointment with Dr. Smith, the patient needs to have an EKG performed and also indicates that time slots are available for an EKG prior to the appointment with Dr. Smith. By selecting CHECK-IN icon 618, the patient can check-in for his appointment at 8:30 a.m. with Dr. White regarding his hernia operation. In the alternative, the patient can select SCHEDULE EKG icon 620 to schedule an EKG prior to the patient's appointment at 10:30 a.m. with Dr. Smith.

Figure 28:
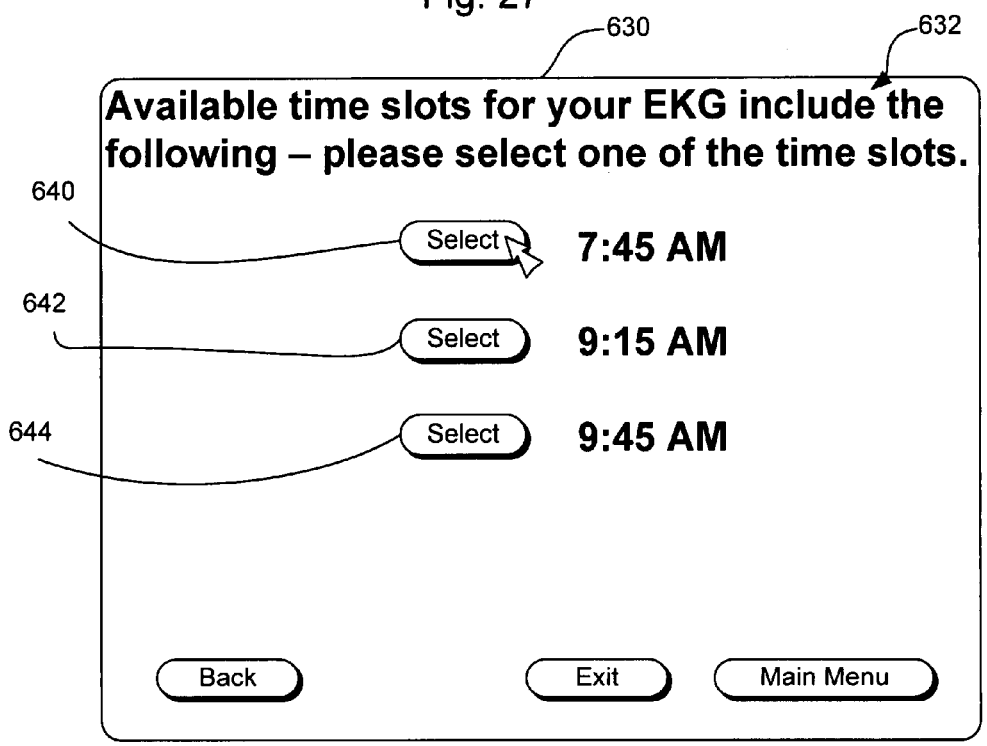
FIG. 28 is a kiosk screen shot that provides multiple time slots for a prerequisite activity to be scheduled.

Referring now to FIG. 28, an exemplary screen shot 630 which may be provided via kiosk 26a when the SCHEDULE EKG icon 620 in FIG. 27 is selected is illustrated which presents a list of times and corresponding SELECT icons for scheduling an EKG. To this end, screen shot 630 lists the times including times 7:45 a.m., 9:15 a.m. and 9:45 a.m. and corresponding SELECT icons 640, 642 and 644, respectively.

Referring to FIGS. 26 and 28, at block 588, when the patient opts not to select one of the open timeslots for an EKG, control passes to block 590 where server 22a indicates via kiosk 26a that the appointment associated with the prerequisite cannot be checked in and removes the appointment from the currently scheduled appointments. After block 590, control passes back to block 230 in FIG. 212 where check-in for appointments that have not been removed from the currently scheduled appointments continues. At block 588, when a patient selects one of the time slots suggested via screen shot 630 in FIG. 28, control passes to block 226 in FIG. 12 where the selected time is added to the currently scheduled appointments and the check-in process continues.

Referring once again to FIG. 6, in at least some embodiments, it is contemplated that kiosk 26a may be used by a patient to check-in for an unfulfilled order to be processed at the next available time instead of during an open time slot in a resource schedule. Thus, for example, where lab work has been ordered for a patient and no specific time slot has been reserved for patient activities associated with the lab work, in at least some embodiments, the patient may simply show up at a facility lab and check-in without a previous appointment. Here, after checking in, the patient's lab work would be added to a schedule queue to be processed the next time resources required to complete the lab work are available.

Figure 29:
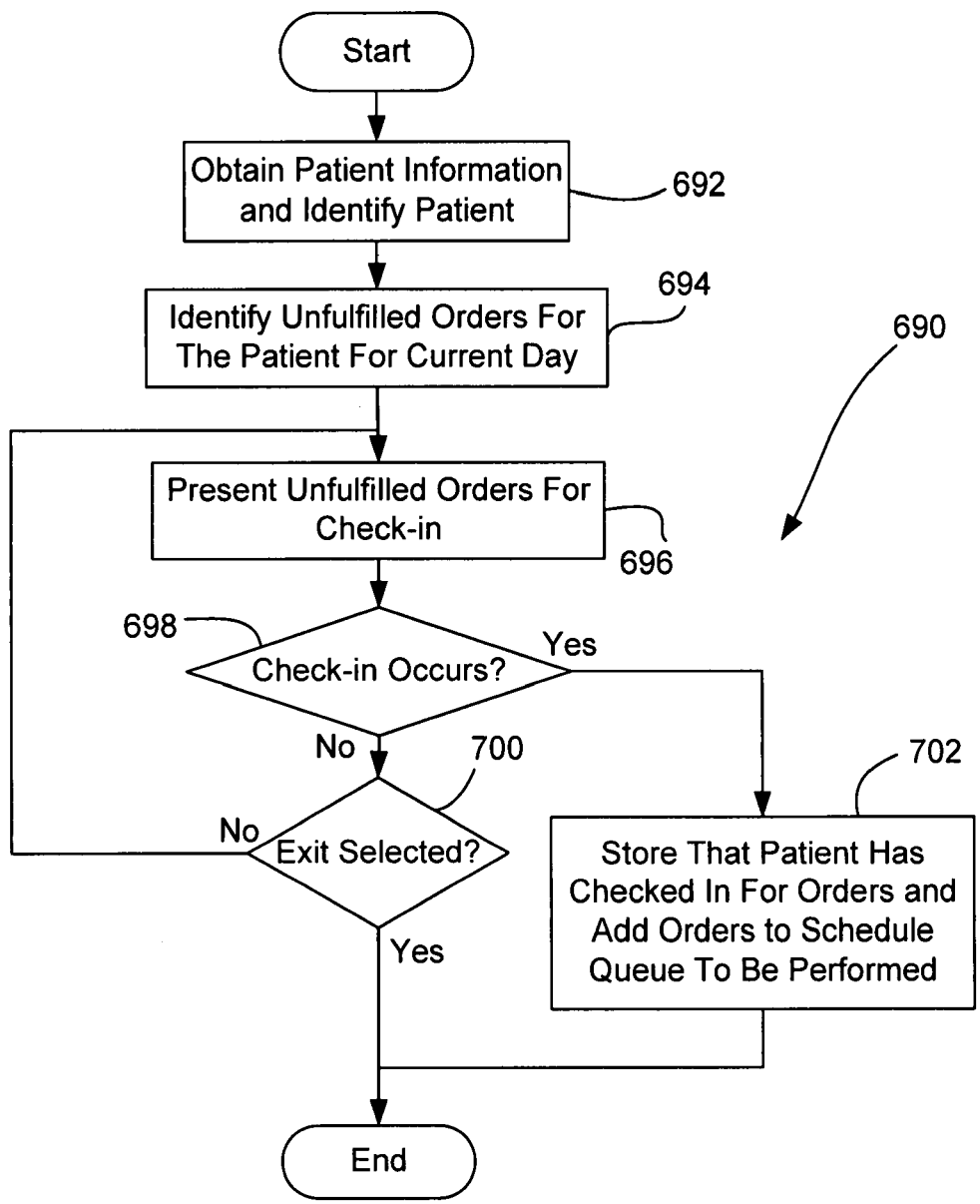
FIG. 29 is a flow chart consistent with at least some aspects of the present invention for checking in patients for unfulfilled orders that are not currently associated with reserved appointment time slots.

Referring now to FIG. 29, an exemplary process 690 that may be performed via the system 10a of FIG. 6 is shown for checking in patients that have existing unscheduled orders to be processed as soon as resources required to perform those activities are available. Referring also to FIG. 6, at block 692, patient information is obtained from the patient via a kiosk 26a and the patient is identified in the manner described above. Here, when the main menu screen shot 370 of FIG. 16 is presented the patient selects icon 376 to check in for unfulfilled orders. At block 694, server 22a accesses an unfulfilled order's database (e.g., see 71 in FIG. 8B) and identifies unfulfilled orders for the patient for the current day. In addition, it may be that some of the unfulfilled orders require an advance appointment. Thus, for example, in FIG. 8B, while a full blood work up and an EKG that represent unfulfilled orders for Bruce Johnson may not need advanced appointments, the follow-up with Dr. Jones related to a skin rash may need to be made as an advanced appointment. Here, it will be assumed that of unfulfilled orders 83 for Bruce Johnson, only the first two (e.g., the full blood work up in the EKG) can be scheduled on a walk in basis.

Figure 30:
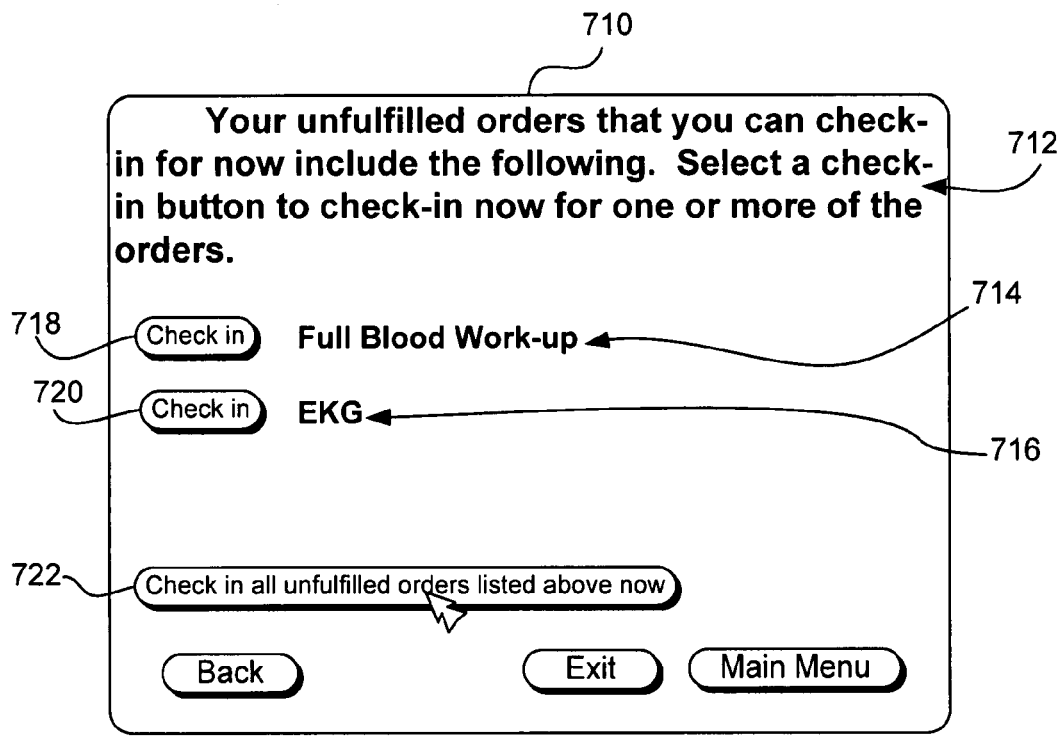
FIG. 30 is a kiosk screen shot that indicates unfulfilled orders that can be checked in on a walk in basis.

Referring still to FIGS. 6 and 29, at block 696, server 22a presents the unfulfilled orders that can be checked in on a walk up basis via kiosk 26. Referring also to FIG. 30, an exemplary screen shot 710 for presenting unfulfilled orders that can be checked in on a walk up basis is illustrated. Screen shot 710 includes instructions 712, information identifying unfulfilled orders that can be checked in on a walk in basis including a full blood work up 714 and an EKG 716 which are consistent with the database 71 shown in FIG. 8B for Bruce Johnson. In addition, separate CHECK-IN icons 718 and 720 are provided for each of the unfulfilled orders 714 and 716, respectively, as well as a CHECK-IN ALL UNFULFILLED ORDERS LISTED ABOVE NOW icon 722. In this case, either of the two orders, 714 or 716 may be checked in separately or, icon 722 may be selected to check in both of orders 714 and 716 at the same time.

Referring to FIGS. 6, 29 and 30, at block 698, server 22a monitors to determine whether or not check-in has occurred. Where a patient checks in for one or more of the unfulfilled orders at block 698, control passes to block 702 where server 22a stores an indication that the patient has checked in for one or more orders and adds the one or more orders to a schedule queue to be performed the next time resources required for the order or orders become available.

Referring again to block 698 in FIG. 29, server 22a cycles through block 698 and block 700 and back up to block 696 until the patient either checks in at block 698 or selects an EXIT icon shown at the bottom of the screen shot 710 in FIG. 30.

Figure 31:
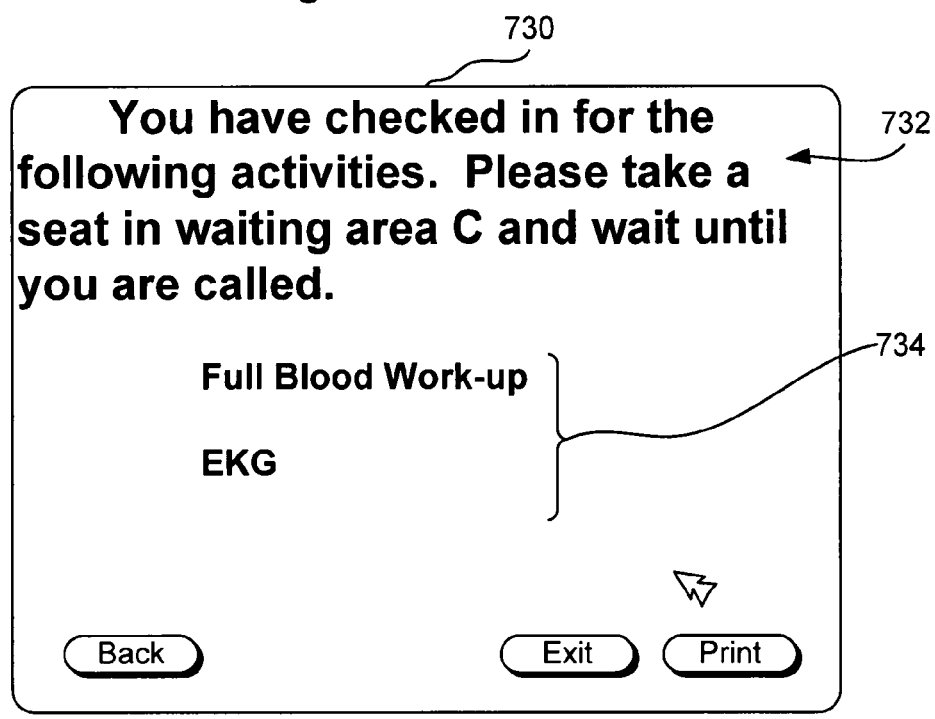
FIG. 31 is a kiosk screen shot that confirms that a patient has been checked in for unfulfilled orders on a walk in basis.

Referring to FIG. 31, an exemplary screen shot 730 for confirming that a patient has been checked in for walk in unfulfilled orders is shown which includes instructions 732 and a list 734 of unfulfilled orders for which the patient is currently checked in.

In addition to being useful when a patient is checking in for an appointment or for scheduling appointments, kiosk 26a is also useful for checking patients out after appointments have occurred. In this regard, it is contemplated that, during any type of medical activities that may occur during an appointment, entries may be made into the patient's EMR where those entries can then be used to identify post-appointment or follow-up activities that should be performed as a matter of course. For example, it may be that the St. Mary's facility requires specific follow-up activities after certain types of appointments have been completed. For example, where a physician sees a patient for chest pain, required follow-up activities may be that the patient take two aspirin every 6 hours for the next 24 hours, that an EKG be performed and that the patient come back for a follow-up visit within a two-week period. As another example, whenever a skin condition XX occurs, physicians at the facility may be required to refer the patient to a specific facility dermatologist that specializes in treating the specific condition.

Figure 11:
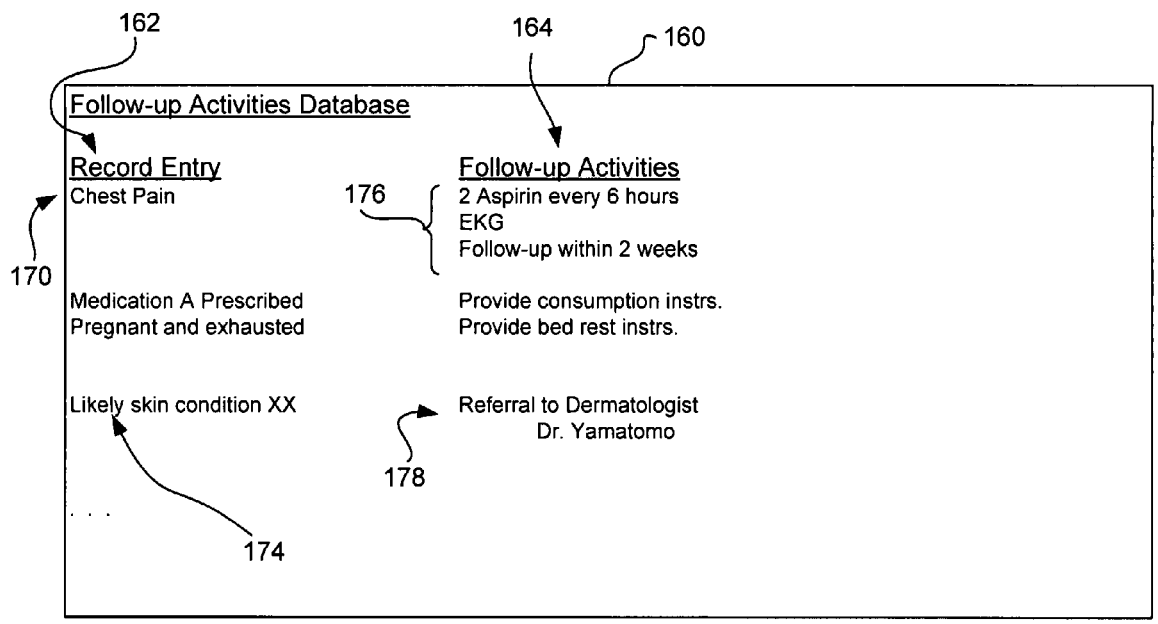
FIG. 11 is a schematic diagram illustrating one example of the follow up activities database of FIG. 6.

Referring now to FIG. 11, an exemplary automatic follow-up activities database 160 is illustrated that includes a record entry column 162 and a follow-up activities column 164. Record entry column 162 lists exemplary entries that may occur in an electronic medical record including, among other entries, a chest pain entry 170 and a likely skin condition XX entry 174. Entries in column 162 may be purely textual so that direct matches have to appear in an EMR to be recognized. In some cases input devices (e.g., see PDA 743 in FIG. 6) may include software that forces a physician to specifically identify column 162 entries. For instance, a device may present a symptoms list for selection by a physician where a first selectable symptom is chest pain, a second symptom is trouble urinating, etc. In addition, it should be appreciated that record entries may take more complex forms such as, requiring combinations of information in an electronic medical record. For example, one entry may require chest pain, that the attending physician was Dr. Jones and that the patient be a male over 50 years old whereas another entry with a different subset of follow-up activities may require chest pain, that the patient is over 50 years old and that the attending physician was Dr. Smith.

Follow-up activities column 164 lists a subset of follow-up activities for each one of the entries in record entry column 162. For example, for the chest pain entry 170 in column 162, column 164 includes three follow-up activities 176 including instructions for the patient to take two aspirin every 6 hours, a requirement for an EKG to be performed and a requirement that a follow-up appointment be scheduled for two weeks after the initial appointment. Similarly, for the likely skin condition XX entry 174 in column 162, column 164 includes a referral to a specific facility dermatologist 178. While database 160 is extremely simple, it should be appreciated that database 160 would typically include several thousand entries in column 162 and corresponding activities in column 164.

Referring once again to FIG. 6, to facilitate entry input into an electronic medical record, it will be assumed that a physician uses handheld device 743 like a personal digital assistant or the like. In the illustrated embodiment, device 743 is wireless and links to network 24a via a wireless access point 745. In the following example, it will be assumed that, during Bruce Johnson's examination related to chest pain by Dr. Smith, Dr. Smith uses device 743 to enter information into Bruce Johnson's electronic medical record. In addition, it is assumed that, after the appointment, Bruce Johnson again accesses kiosk 26a to obtain information related to any follow-up activities.

Figure 32:
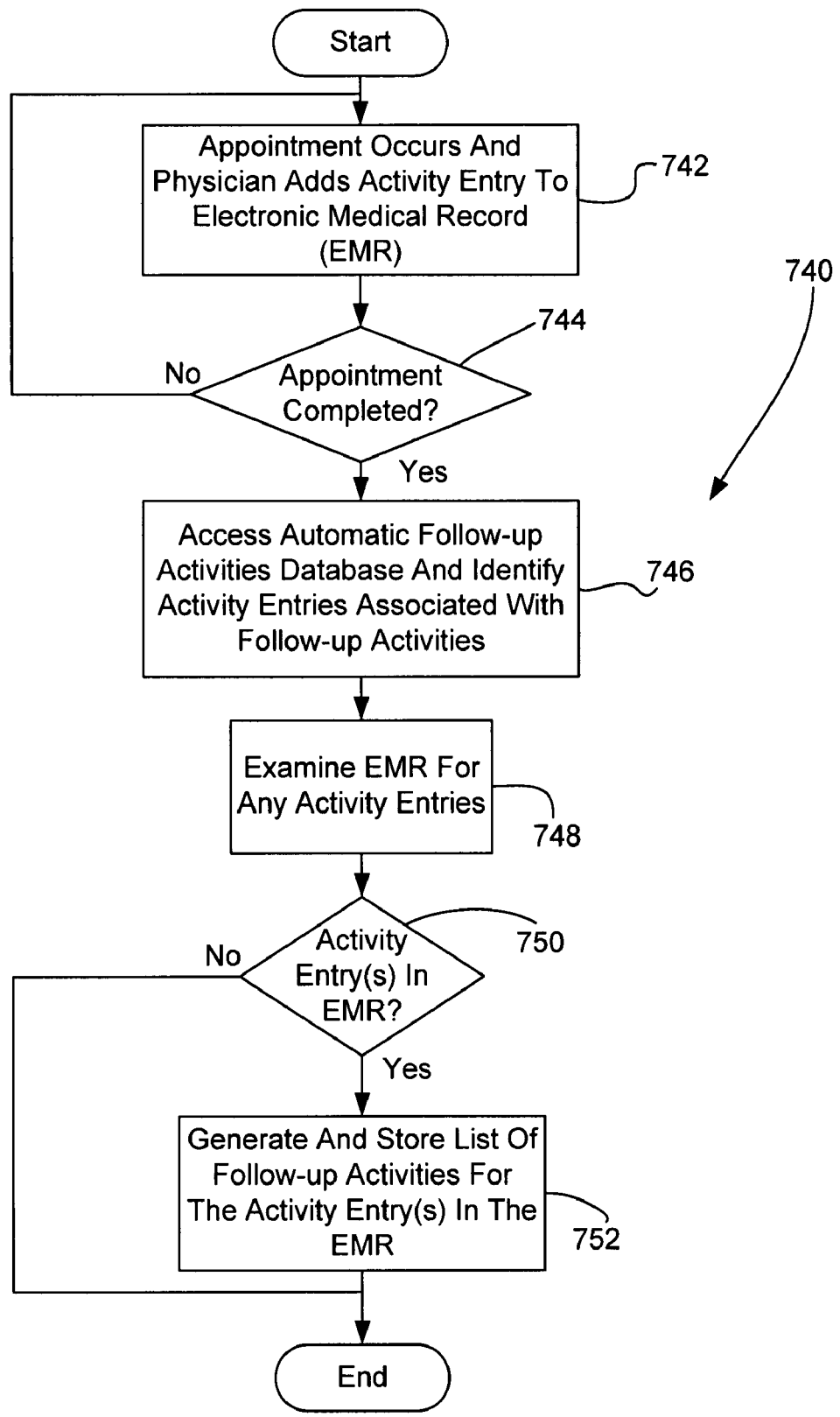
FIG. 32 is a flow chart illustrating a method whereby a physician enters information into an electronic medical record that is thereafter gleaned and used to generate and store a list of follow up activities for a patient associated with the electronic medical records.

Referring also to FIG. 32, a method 740 by which a physician inputs entries into an electronic medical record and by which server 22a identifies follow-up activities for record entries is shown. At block 742, as Dr. Smith is examining Bruce Jones during an appointment, the doctor inputs information into Bruce Johnson's electronic medical record. Until the appointment is completed, control loops from block 744 back to block 742 where additional entries into the electronic medical record are made.

Once the appointment has been completed at block 744, control passes to block 746 where server 22a accesses the automatic follow-up activities database 160 (see again FIG. 11) and identifies activity entries in column 162. At block 748, server 22a examines Bruce Johnson's electronic medical record for any of the record entries from column 162. At block 750, server 22a determines whether or not any of the entries from column 162 appear in Bruce Johnson's electronic medical record. Where none of the entries appear in the record, the process ends. Where one or more of the record entries from column 162 appear in the record, control passes to block 752 where server 22a generates and stores a list of follow-up activities corresponding to Bruce Johnson.

Figure 33:
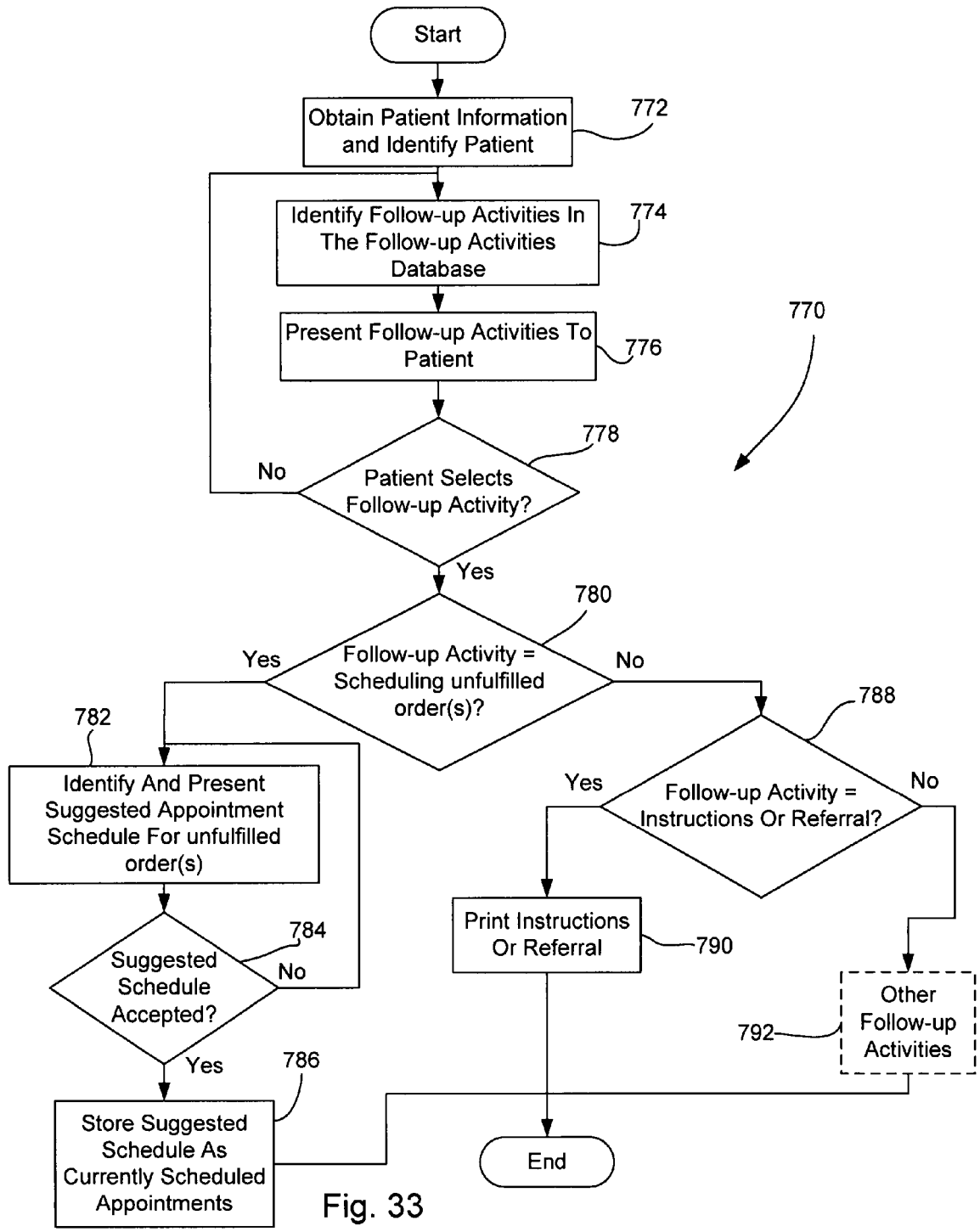
FIG. 33 is a flow chart illustrating a method whereby a patient uses one of the kiosks shown in FIG. 6 to check out after an appointment has been completed.

Referring now to FIG. 33, an exemplary method 770 that facilitates patient checkout is illustrated. Referring also to FIG. 6, at block 772, server 22a obtains patient identifying information and identifies the patient attempting check out. In the present case, consistent with the examples above, it is assumed that Bruce Johnson is in the process of checking out using kiosk 26a. To this end, referring again to FIG. 16, after entering identifying information, main menu screenshot 370 is presented and the patient selects icon 382 to check out. At block 774, server 22a identifies follow-up activities for Bruce Johnson and at block 776, the follow-up activities are presented to the patient via kiosk 26a.

Figure 34:
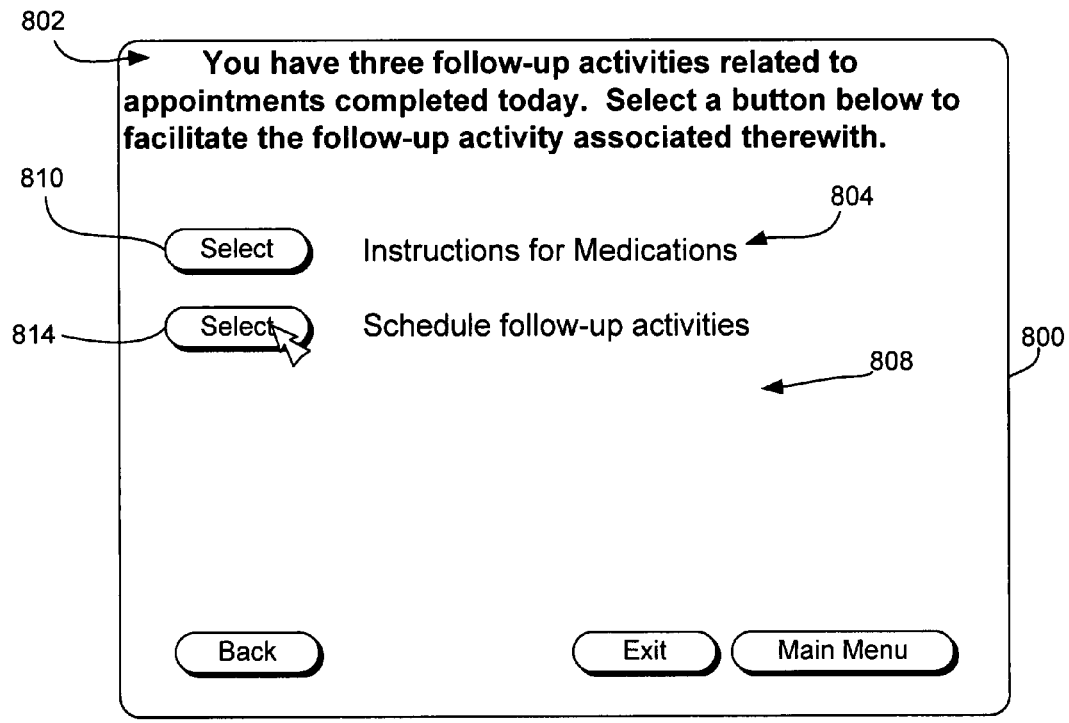
FIG. 34 is a kiosk screen shot that may be presented to a patient during a check out procedure.

Referring now to FIG. 34, an exemplary screen shot 800 for presenting follow-up activities is illustrated. Screen shot 800 includes instructions 802, information identifying two different types of follow-up activities including instructions for medications 804 and follow-up activity scheduling 808 and SELECT icons 810 and 814 for each of the different types of follow-up activities 804 and 808, respectively. By selecting icon 810, the patient can obtain instructions for medication that should be consumed. By selecting icon 814, the patient can schedule follow-up activities.

Figure 35:
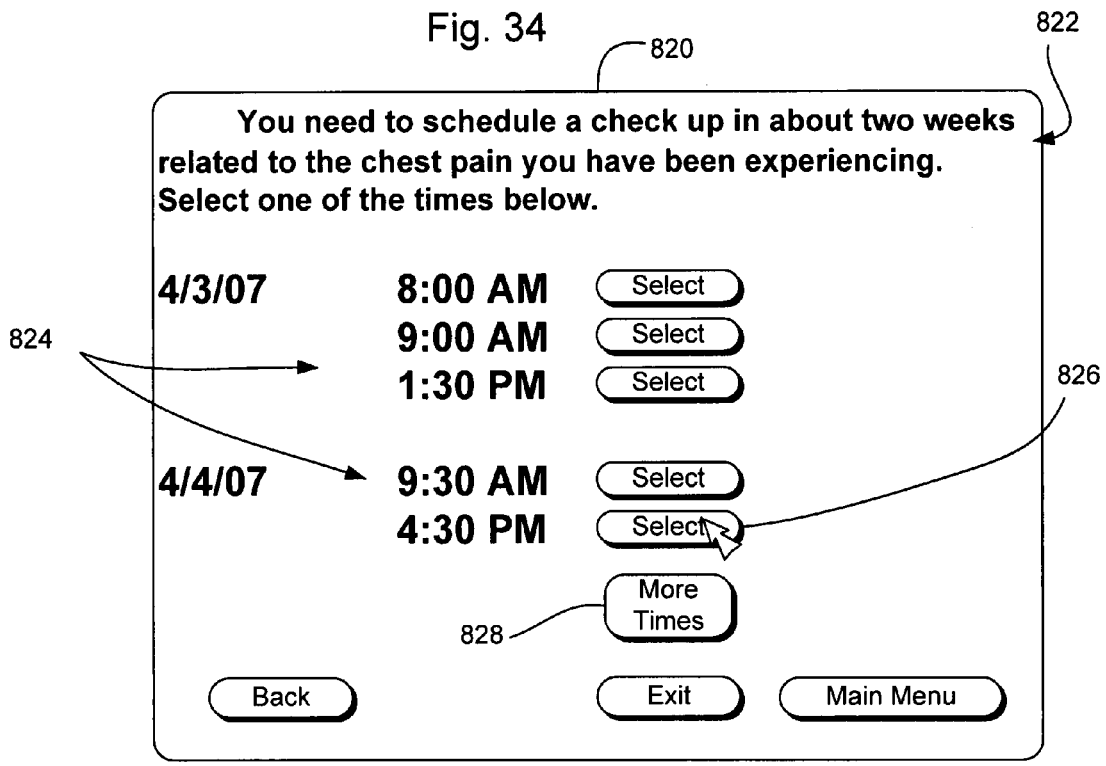
FIG. 35 is a kiosk screen shot indicating time slots that a patient can select for scheduling follow up activities after an appointment has been completed.
Figure 36:
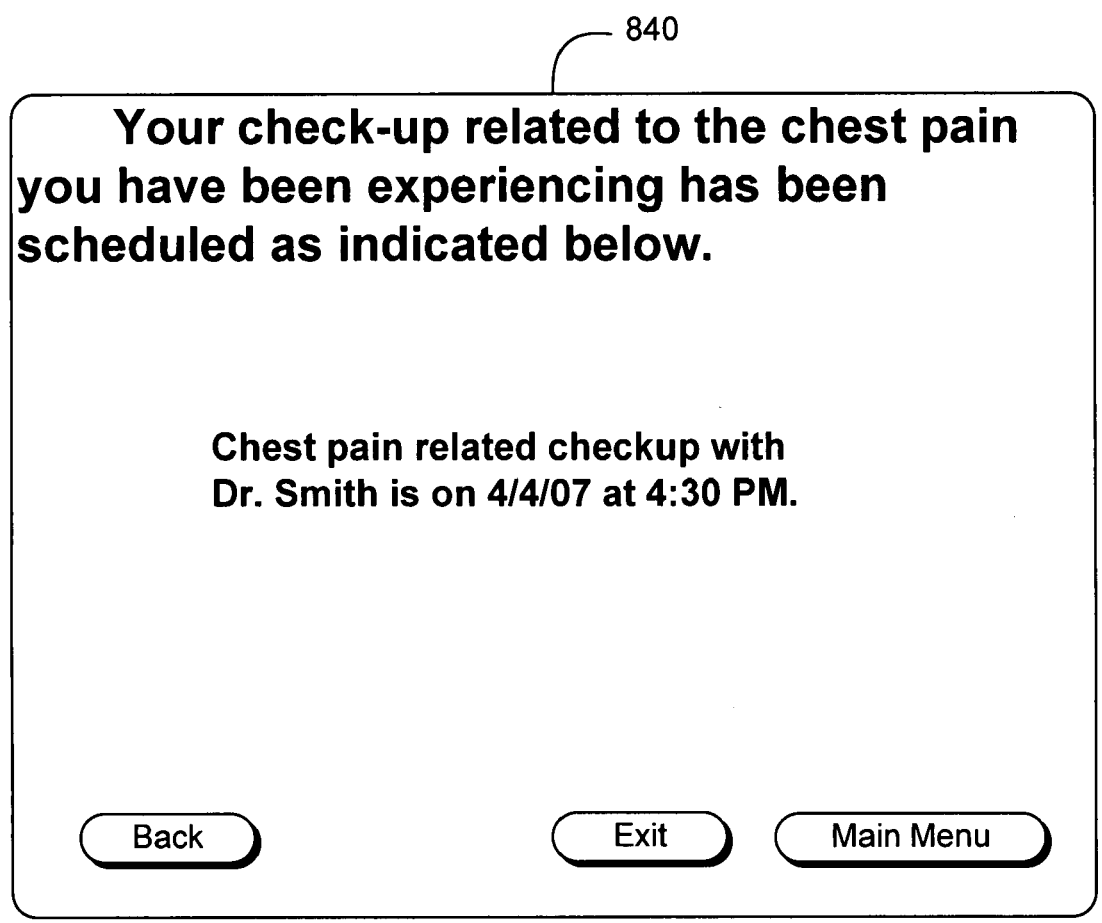
FIG. 36 is a kiosk screen shot for confirming that a patient has scheduled an appointment during check out.

Referring still to FIGS. 6 and 33 as well as FIG. 34, once the patient selects one of icons 810 or 814 at block 778, control passes to block 780 where server 22a determines whether or not the follow-up activity selected includes scheduling an appointment. Where scheduling activities have been selected, control passes to block 782 where server 22a identifies and presents a suggested appointment schedule. Referring also to FIG. 35, an exemplary screen shot 820 for presenting a suggested appointment schedule is illustrated. Screen shot 820 includes instructions 822 that identify the activity to be scheduled. In addition, screen shot 820 includes different scheduled time slots 824 appropriate for scheduling the activity as well as a plurality of select icons, a separate icon 826 corresponding to each one of the time slots that may be selected for scheduling the activity identified in the instructions 822. A MORE TIMES icon 828 is provided to allow the patient to view other times that may be available for scheduling the activity. In the present example, it is assumed that Bruce Johnson selects icon 826 corresponding to the 4:30 p.m. time slot on Apr. 4, 2007. Once icon 826 has been selected to accept one of the suggested schedules at block 784, control passes to block 786 where a suggested schedule is stored as a currently scheduled appointment and a confirmation screen shot as shown in FIG. 36 is presented.

Referring still to FIG. 33, at block 780, if the follow-up activity selected is not a scheduling activity, control passes to block 788 where server 22a determines whether or not the follow-up activity includes printing instructions. Where instructions for medication is the follow up activity, control passes to block 790 where instructions are printed for the patient. Block 792 in FIG. 33 represents other types of follow-up activity such as generation of a referral, generating lab orders, etc.

In addition to generating suggested appointment schedules for adding additional appointments to currently scheduled appointments, in at least some embodiments, server 22a may be programmed to analyze currently scheduled appointments to identify more optimal schedules and to present suggested schedules that may be more optimal. For instance, in the example above where Mr. Johnson has first and second appointments at 8:30 a.m. and 10:30 a.m., if the anticipated duration of the first appointment is 15 minutes, if the schedules of resources required for the second appointment permit, it may be preferred if the second appointment is moved to a 9:00 a.m. time slot so that Mr. Johnson can finish up more quickly. As another instance, referring again to FIG. 8A, it can be seen that on Mar. 12, 2007 Mr. Johnson has an extended open time slot between 9:00 a.m. and 10:30 a.m. appointments and that on Apr. 20, 2007 Mr. Johnson has another appointment (see bar 181) that, at least temporally, fits into the open time slot on Mar. 12, 2007. Here, the patient may prefer to schedule the Apr. 20, 2007 appointment in the Mar. 12, 2007 open time slot to avoid having to make another trip to the facility.

Figure 37:
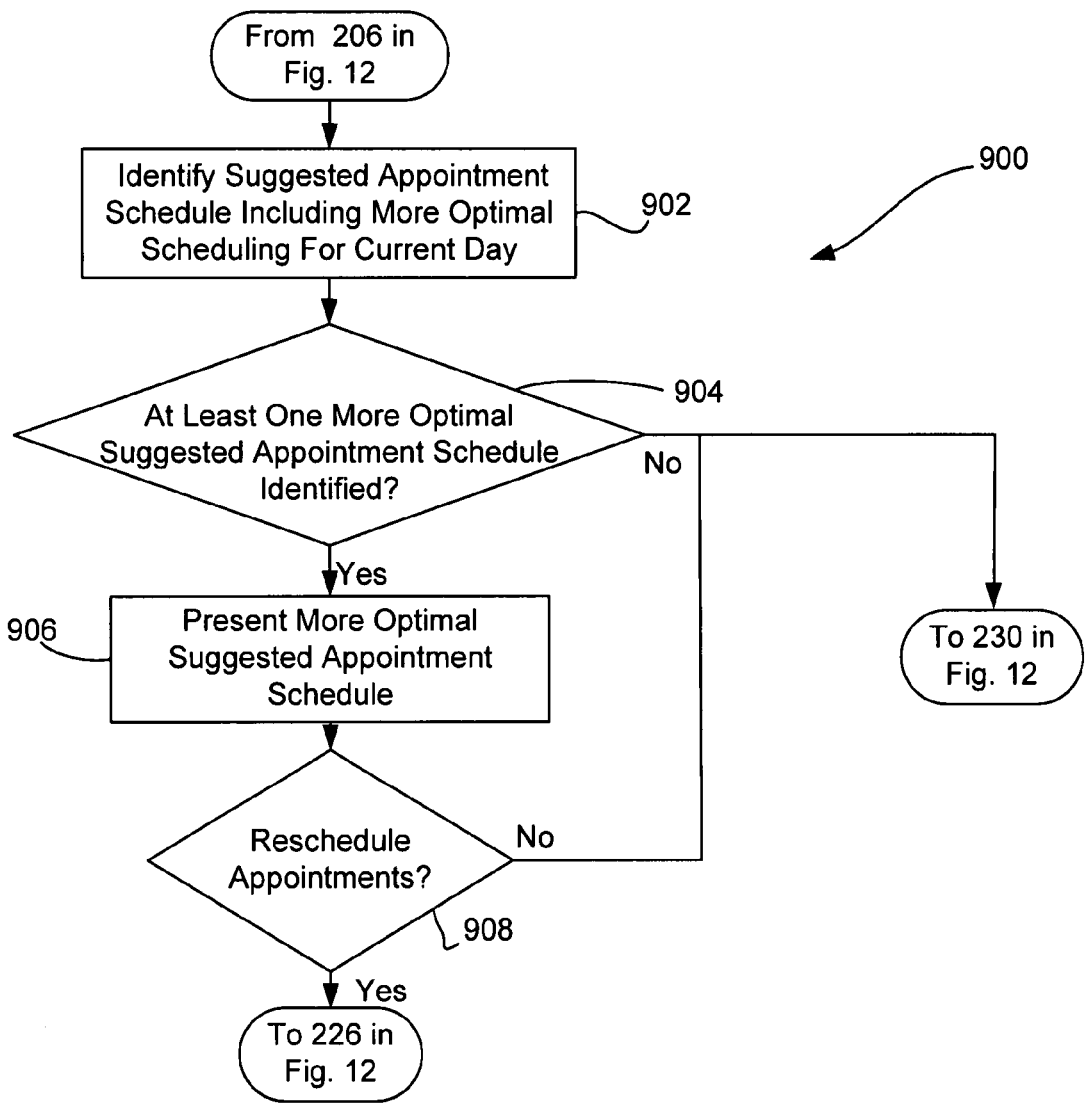
FIG. 37 is a sub-process that may be substituted for a portion of the process shown in FIG. 12 for identifying currently scheduled appointments that may be rescheduled in a more optimal fashion.

Referring to FIG. 37, a sub-process 900 that may be substituted in the FIG. 12 method for blocks 210, 212, 220, 224, 226 and 227 is illustrated for shifting currently scheduled appointments when a patient checks in. Referring also to FIGS. 6 and 12, after current appointments are identified at block 206 control may pass to block 902 in FIG. 37. At block 902 server 22a attempts to identify a suggested schedule appointment including currently scheduled appointments that is more optimal than the current schedule. At block 904, where no more optimal suggested schedule is identified control passes to block 320 in FIG. 12 where check in continues.

At block 904, where at least one more optimal suggested schedule is identified control passes to block 906 where the optimal schedule is presented. At block 908, if the patient decides not to accept the seemingly optimal schedule control passes to block 230 in FIG. 12. When the patient elects the optimal schedule at block 908 control passes to block 228 in FIG. 12 where the optimal schedule appointments are stored as currently scheduled appointments.

While the inventive systems are generally described above in the context of an exemplary patient self check-in kiosk, at least some of the inventive concepts are useful in the context of a receptionist check-in terminal. To this end, referring again to FIG. 6, an exemplary receptionist terminal 950 is shown linked to network 24a where the terminal 950 has components similar to the components described above in the context of kiosk 26a. As in the case of the patient kiosk, here it is contemplated that a simplified check-in/scheduling interface would be provided to a receptionist or staff member that makes it extremely easy for a receptionist to identify schedule optimizing options and to modify a patients schedule when desired.

Figure 38:
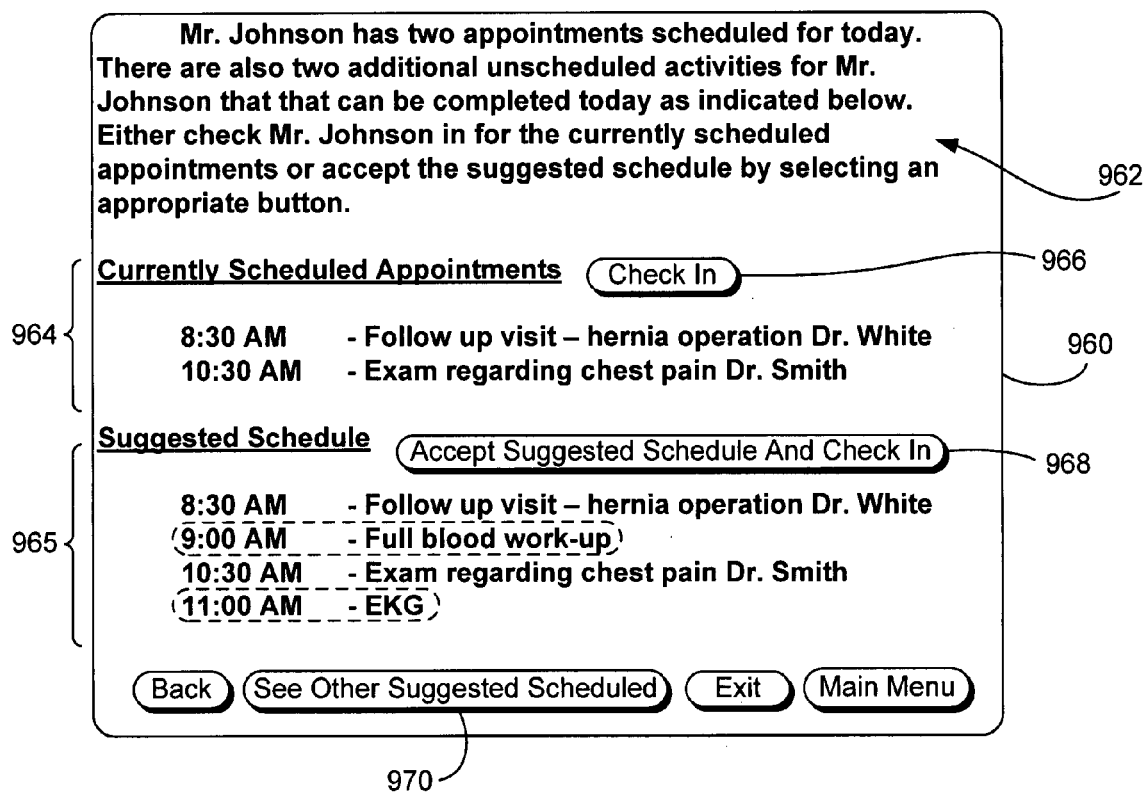
FIG. 38 is an exemplary receptionist's terminal screen shot that may be generated to facilitate simplified optimal patient appointment scheduling.

Referring now also to FIG. 38, after a receptionist has entered patient identifying information via terminal 1950, an exemplary check-in/scheduling screenshot 960 corresponding to the patient may be presented. As seen in FIG. 38, screenshot 960 includes abbreviated instructions 962, a current schedule appointments section 964, a suggested schedule section 965 and a plurality of mouse selectable button icons to facilitate checking in. A CHECK-IN icon 966 may be selected to check in for currently scheduled appointments at 8:30 a.m. and 10:30 a.m. that are specified in section 964.

Section 965 presents a suggested schedule that includes the currently scheduled 8:30 a.m. and 10:30 a.m. appointments as well as suggested appointments at 9:00 a.m. and 11:00 a.m. for two unfulfilled orders. The suggested unfulfilled order appointments are visually distinguished in the suggested schedule so that the receptionist can clearly distinguish suggested appointments. An ACCEPT SUGGESTED SCHEDULE AND CHECK-IN icon 968 can be selected to accept the schedule suggested in section 965 and to simultaneously check-in for all four appointments. A SEE OTHER SUGGESTED SCHEDULES icon 970 is selectable to view other suggested schedules if desired.

Thus, referring still to FIG. 38, in addition to allowing a receptionist to quickly check a patient in for currently scheduled appointments in a fashion similar to existing check-in interfaces, screen shot 960 provides an optimal suggested schedule for the patient that can be accepted and for which a patient can be checked in with the single click of a button 968.

In the case of receptionist terminal 950 it should be appreciated that any of the features or enhancements above may be enabled such as, for instance, identifying any type of additional unscheduled activities that may be scheduled for a patient, plugging open time slots when required resources are available, shifting currently scheduled appointments to accommodate additional activities, etc.

In at least some embodiments it is contemplated that the system may, in addition to checking a patient's appointment schedule database and/or resource schedule databases, be able to access a patient's general schedule or calendar to determine if a suggested appointment schedule will fit into the patient's general schedule prior to suggesting the suggested appointment schedule. In addition, in some cases the system may also have access to a database that estimates travel times between locations (e.g., XL Travel, Yahoo Travel, etc.) and may take into account travel times between general schedule appointments for a patient prior to suggesting an optimized appointment schedule.

Figure 39:
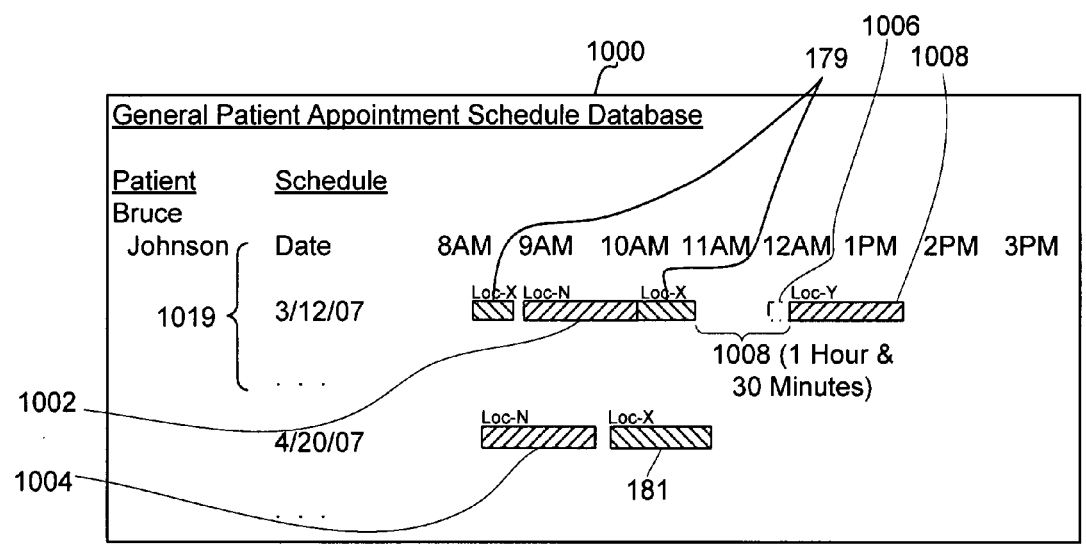
FIG. 39 is a schematic illustrating an exemplary general patient appointment schedule database that is consistent with at least some aspects of the present invention.

To this end, an exemplary General Patient Appointment Schedule Database 1000 is shown in FIG. 39. Database 1000 includes schedule information for patient Bruce Johnson and, consistent with the example above, includes appointments for two activities associated with a medical facility that occur at 8:30 a.m. and 10:30 a.m. (see 179) on Mar. 12, 2007 and an appointment 181 on Apr. 20, 2007 at 10 a.m. as well as other general appointments (e.g., business meetings, etc.) shown as left to right upward cross hatched bars from 9 a.m. to 10:30 a.m. (see 1002) and from 12:30 p.m. to 1:30 p.m. on Mar. 12, 2007 (see 1008) and on Apr. 20, 2007 from 8:40 a.m. to 9:50 a.m. (see 1004). The 10:30 a.m. appointment on Mar. 12, 2007 is expected to last until 11 a.m. Thus, on Mar. 12, 2007 there is very little free time between appointments 179 and there is a one and a half hour time slot open between the expected terminating time of the 10:30 a.m. appointment and the beginning of the 12:30 p.m. appointment.

In the above case, when Mr. Johnson logs onto a check in kiosk to check in for his 8:30 a.m. appointment, the system may be programmed to automatically check Mr. Johnson's general schedule when attempting to identify a suggested optimized schedule for Mr. Johnson. In the above example, because there is very little free time between the 8:30 a.m. and 10:30 a.m. appointments on Mar. 12, 2007, the system may not identify a suggested schedule that includes a time slot intermediate the currently scheduled 8:30 and 10:30 appointments. However, because there is a 1½ hour open slot in the general patient schedule from 11:00 a.m. to 12:30 a.m., the system may identify a time slot in that time range during which resources are available that can be used to facilitate some unfulfilled activity for the patient and may then suggest an optimized schedule including the unfulfilled activity. Thus, for instance, where the unfulfilled activity is expected to require 30 minutes to complete, the system may identify a time slot from 11:15 to 11:45 during which the unfulfilled activity can be scheduled and may suggest that time to the patient.

In some cases the system may also be programmed to identify an estimated time of travel between general appointment locations and to take that estimated time into account when determining if a schedule should be suggested. To this end, referring still to FIG. 39, in addition to storing scheduling information for a patient, the schedule database 1000 may also store location information associated with each or at least a subset of scheduled appointments and facilities at which appointments may be scheduled. In FIG. 39 appointment locations are indicated by labels like "Loc-X", "Loc-Y", etc., to indicate different geographic locations. Thus, as shown, appointments 179 are to occur at location X, appointment 1002 is to occur at a location N and appointment 1008 is to occur at location Y.

Prior to using a patient's general schedule database to attempt to identify an optimized schedule for the patient, it is assumed that server 22a (see again FIG. 6) would be provided access to the patient's general schedule database in some fashion. Thus, for instance, when the patient first accesses a check in kiosk or registers to use check in kiosks with a receptionist or the like, the patient may provide the patient's e-mail address or some code that allows server 22a to access the patient's general schedule. Here, the general schedule may be accessible in a "dumbed down" format where schedule content is not provided to maintain the patient's privacy. Any method for granting access to a patient's general schedule that is known in the art could be used here. In the alternative, in at least some cases, a patient may set up his general schedule or calendar software to send updates to a medical facility calendar/patient scheduling system so that the patient's general appointments can be added to the patient's medical appointments calendar in a secure fashion.

Figure 40:
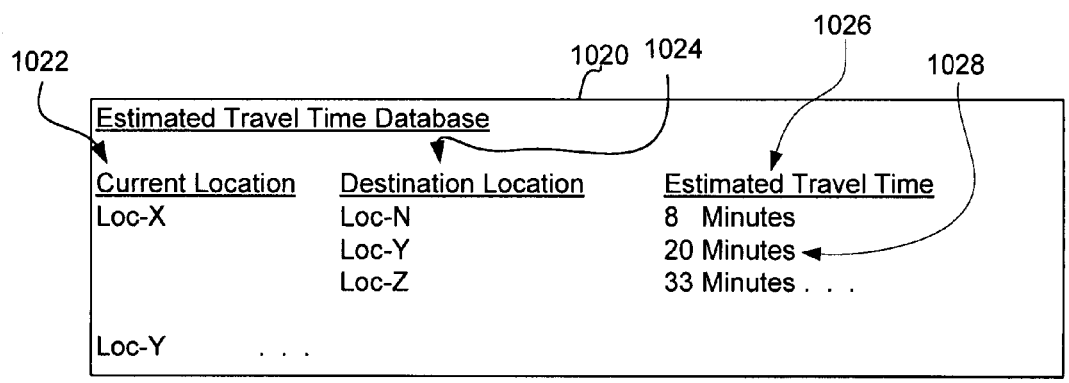
FIG. 40 is a schematic of an exemplary estimated travel time database that is consistent with at least some inventive embodiments.

Referring to FIG. 40, an exemplary Estimated Travel Time Database 1020 is illustrated that includes a Current Location column 1022, a Destination Location Column 1024 and an Estimated Travel Time column 1026. As the label implies, column 1022 lists all locations within an area such as a municipality, a state, etc. while column 1024, for each entry in column 1022, lists all locations within the area while column 1026 indicates an estimated travel time for each pair of locations in columns 1022 and 1024. Thus, for instance, column 1026 indicates that the estimated travel time between locations Loc-X and Loc-y is 20 minutes (see 1028).

Figure 41:
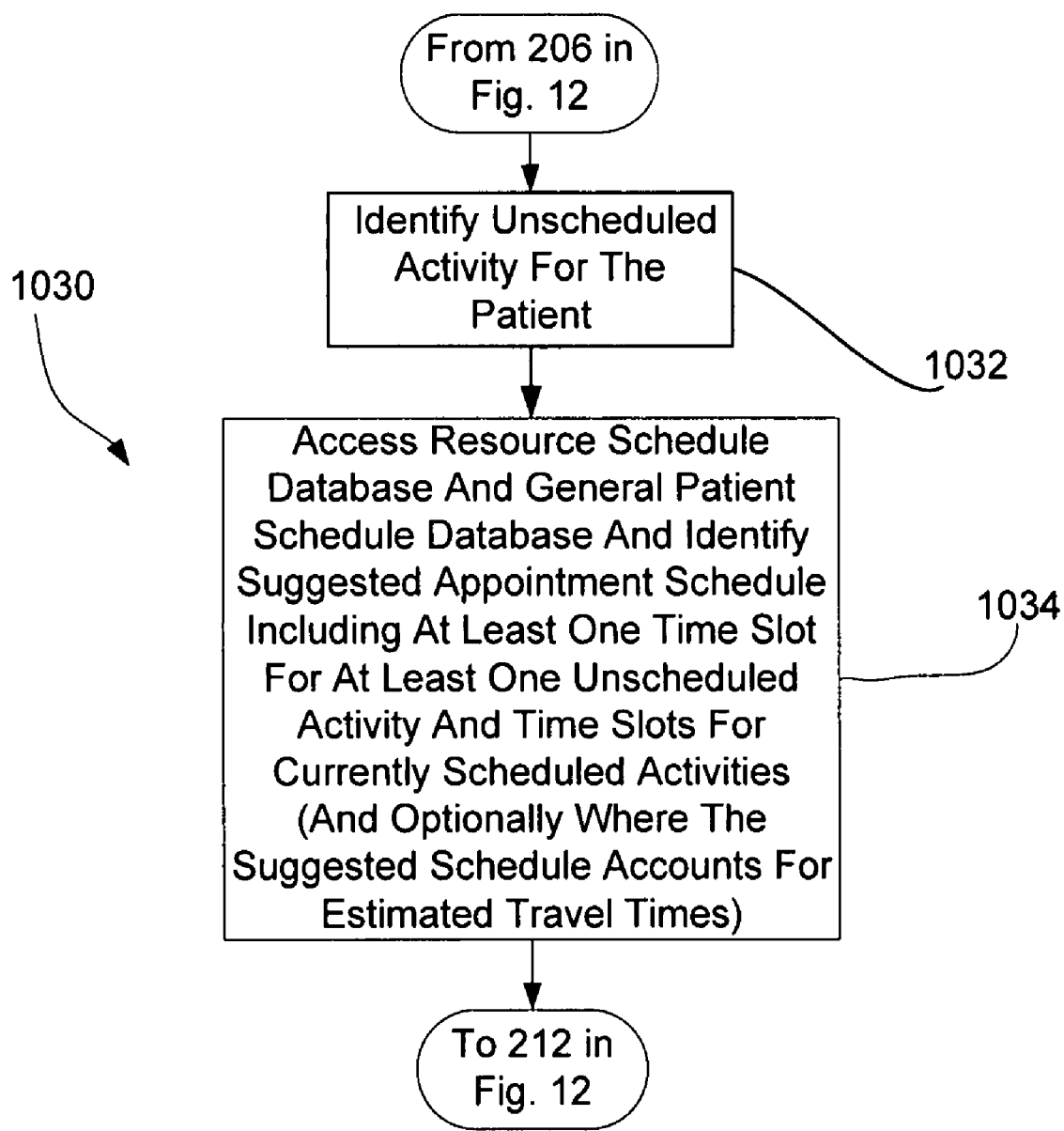
FIG. 41 is a sub-process that may be substituted for a portion of the method illustrated in FIG. 12 where the system accounts for a patient's general schedule appointments and travel times when attempting to identify an optimized schedule.

Referring now to FIG. 41, a sub-process 1030 that may be substituted for a portion of the process shown in FIG. 12 is illustrated. Referring also to FIG. 12, after currently scheduled medical facility of campus appointments are identified for a current day at block 206, control may pass to block 1032 in FIG. 41 where any type of unscheduled activity for the patient can be identified. Next, at block 1034 server 22a may access the resource schedule database 312 shown in FIG. 7 as well as the general patient schedule database shown in FIG. 39 and identify a suggested appointment schedule that includes at least one time slot for at least one unscheduled activity and time slots for the currently scheduled activities that fit into the patient's general schedule as well as the scheduled of resources required to complete the activities. After block 1034 control may pass back to block 212 in FIG. 12 where the process described above continues.

Where location information is stored in a patient's general schedule as shown in FIG. 39 and where server 22a has access to a travel time database as shown in FIG. 40, server may also optionally access the travel time database 1020 and account for estimated travel times when attempting to identify an optimized schedule to suggest to the patient. Thus, for instance, in the above example, where the travel time between locations X and Y is estimated to be 20 minutes (see 1028 in FIG. 40) and the resources required to complete a specific activity are needed for another appointment until 11:45 a.m. on Mar. 12, 2007, even though Mr. Johnson's schedule indicates that he has a time slot open from 11:45 a.m. to 12:15 p.m. on Mar. 12, 2007, the system would not suggest the time slot because that would only leave Mr. Johnson 15 minutes to travel from location X to location Y and would render Mr. Johnson late for his 12:30 appointment.

In other cases where the system does not have access to a travel time database 1020, the system may be programmed to assume a default estimated travel time between locations within an area (i.e., a municipal area). Thus, for instance, in the case of Madison Wis., a person can usually travel from one location to another within the general area within 20 minutes so the default estimated travel time may be 20 minutes and the system may use that default time accordingly when attempting to identify a suggested optimized schedule for a patient.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For instance, in at least some cases it is contemplated that the kiosks may be replaced by hand held devices such as personal digital assistants, cell phones, etc., like the device 1050 shown in FIG. 6 which is meant to represent a remote personal device. In this case, whenever an optimized suggested schedule is identified, the schedule may be pushed to a patient's portable device 1050 along with the ability to accept the suggested schedule and revise the patients currently scheduled appointments accordingly. In the alternative, some preset time before an appointment occurs (e.g., one day), optimized schedules may be identified and pushed to patients portable devices. Where optimized schedules are automatically identified and pushed to clients for consideration prior to check-in, one or more appointments may be shifted to subsequent time slots to cluster appointments optimally (e.g., a first scheduled appointment may be shifted to a subsequent day to facilitate clustering). Here, the idea is to push optimized scheduling options to patients at times just prior (e.g., one to two days prior) to currently scheduled appointments when a patient will likely know whether or not the patient's schedule will accommodate the suggested optimized schedule so that the patient can make an informed decision.

Moreover, while the simplified scheduling system described above has many advantages, in at least some cases it is contemplated that a kiosk may also present more detailed scheduling options for time slots that are not temporally proximate currently scheduled appointments when a patient checks in for an appointment. Thus, it has been recognized that a good time to provide scheduling options to a patient is upon check-in for a current appointment when the patient may have some additional time to consider scheduling options. Accordingly, the scope of the invention should be determined from the following claims and not limited by the above disclosure.

Furthermore, while the example above that considers a patient's general schedule when attempting to identify a suggested optimized schedule is described in the context of a check in kiosk, it should be appreciated that other systems are contemplated that provide this functionality to a patient and/ or to a scheduling employee or a receptionist. To this end, tying scheduling software to patient's general scheduling or calendaring can allow anyone who is scheduling appointments for patients to identify suggested optimized schedules for patients that account for currently scheduled general appointments as well as appointments associated with a medical facility/campus/enterprise.

To apprise the public of the scope of this invention, the following claims are made.

What is claimed is:

1. A method for allowing a patient at a medical facility using a public kiosk to check in for currently scheduled appointments, the method comprising the steps of:
   providing the kiosk in a location for use by patients;
   via the kiosk, receiving identifying information from the patient checking in for an appointment at a selected time;
   retrieving data from a patient appointment database to identify currently scheduled appointments for the patient that are temporally proximate the selected time to allow the patient to selectively check in via the kiosk where the currently scheduled appointments are associated with currently scheduled appointment activities and initially scheduled appointment time slots;
   retrieving data from a best practices database that correlates circumstance subsets with opportunistic activities that should be performed;
   identifying at least one unscheduled activity for the patient that corresponds to a patient circumstance in the database in addition to the currently scheduled appointment activities for the patient;
   identifying at least one suggested appointment schedule including at least one open time slot during which the patient may complete the unscheduled activity and the currently scheduled appointment activities; and
   via the kiosk, presenting the at least one suggested appointment schedule to the patient; and
   prompting the patient to accept or reject the suggested appointment via a user interface corresponding to the kiosk;
   during an accepted appointment, receiving at least one activity entry and storing the activity entry in a first electronic medical record (EMR) wherein an activity entry includes data usable to determine whether a post-appointment follow-up activity associated with the activity entry should be performed; and
   selectively identifying post-appointment follow-up activities associated with the identified activity entry corresponding to the patient and selectively presenting at least a subset of the identified post-appointment follow-up activities at the kiosk.

2. The method of claim 1 further including the step of receiving input via the kiosk to accept the suggested appointment schedule and automatically adding the unscheduled activity to the appointment schedule to update the currently scheduled appointments.

3. The method of claim 2 wherein the steps of receiving input via the kiosk to accept the suggested appointment schedule and automatically adding the unscheduled activity to the appointment schedule to update the currently scheduled appointments includes presenting a single icon via a display screen that, when selected, causes the unscheduled activity to be added to the appointment schedule and receiving input via the single icon.

4. The method of claim 1 further including the step of providing an unfulfilled order database that includes unfulfilled orders for the patient and further comprising the step of accessing the unfulfilled order database and identifying a first unfulfilled order for the patient as the additional unscheduled activity.

5. The method of claim 4 further including the step of providing a resource schedule database that includes resource schedules for resources required to complete unfulfilled orders wherein unfulfilled orders are activities ordered to be completed that are currently unscheduled and wherein the step of identifying at least one suggested appointment schedule includes:
   identifying resources required to complete the first unfulfilled order for the patient; and
   identifying at least one non-conflicting time slot in the resource schedules for the resources required to complete the first unfulfilled order wherein the non-conflicting time slot is different than the initially scheduled appointment time slots.

6. The method of claim 5 wherein at least one of the currently scheduled appointments is for a first time slot and wherein the step of identifying at least one non-conflicting time slot includes identifying at least one non-conflicting time slot that is temporally proximate the first time slot.

7. The method of claim 6 wherein the step of identifying at least one non-conflicting time slot that is temporally proximate the first time slot includes identifying at least one time slot that is within one hour of the first time slot.

8. The method of claim 5 further including the step of providing a location database that includes locations where resources are used in the facility wherein a first currently scheduled appointment is for a first time slot and the step of identifying at least one non-conflicting time slot includes identifying the location of the first currently scheduled appointment and the locations of the resources required to perform the first unfulfilled order, using the location database to identify an estimated travel time between the location of the first currently scheduled appointment and the locations of the resources required to perform the first unfulfilled order and determining that a time interval at least as long as the estimated travel time exists between the first time slot and the non-conflicting time slot.

9. The method of claim 1 wherein the step of identifying at least one suggested appointment schedule includes identifying a schedule that includes multiple open time slots during which the patient may complete the unscheduled activity.

10. The method of claim 1 wherein the step of identifying at least one unscheduled activity for the patient includes identifying multiple unscheduled activities for the patient in addition to the currently scheduled appointment activities for the patient and wherein the step of identifying at least one suggested appointment schedule includes identifying a schedule that includes open time slots during which the patient may complete each of the unscheduled activities and the currently scheduled appointment activities.

11. The method of claim 10 wherein the suggested appointment schedule includes a distinct time slot for each of the unscheduled activities and for each of the currently scheduled appointment activities.

12. The method of claim 1 wherein a first currently scheduled appointment is initially for a first time slot and wherein the step of identifying at least one suggested appointment schedule includes identifying a schedule wherein the activities associated with the first currently scheduled appointment are associated with a second time slot that is different than the first time slot.

13. The method of claim 12 further including the step of receiving input via the kiosk to accept the suggested appointment schedule and automatically rescheduling the first currently scheduled appointment for the second time slot, cancelling the first currently scheduled appointment at the first time slot and adding the unscheduled activity to the appointment schedule in one of the open time slots.

14. The method of claim 1 further including the step of providing a prerequisites database that includes prerequisites associated with activities performed at the facility wherein prerequisites are activities that have to be performed prior to other activities being performed and wherein the step of identifying at least one unscheduled activity for the patient includes accessing the prerequisites database and identifying a first prerequisite associated with at least one of the currently scheduled appointment activities as the unscheduled activity.

15. The method of claim 14 further including the step of providing a resource schedule database that includes resource schedules for resources required to complete prerequisite activities and wherein the step of identifying at least one suggested appointment schedule includes:
identifying resources required to complete the first prerequisite; and
identifying at least one non-conflicting time slot in the resource schedules for the resources required to complete the first prerequisite wherein the non-conflicting time slot is different than the initially scheduled appointment time slots.

16. The method of claim 15 wherein at least one of the currently scheduled appointments is for a first time slot and wherein the step of identifying at least one non-conflicting time slot includes identifying at least one non-conflicting time slot that is temporally proximate the first time slot.

17. The method of claim 16 wherein the step of identifying at least one non-conflicting time slot includes identifying a time slot that is prior to the first time slot.

18. The method of claim 1 further including the step of providing a resource schedule database that includes resource schedules for resources required to complete opportunistic activities and wherein the step of identifying at least one suggested appointment schedule includes:
identifying resources required to complete the unscheduled activity; and
identifying at least one non-conflicting time slot in the resource schedules for the resources required to complete the unscheduled activity wherein the non-conflicting time slot is different than the initially scheduled appointment time slots.

19. The method of claim 18 wherein at least one of the currently scheduled appointments is for a first time slot and wherein the step of identifying at least one non-conflicting time slot includes identifying at least one non-conflicting time slot that is temporally proximate the first time slot.

20. The method of claim 1 wherein a first currently scheduled appointment is for a first time, the step of identifying at least one suggested appointment schedule including identifying that the first currently scheduled appointment has been delayed and identifying a non-conflicting time slot that includes at least a portion of the first time slot.

21. The method of claim 1 wherein temporally proximate appointments include appointments that occur within three hours of the first time.

22. The method of claim 1 for use after a first appointment has been completed and prior to the patient exiting the facility further comprising the step of identifying at least one unscheduled activity including an unfulfilled order generated during the first appointment.

23. The method of claim 1, further comprising the steps of:
providing an unfulfilled order database that includes unfulfilled orders wherein an unfulfilled order is an unscheduled activity requested by a clinician;
identifying at least a first unfulfilled order for the patient in the unfulfilled order database;
via the kiosk, presenting the first unfulfilled order to the patient; and
via the kiosk, receiving input indicating that the patient intends to check in for the unfulfilled order.

24. The method of claim 23 wherein the step of identifying at least a first unfulfilled order includes identifying a plurality of unfulfilled orders for the patient in the existing database and wherein the step of presenting the unfulfilled order includes presenting at least a subset of the plurality of unfulfilled orders for the patient.

25. The method of claim 24 wherein the step of presenting includes presenting the unfulfilled orders via a display screen, the method further including the steps of providing a single selectable icon via the display screen for selection to add all of the presented unfulfilled orders to the schedule queue to be performed.

26. The method of claim 23 wherein the unfulfilled order is for a lab activity.

27. The method of claim 1 wherein the step of identifying follow-up activities includes providing a follow-up activities database that includes follow-up activities correlated with activity entries and identifying the follow-up activities in the follow-up activities database that are correlated with the identified activity entry.

28. The method of claim 1 wherein a first identified activity entry specifies a first unfulfilled order wherein an unfulfilled order is a physician requested and currently unscheduled activity and wherein at least one of the follow-up activities includes an indication that the first unfulfilled order should be scheduled.

29. The method of claim 28 further including the step of enabling the patient to schedule an appointment for the first unfulfilled order via the kiosk.

30. The method of claim 29 further including the step of providing a resource schedule database that includes resource schedules for resources required to complete unfulfilled orders and wherein the step of enabling the patient to schedule an appointment includes, identifying at least a first open time slot in the resource schedules for the resources required to complete the first unfulfilled order and presenting the first time slot and the first unfulfilled order for selection by the patient.

31. The method of claim 30 wherein the step of identifying at least a first open time slot includes identifying a plurality of open time slots in the resource schedules for the resources required to complete the first unfulfilled order and presenting the plurality of time slots and the first unfulfilled order for selection by the patient.

32. The method of claim 1 wherein the follow-up activities associated with at least one of the identified activity entries include instructions regarding post appointment care.

33. The method of claim 1 wherein the follow-up activities associated with at least one of the identified activity entries include creating a referral for the patient to see another physician.

34. The method of claim 1 wherein the follow-up activities associated with at least one of the identified activity entries include creating a lab order for the patient.

35. The method of claim 1 wherein the selected time is on a first day
    the step of identifying at least one suggested appointment schedule includes identifying the currently scheduled appointments for the patient that are to occur on the first day and at least one open time slot that is temporally proximate at least one of the initial time slots during which the patient may complete the unscheduled activity.

36. The method of claim 35 wherein temporally proximate time slots include time slots that are one of (1) within one hour of the beginning of one of the currently scheduled appointments and (2) within one hour of the end of one of the currently scheduled appointments.

37. The method of claim 1, wherein the patient circumstance comprises at least one of an age, a gender, and a medical history.

* * * * *